United States Patent
Cavallo et al.

(10) Patent No.: US 10,849,967 B2
(45) Date of Patent: Dec. 1, 2020

(54) NUCLEIC ACID MOLECULES ENCODING FOR CHIMERIC CSPG4 PROTEINS AND THERAPEUTIC USES THEREOF

(71) Applicants: Università degli Studi di Torino, Turin (IT); The General Hospital Corporation, Boston, MA (US)

(72) Inventors: Federica Cavallo, Turin (IT); Paolo Buracco, Grugliasco (IT); Federica Riccardo, Turin (IT); Maddalena Arigoni, Turin (IT); Elena Quaglino, Turin (IT); Raffaele Adolfo Calogero, Turin (IT); Soldano Ferrone, Boston, MA (US)

(73) Assignee: Università degli Studi di Torino, Turin (IT)

( * ) Notice: Subject to any disclaimer, the term of this patent is extended or adjusted under 35 U.S.C. 154(b) by 18 days.

(21) Appl. No.: 16/067,102

(22) PCT Filed: Dec. 28, 2016

(86) PCT No.: PCT/IB2016/058042
§ 371 (c)(1),
(2) Date: Jun. 28, 2018

(87) PCT Pub. No.: WO2017/115292
PCT Pub. Date: Jul. 6, 2017

(65) Prior Publication Data
US 2019/0008940 A1     Jan. 10, 2019

(30) Foreign Application Priority Data

Dec. 30, 2015  (IT) ................ 102015000088978

(51) Int. Cl.
| C07K 14/47 | (2006.01) |
| C12N 15/09 | (2006.01) |
| A61K 48/00 | (2006.01) |
| A61K 39/00 | (2006.01) |
| C07K 14/705 | (2006.01) |

(52) U.S. Cl.
CPC .. *A61K 39/001174* (2018.08); *A61K 39/0011* (2013.01); *A61K 48/00* (2013.01); *C07K 14/4725* (2013.01); *C07K 14/4748* (2013.01); *C07K 14/705* (2013.01); *C12N 15/09* (2013.01); *A61K 2039/53* (2013.01)

(58) Field of Classification Search
None
See application file for complete search history.

(56) References Cited

PUBLICATIONS

Riccardo et al., Clin. Cancer Res., 2014, vol. 20(14): 3753-3762.*
International Search Report and Written Opinion of the ISA for PCT/IB2016/058042, dated Mar. 27, 2017, 14 pages.
Riccardo et al., "CSPG4-Specific Immunity and Survival Prolongation in Dogs with Oral Malignant Melanoma Immunized with Human CSPG4 DNA", Clinical Cancer Research, vol. 20, No. 14, Jul. 15, 2014, pp. 3753-3762.
Cavallo et al., "Xenogene vaccination in the therapy of cancer", Expert Opinion on Biological Therapy, vol. 14, No. 10, Oct. 2014, pp. 1427-1442.
Mayayo et al., "Chondroitin sulfate proteoglycan-4: A biomarker and a potential immunotherapeutic target for canine malignant melanoma", the Veterinary Journal, vol. 190, No. 2, Feb. 23, 2011, pp. e26-e30.

* cited by examiner

*Primary Examiner* — Xiaozhen Xie
(74) *Attorney, Agent, or Firm* — Nixon & Vanderhye, PC

(57) ABSTRACT

A nucleic acid molecule encoding a chimeric chondroitin sulfate proteoglycan 4 (CSPG4) protein, wherein the chimeric CSPG4 protein comprises, from the N-terminal to the C-terminal: i) a first portion derived from the human CSPG4 sequence and a second portion derived from the canine CSPG4 sequence or ii) a first portion derived from the canine CSPG4 sequence and a second portion derived from the human CSPG4 sequence.

10 Claims, 6 Drawing Sheets

Specification includes a Sequence Listing.

```
GAATTCATGCAGTCCGGGCCGCGGCCCCCACTTCCAGCCCCGGCCTGGCCTTGGCTTTGACCCTGACTATGTTGGCCAG
ACTTGCATCCGCGGCTTCCTTCTTCGGTGAGAACCACCTGGAGGTGCCTGTGGCCACGGCTCTGACCGACATAGACCTGC
AGCTGCAGTTCTCCACGTCCCAGCCCGAAGCCCTCCTTCTCCTGGCAGCAGGCCCAGCTGACCACCTCCTGCTGCAGCTC
TACTCTGGACGCCTGCAGGTCAGACTTGTTCTGGGCCAGGAGGAGCTGAGGCTGCAGACTCCAGCAGAGACGCTGCTGAG
TGACTCCATCCCCCACACTGTGGTGCTGACTGTCGTAGAGGGCTGGGCCACGTTGTCAGTCGATGGGTTTCTGAACGCCT
CCTCAGCAGTCCCAGGAGCCCCCTAGAGGTCCCCTATGGGCTCTTTGTTGGGGGCACTGGGACCCTTGGCCTGCCCTAC
CTGAGGGGAACCAGCCGACCCCTGAGGGGTTGCCTCCATGCAGCCACCCTCAATGGCCGCAGCCTCCTCCGGCCTCTGAC
CCCCGATGTGCATGAGGGCTGTGCTGAAGAGTTTTCTGCCAGTGATGATGTGGCCCTGGGCTTCTCTGGGCCCCACTCTC
TGGCTGCCTTCCCTGCCTGGGGCACTCAGGACGAAGGAACCCTAGAGTTTACACTCACCACACAGAGCCGGCAGGCACCC
TTGGCCTTCCAGGCAGGGGCCGGCGTGGGGACTTCATCTATGTGGACATATTTGAGGGCCACCTGCGGGCCGTGGTGGA
GAAGGGCCAGGGTACCGTATTGCTCCACAACAGTGTGCCTGTGGCCGATGGGCAGCCCCATGAGGTCAGTGTCCACATCA
ATGCTCACCGGCTGGAAATCTCCGTGGACCAGTACCCTACGCATACTTCGAACCGAGGAGTCCTCAGCTACCTGGAGCCA
CGGGGCAGTCTCCTTCTCGGGGGCTGGATGCAGAGGCCTCTCGTCACCTCCAGGAACACCGCCTGGGCCTGACACCAGA
GGCCACCAATGCCTCCCTGCTGGGCTGCATGGAAGACCTCAGTGTCAATGGCCAGAGGCGGGGCTGCGGGAAGCTTTGC
TGACGCGCAACATGGCAGCCGGCTGCAGGCTGGAGGAGGAGGAGTATGAGGACGATGCCTATGGACATTATGAAGCTTTC
TCCACCCTGGCCCCTGAGGCTTGGCCAGCCATGGAGCTGCCTGAGCCATGCGTGCCTGAGCCAGGGCTGCCTCCTGTCTT
TGCCAATTTCACCCAGCTGCTGACTATCAGCCCACTGGTGGTGGCCGAGGGGGCACAGCCTGGCTTGAGTGGAGGCATG
TGCAGCCCACGCTGGACCTGATGGAGGCTGAGCTGCGCAAATCCCAGGTGCTGTTCAGCGTGACCCGAGGGGCACGCCAT
GGCGAGCTCGAGCTGGACATCCCGGGAGCCCAGGCACGAAAAATGTTCACCCTCCTGGACGTGGTGAACCGCAAGGCCCG
CTTCATCCACGATGGCTCTGAGGACACCTCCGACCAGCTGGTGCTGGAGGTGTCGGTGACGGCTCGGGTGCCCATGCCCT
CATGCCTTCGGAGGGGCCAAACATACCTCCTGCCCATCCAGGTCAACCCTGTCAATGACCCACCCCACATCATCTTCCCA
CATGGCAGCCTCATGGTGATCCTGGAACACACGCAGAAGCCGCTGGGGCCTGAGGTTTTCCAGGCCTATGACCCGGACTC
TGCCTGTGAGGGCCTCACCTTCCAGGTCCTTGGCACCTCCTCTGGCCTCCCCGTGGAGCGCCGAGACCAGCCTGGGGAGC
CGGCGACCGAGTTCTCCTGCCGGGAGTTGGAGGCCGGCAGCCTAGTCTATGTCCACCGCGGTGGTCCTGCACAGGACTTG
ACGTTCCGGGTCAGCGATGGACTGCAGGCCAGCCCCCCGGCCACGCTGAAGGTGGTGGCCATCCGGCCGGCCATACAGAT
CCACCGCAGCACAGGGTTGCGACTGGCCCAAGGCTCTGCCATGCCCATCTTGCCCGCCAACCTGTCGGTGGAGACCAATG
CCGTGGGGCAGGATGTGAGCGTGCTGTTCCGCGTCACTGGGGCCCTGCAGTTTGGGGAGCTGCAGAAGCAGGGGGCAGGT
GGGGTGGAGGGTGCTGAGTGGTGGGCCACACAGGCGTTCCACCAGCGGGATGTGGAGCAGGGCCGCGTGAGGTACCTGAG
CACTGACCCACAGCACCACGCTTACGACACCGTGGAGAACCTGGCCCTGGAGGTGCAGGTGGGCCAGGAGATCCTGAGCA
ATCTGTCCTTCCCAGTGACCATCCAGAGAGCCACTGTGTGGATGCTGCGGCTGGAGCCACTGCACACTCAGAACACCCAG
CAGGAGACCCTCACCACAGCCCACCTGGAGGCCACCCTGGAGGAGGCAGGCCCAAGCCCCCCAACCTTCCATTATGAGGT
GGTTCAGGCTCCCAGGAAAGGCAACCTTCAACTACAGGGCACAAGGCTGTCAGATGGCCAGGGCTTCACCCAGGATGACA
TACAGGCTGGCCGGGTGACCTATGGGGCCACAGCACGTGCCTCAGAGGCAGTCGAGGACACCTTCCGTTTCCGTGTCACA
GCTCCACCATATTTCTCCCCACTCTATACCTTCCCCATCCACATTGGTGGTGACCCAGATGCGCCTGTCCTCACCAATGT
CCTCCTCGTGGTGCCTGAGGGTGGTGAGGGTGTCCTCTCTGCTGACCACCTCTTTGTCAAGAGTCTCAACAGTGCCAGCT
ACCTCTATGAGGTCATGGAGCGGCCCCGCCATGGGAGGTTGGCTTGGCGTGGGACACAGGACAAGACCACTATGGTGACA
TCCTTCACCAATGAAGACCTGTTGCGTGGCCGGCTGGTCTACCAGCATGATGACTCCGAGACCACAGAAGATGATATCCC
ATTTGTTGCTACCCGCCAGGGCGAGAGCAGTGGTGACATGGCCTGGGAGGAGGTACGGGGTGTCTTCCGAGTGGCCATCC
AGCCCGTGAATGACCACGCCCCTGTGCAGACCATCAGCCGGATCTTCCATGTGGCCCGGGTGGGCGGCGGCTGCTGACT
ACAGACGACGTGGCCTTCAGCGATGCTGACTCGGGCTTTGCTGACGCCCAGCTGGTGCTTACCCGCAAGGACCTCCTCTT
TGGCAGTATCGTGGCCGTAGATGAGCCCACGCGGCCCATCTACCGCTTCACCCAGGAGGACCTCAGGAAGAGGCGAGTAC
TGTTCGTGCACTCAGGGGCTGACCGTGGCTGGATCCAGCTGCAGGTGTCCGACGGGCAACACCAGGCCACTGCGCTGCTG
GAGGTGCAGGCCTCGGAACCCTACCTCCGTGTGGCCAACGGCTCCAGCCTTGTGGTCCCTCAAGGAGGCCAGGGCACCAT
CGACACGGCCGTGCTCCACCTGGACACCAACCTCGACATCCGCAGTGGGGATGAGGTCCACTACCACGTCACAGCTGGCC
CTCGCTGGGGACAGCTAGTCCGGGCTGGTCAGCCAGCCACAGCCTTCTCCCAGCAGGACCTGCTGGATGGGCCGTTCTC
TATAGCCACAATGGCAGCCTCAGCCCCCGCGACACCATGGCCTTCTCCGTGGAAGCAGGGCCAGTGCACACGGATGCCAC
CCTACAAGTGACCATTGCCCTAGAGGGCCCACTGGCCCCACTGAAGCTGGTCCGGCACAAGAGATCT
```

Fig. 4A

```
ACGTCTTCCAGGGGGAGGCAGCTGAGATCAGAAAGGATCAGCTGGAGGCAGCGCAGGAGGCAGTGCCGCCCGCCCAAATT
GTGTTCTCGGTGAAGACCCGCCGCGGGCCGGCTACCTGGTGATGCTGTCCCGCGGCGCCTCCGTGGCCGGGCCGCCCAG
CTGGGACCCCGTGCAGAGCTTCTCCCAGGAGGCGGTGGACGCCGGCAGGGTCCTGTACCTCCACTCCCGCCCCGAGGCCT
GGAGTGACTCCTTCTCCCTAGACGTGGGCTCAGGCCTGGGTGCGCCCCTCGAGGGCGTCCGCGTGGAGCTGGAGGTGCTG
CCCGCCACCATCCCACTGGAGGCACAGAACTTCAGCGTCCCCGAGGGCGGCAGCCGCGTGCTGGCCCCCCCGCTGCTCCA
GGTCGCCGGGCCCTACTTCCCTGCACTGCCCGGCCTCGAACTGCGGGTCCTCGAGCAGCCCTGCACGGGGCCCTGCGGA
GAGAGGAGGCCCCTCAAGCGGGGACCCTCAGCGCTTTCTCCTGGAAAGAGGTAGAACAGCAGCAGATCCGCTATGTGCAC
GACGGGAGTGAGACGCTGACAGACAGCTTCACCCTAGTGGCTAACGCCTCCGAGCTGGACCGCCAGAGCCACCCTGTGGC
CTTCACCATCACCGTCCTGCCCGTCAATGACCAACCGCCCATCCTCACCGCAAACACAGGCCTAACGATGTGGGAGGGGG
CCACCGTGCCCTTCCCTCCGGAGGCCCTGAGGGGTGCGGACAGCGACTCGGGCCCGGAGGACCTGGTCTACACCATCGAG
CGGCCCAGCAACGGGCAGGTGGTGCTGCGGGCGGCGCCAGGCACCGAGGTGCACAGCTTCACGCAGGCCCAGCTGGACGA
CGGGCTCGTGCTGTTCTCACACAGAGGAGCCCTGGACGGAGGCTTCCGCTTCAGCCTGTCCGACGGCGAGCACGCTTCCC
CCGGACACTTCTTCCGCGTGACGGCCCAGAAGCAGCTGCTCCTCTCCTGGAGGGCAGCCGGACGCTGACCGTGTGCCCA
GGGTCGGTCCAGCCGCTCAGCAGCCAGAGCCTGAGAGCCAGCTCCAGTGCCGGCACCGATCCGCAGCACCTGCTCTACCG
GGTGGTGCAGGGCCCCCGGCTGGGCCGCCTGCTCCGCGCCCAGCAGGGCGGCACCGGGGAGGTCCTGGTGAACTTCACGC
AAGCCGAGGTATACGCGGCGGATGTTGTGTATGAGCACAAGATGCCTGCTGAGCCCTTCTGGGAGGTCCACGACGCCCTG
GAGCTCCGGCTGTCCTCGCCCCCCGCCCCCGACGTGGCCGCCACCCTGGAGGTGGCCGTGTCCTTCGAGGCCGCCTGCCC
GCAGCGCCCCAGCCGCCTCTGGAGGAACGAGGGTCTCTGGGTGGCCGAGGGCCAGCAGGCGGACATCACCAGCGCCGCCC
TGGACGCCTCCAACCTGCTGGCGCGCGTCCCCGCCGCGCTGCGCGCCCGGCACGACGTGCTGTTCCAGGTGACGCGGTTC
CCGGCGCGGGCCGGCTGCTGCTGGCGGGCGGGCGCTGCACGCGGGCCGGGCGCACTTCCTGCAGTCGGAGCTGGCGGC
GGGGCTCCTGGCCTACGCGCACGGCGGCGGGGGCGCGCAGCCCGACGGCTTCGGCTTCCGCGCGCAGCTGCAGGGCCCCG
CGGGCGCCGGGCCGGGCGCGCTCCCCGCGCTCCCCGCGCTCCCCGACGAGGCCTTCGCCGTGCGCGTGGGGGCCGCGGCG
TCCGAGCCGCTGCGCCTGCCCCGCGGCTCCCGCGCGCCCGTGTCCCGCGCGCAGCTCCGCGTGCAGCTCCCGGGCGCCGC
GCCCGCCGACGTGCAGTACGAGGTGCGGCGCGCGGCCCCCGGCGGCTTCCTGAGCCTCGCGGGCGCGGGCGCGGGCCCGG
TGCGCCGCTTCTCGCAGGCCGACGTGGACGCGGGCCGCCTGGCCTTCGTGGCCAACGGCAGCAGCGTGGCGGGCGTGCTG
CAGCTGAGCGCGTGGGCCGGCGCCAGCCCGCGCGTGCCCGTGGCGCTGGCCGTGGACGTGCTGCCCGCCGCCATCGAGGT
GCAGCTGCGCGCGCCCCTGGAGGTGCCCCAGGCGCTGGGGCGCTGCGCGCTCGGGCCGCGGCAGCTGCGCGTCGTGTCGG
ACCGCGCCGAGCCCGAGGCCGCCTACCGCGTGACCCGGGCGCCGCGCTTCGGGCAGCTCCTGGTGGCGGGCAGGCCGGCC
GGCGCCTTCAGCCAGCGGCAGGTGGACCGCGGCGACGTGGAGTTCGCCTTCACCGACCTGTCCTCCCGCGCGACCGCTT
CGCCGTCCTGGCCCACGCGCGGGGCGCCAACGCCACGGCCACGGTGGACGTCACGGTCGCGGCGCTGCTGCGGGTCGGGC
CCCGGGGGCCGTGGCCGCAGGGCGCCACCCTGCGCCTGGACCCGGCCGTCCTGGACGCCGCCGAGCTGGCCAACCGCACG
GGCGGGGAGCCGCGCTTCCGCCTGCTGGCCGGGCCCCGGCTGGGCCGCCTGGTGCGCGTGGCCCGCGCGGGGCCGGAGCC
CGTGGAGCAGTTCACGCAGCGGGACCTGGAGGGCGGGAGGCTGGGGCTGCAGCTGGGCCGCGCCCCCGGCCCCACGGGCG
ACAGCCTCACGCTGGAGCTGTGGGCGCCCGGCGTCCCCCGGCCGTGGCCTCCCTGGACTTCCACACCGAGCCCTACGAC
GCGGCGCGCCCCTACGGCGTGGCCCTGCTCAGCCTCCCCGAGGAAGCCGGGGCACCCGACAGCGGCGCCCCGGCCACGGG
CCAGCCGGGCGCGCCAGGCCCCAGCCCCGGGCCCACCGCGGCCAGCGGCGGCTTCCTGGGCCTCCTGGAGGCCAACATGT
TCAGCATCATCATCCCCGTGTGCCTGGTCCTCCTGCTCCTGGCCCTGCTCCTGCCGCTGCTCTTCTACCTGCGCAAGCGG
AACAAGACGGGCAAGCACGACGTCCAGGTGCTGACCGCCAAGCCCCGCAACGGCCTGGCCGGCGACACGGAGACCTTCCG
CAAGGTGGAGCCGGGCCACGCCATCCCGCTCACGGCCGTGCCCGGCCAGGGGCCCCGCCCGGCGGCCAGCCCGACCCAG
AGCTGCTGCAGTACTGTCGGACACCCAACCCCGCCCTCAAAAACGGCCAGTACTGGGTGTAGTCTAGA
```

Fig. 4B

```
GAATTCATGGCCCTCGGTGCTCTGCAGAGCTGCTCCATCCGCCACTCAGAGTCCCAGGGACCCCTTCCTTCAAAGTGTCGGGGCCTGGG
TGATGGGCTGGGCCTCTGGAGAGGTGGGCAGGGGCCATCTGAGGTGACCAGAGTGGGCCATTTGGGCAGCCTGCAGGCTCCAGCCGAGC
GATTCCAGCACCCGCTCTCCTTGGGCTTCGACGGGAACCCACTCTCCAATATCTTCTCAGCATCCACGCTGTACGAGCATTGGCGGGAC
AGGAGGGTCTTCTGGTGCTGCCGCCTGGGGCCGGGTGGCCAGGTGGGCCAGGCTGCTGGCGAGGTTGCGGGAGGGGAGCGGGTGCGCAT
GGAGCTCTCAGAGGAAGTGCACAGGCTGCTTCTGGGAACTGGGCGTGCTGCCCAGGAGGGGCAGGCAGGGGAGGGGGTTGGAAGAGCCC
GCCGCACACCCTCACTGGCGCACACAGATGTGGGTGTGCGCACAAGTATGAACAACCGCGAGCAGGTGCCCAAGGGGCCCTCGGGCCTG
GGCCTGCTCCTGCTCCCCAGCTCCTGGCTCCACCCAGCTCCCCTCTTGCCTCCAACATGCCCCCTGCCCCAACCCTGGGCATTCGGGG
CGAGCCCGTGTCCCACGGGCGGCCGAGGAGCTCGGCCATCAGGCCTTTCTGCCAAAGCCGTGACCTCCGTCAGCGTGATGCCCGGGAGG
TACACGTACGCACATGCGTGCACACGCGCGTGCAAGTGTTGCTCAGCAGCCTGGCCCAGAGCCTAGCAAGGAGAGCGCCCAGCCCCTCA
GCAGCCATCCCGGGAGAAACCCCCGACTCAGGATTCACGGCCCCCAGCACCACGGCCAGGGGCCTTGGGGGCATTGGCAAGAGGGCCCA
GGACCCCGGAGAGTTGGTGCTGGAGACAGAGACGTGGGGGCAGGTGGTTCAGGGGTTAGAGCCAGCCAGCGCCTTCACTTCCGGCCTGG
TACGGGCCCTGAGGCCCTATGACGATGTCCCTGCATCCAGCTTCAACAGAGGGGAGTCTACAGACCCAGGCTGGGAAAAGCCAGCTGTA
GTCGGCTATGGCTCCCCAGCCATCGTGGGAACAACAGGGCCGGATCTGACTGCCCCCAGGGACAATCAGCAGCCTTGCGGCAGGAAGC
AATACGGCGTGATGCAGGAAGCTGGGGCCCATTTGGGGTCCAGTACGTGGTCTCCATCTGGCCTCAGCGCCTTCGCTCTTTGGTGGACT
CGGGCTGGCGACTGCACCCTTACTCCAAAGACAGCTGGGAGAGAAGTGAGGGGGCAGTGCCAGCCAGGACCGTGAAGCTGCGCCAGCAC
AAAACCCGCATCGTCCGCAGCACCTCTCCTCCTCCAGCCTCCTTCTTTGGGGAGAACCACCTGCAGGTGCCGGTGACCACAGCTCTGAG
CAACATAGACCTCCGGCTACAATTCTCCACGTCCCAGCCCGAAGCCCTGCTCCTCCTGGCAGCAGGCCAGGCTGACCACCTCCTCCTGC
AGCTCCACTCCGGATACCTGCAGGTCAGACTCACCCTGGGCCAGGAGGAGCTGAGGCTGCAGACCCCAGCTGAGACTCCGCTGAGCGAC
TCCGCCGTCCACTCCGTGGAGCTGACTGTGTCAGACAGCGAGGCCTCGTTGTCCGTCGATGGGCTGCTGAACGCCTCAGCCCCCGTCCT
GGGAGCTCCCCTGGAGGTCCCCTATGGGATCTTCCTGGGGGGCACTGGGAGCCTGAGCCTGTCCTACCTGATGGGAGCCAGCCGGCCCC
TGAGGGGCTGCCTGCACGCCGCCACCGTCAACGGCCGCAACCTCCTCCGACCACTGACCCCTGACGTGCACGAGGGCTGCGCTGAAGAG
TTTTCTGCTGATGACAGCGTGGCTCTGGGCTTCTCTGGGCCCCACTGCTGGCTGCCTTCCCTGCCTGGAACACTCGGGAGGAGGGCAC
CCTGGCGTTCATACTCACCACTCGGAGCCGACAGGCGCCCTGGCTTTCCAGGCGGGCGGCCGGCACGGGGATTTCATCTACGTGGACA
TATTTGAGGGCCACCTGCGGGCTGTGGTGGAGAAGGGCCAGGGCACCGTGTTGCTCCACAACAGCGTGCCCGTGGCTGACGGGCTACCC
CATGAGGTCAGTGTCCACGTGGATGCTCACCAGCTGGAAATCTCCGTGGACCAGTACCCCACACGGACTTCCAACCGTGGGATCCTCAG
CTACCTGGAACCCGCGGCAGTCTCCTCCTGGGGGGGCTGGACACAGAGGCCTCCCGCCACCTCCAGGAACACCGCCTGGGCCTGGCCT
CGGGGGCCGTCAACGTCTCCCTCCTGGGCTGCATGGAGGATCTCAGCATCAACGGCCAGAGGCAGGGGCTCCGGGAAGCCTCGCTGACT
CGCAGCATGGTGGCCGGCTGCAGCCTGGAGGAAGACGAGTACGAGGAGGACACCTACGGCACCTATGAAGCTCTCTCCACCCTGGCACC
GGAGGCCTGGTCCGCCGTGGAGCTGCCCGAGCCCTGCGTGCCCGAACCGGGGCTGCCTCCCGTCTTTGCCAACTTCACCCAACTGCTGA
CTGTCAGCCCGCTGGTGGTGGCCGAGGGGGGCACAGCCTGGCTTGAGTGGCGGCACCTGCAGCCCACGCTGGACCTGAGCGAGGCCGAG
CTGCGTAAATCCCAGGTGCTGTTCAGCGTGAGCCGTGGGGCCCGCCACGGGGAGCTCGAGCTGGACGTCCCGGGAGCCCAGGCACGGAA
AATGTTCACCCTCCTGGACGTGGTGAACCGCAAGGCCCGCTTCGTCCACGATGGCTCGGAGGAGACCTCCGACCAGCTGATGCTGGAGG
TGTCCGTGACCGCCAGGGGCCCTGTGCCCTCCTGCCTCCGGAGGGGCCAGACTTACATCCTGCCCATCCAGATAAACCCGGTCAACGAC
CCACCCCAAATCATCTTCCCCCACGGCAGCCTCATGGTGATCCTGGAACACACACAGAAGCCCCTGGGGCCCGAGGTCTTCCAGGCCTA
CGACCCAGACTCTGCCTGCGAGGGCCTCACCTTCCAGCTCCTTGGCACCGCCCGGGCCTGCCGGTGGAGCGCCAGGAGCAGCCCGGGG
AGCCAGCCACCGAGTTCTCCTGCCGGGAGCTGGAGGCGGGCGGCCTGGTCTACGTGCACCGGAGCGGGCCCGCCCAGGACCTGACGTTC
CGCGTCAGCGACGGGCTGCAGGCCAGCGCTCCGGCCACGCTGCAGGTGGTGGCGGTCCGGCCCAGCATCCGGGTCCGCCACAACACGGG
GCTGCGCCTGGCCCAGGGCTCCGCCGCCCCGGTGCTGCCCGCCAATCTGTCGGTGGAGACCAACGCGGTGGGGCAGGATGTGAGCGTGC
TGTTCCGGGTCGCCGCGCCCCTGCGGTTCGGGGAGCTGCAGAAGCAGGGCGCGGGGGGCGCCGAGGGCGCGGAGTGGCGCCCGGTGCAG
GCCTTCCAGCAGCGGGACGTGGAGCAGGGCCGCGTGAGGTACCTGAGCACCGACCCGCAGCACCGCACGGAGGACGCCGTGGAGCGCGT
GGCCCTGGAGGTTCAGGTGGGCCAGGAGACCCTGAGCAATCTGTCCTTCCTGGTGACGATCCAGAGAGCCACCGTGCGGCTGCTGCGGC
TCGAGCCCCTGCGCACCCACACCACGCGGGCAGGAGGCGCTCACCGGCGCGCACCTGGAGGCCGCTCTGGAGGAGGGGCGGGCCCCAGC
CCCACCACCTTCCACTACGAGCTGGTTCAGGCCCCAGGAAGGGTAACCTCAGGCTGCAGGGCGCCCGGCTGTCCGAGGGGCAGGGCTT
CACCCAGGATGACCTGCAGGCCGGCCGGGTGACCTACGGGCCACGGCGCGCACCTCGGAGACCGTGGAGGACGCCTTCCGTTTCCGCG
TCACGGCTCCGCCACATTTCTCCCCGCTCTACACCTTCCCCATCCACATCGGGGTGACCCCGACGCCCCGTCCTCACCAACGTCCTC
CTCTCCGTGCCCGAGGGAGGCGAGGGCGTCCTCTCCGCGGAACACCTGTTCGTCAAGAGCCTCAACAGCGCCAGCTACCTCTATGAGGT
CATGGAGCGGCCCCGCCACGGGCGGCTGGTCTGGAGGGGGCGCAGGACGAGGCCACCGCGGTGACGTCCTTCACCAACGAGGACCTGC
TGCAGGGCCGGCTGGTCTACCAGCATGACAACTCCGAGACCACGGAAGACGACATCCCCTTCGTGGCAACCCGCCAGAGTGAGGGCAGC
GGCGGCCTGGCCTGGGAGGAGGTCCGGGGCGTCTTCCGCGTGGCCATCCAGCCCGTGAACGACCACGCTCCCGTGCAGACCGTCAGCCG
CGTCTTCCACGTGGCCCGGGGCGGGCGGCGGCTGCTGACGACCGACGACGTGGCCTTCAGTGACGCCGACTCCGGCTTCGCCGACGCGC
AGCTGGTGCTGACCCGCAAGGACCTTCTCTTCGGCAGCATCGTGGCCGCGGACGAGCCCACGCGGCCCATCTACCGCTTCTCCCAGGAG
GACCTCCGGAAGAGGCGCGTCCTGTTCGTGCACTCCGGGCCGACCGCGGCTGGATCCAGCTGCAGGTGTCCGACGGGCGGCACCAGGC
CACCGCGCTGCTTGAAGTGCAGGCATCCGAGCCCTATCTCCGCGTGGCCAATGGCTCCAGCCTCGTGGTCCCTCAGGGGGCCAGGGCA
CCATCGACACAGCCGTGCTCCGCCTGGACACCAACCTAGACATTCGCAGCGGGGATGAGGTCCGCTACCGTGTCACAGCCGGCCCGCAC
TGGGGGCAGCTGCTCCGGGCCGGCCAGCCGGCCACAGCCTTCTCCCAACAGGACCTGCTGGACGGGCCGTCCTCTACAGCCACAACGG
CAGCCTGAGCCCGCAGGACACCCTGGCCTTCTCCGTGGAGGCAGGGCCTGTGCTCACGGATGCCACCGTGCAGGTGACCATTGCCTTGG
AGGGGCCATTGGCCCCACTGCATCTGGTCCAGAACAAGAAGATCT
```

Fig. 5A

```
ACGTCTTCCAGGGAGAGGCAGCTGAGATCAGAAGGGACCAGCTGGAGGCAGCCCAGGAGGCAGTGCCACCTGCAGACATC
GTATTCTCAGTGAAGAGCCCACCGAGTGCCGGCTACCTGGTGATGGTGTCGCGTGGCGCCTTGGCAGATGAGCCACCCAG
CCTGGACCCTGTGCAGAGCTTCTCCCAGGAGGCAGTGGACACAGGCAGGGTCCTGTACCTGCACTCCCGCCCTGAGGCCT
GGAGCGATGCCTTCTCGCTGGATGTGGCCTCAGGCCTGGGTGCTCCCCTCGAGGGCGTCCTTGTGGAGCTGGAGGTGCTG
CCCGCTGCCATCCCACTAGAGGCGCAAAACTTCAGCGTCCCTGAGGGTGGCAGCCTCACCCTGGCCCCTCCACTGCTCCG
TGTCTCCGGGCCCTACTTCCCCACTCTCCTGGGCCTCAGCCTGCAGGTGCTGGAGCCACCCCAGCATGGAGCCCTGCAGA
AGGAGGACGGACCTCAAGCCAGGACCCTCAGCGCCTTCTCCTGGAGAATGGTGGAAGAGCAGCTGATCCGCTACGTGCAT
GACGGGAGCGAGACACTGACAGACAGTTTTGTCCTGATGGCTAATGCCTCCGAGATGGATCGCCAGAGCCATCCTGTGGC
CTTCACTGTCACTGTCCTGCCTGTCAATGACCAACCCCCATCCTCACTACAAACACAGGCCTGCAGATGTGGGAGGGGG
CCACTGCGCCCATCCCTGCGGAGGCTCTGAGGAGCACGGACGGCGACTCTGGGTCTGAGGATCGGTCTACACCATCGAG
CAGCCCAGCAACGGGCGGGTAGTGCTGCGGGGGCGCCGGGCACTGAGGTGCGCAGCTTCACGCAGGCCCAGCTGGACGG
CGGGCTCGTGCTGTTCTCACACAGAGGAACCCTGGATGGAGGCTTCCGCTTCCGCCTCTCTGACGGCGAGCACACTTCCC
CCGGACACTTCTTCCGAGTGACGGCCCAGAAGCAAGTGCTCCTCTCGCTGAAGGGCAGCCAGACACTGACTGTCTGCCCA
GGGTCCGTCCAGCCACTCAGCAGTCAGACCCTCAGGGCCAGCTCCAGCGCAGGCACTGACCCCCAGCTCCTGCTCTACCG
TGTGGTGCGGGGCCCCCAGCTAGGCCGGCTGTTCCACGCCCAGCAGGACAGCACAGGGGAGGCCCTGGTGAACTTCACTC
AGGCAGAGGTCTACGCTGGGAATATTCTGTATGAGCATGAGATGCCCCCCGAGCCCTTTTGGGAGGCCCATGATACCCTA
GAGCTCCAGCTGTCCTCGCCGCCTGCCCGGGACGTGGCCGCCACCCTTGCTGTGGCTGTGTCTTTTGAGGCTGCCTGTCC
CCAGCGCCCCAGCCACCTCTGGAAGAACAAAGGTCTCTGGGTCCCCGAGGGCCAGCGGGCCAGGATCACCGTGGCTGCTC
TGGATGCCTCCAATCTCTTGGCCAGCGTTCCATCACCCCAGCGCTCAGAGCATGATGTGCTCTTCCAGGTCACACAGTTC
CCCAGCCGGGGCCAGCTGTTGGTGTCCGAGGAGCCCCTCCATGCTGGGCAGCCCCACTTCCTGCAGTCCCAGCTGGCTGC
AGGGCAGCTAGTGTATGCCCACGGCGGTGGGGGCACCCAGCAGGATGGCTTCCACTTTCGTGCCCACCTCCAGGGGCCAG
CAGGGGCCTCCGTGGCTGGACCCCAAACCTCAGAGGCCTTTGCCATCACGGTGAGGGATGTAAATGAGCGGCCCCCTCAG
CCACAGGCCTCTGTCCCACTCCGGCTCACCCGAGGCTCTCGTGCCCCATCTCCCGGGCCCAGCTGAGTGTGGTGGACCC
AGACTCAGCTCCTGGGGAGATTGAGTACGAGGTCCAGCGGGCACCCCACAACGGCTTCCTCAGCCTGGTGGGTGGTGGCC
TGGGGCCCGTGACCCGCTTCACGCAAGCCGATGTGGATTCAGGGCGGCTGGCCTTCGTGGCCAACGGGAGCAGCGTGGCA
GGCATCTTCCAGCTGAGCATGTCTGATGGGCCAGCCCACCCCTGCCCATGTCCCTGGCTGTGGACATCCTACCATCCGC
CATCGAGGTGCAGCTGCGGGCACCCCTGGAGGTGCCCCAAGCTTTGGGCGCTCCTCACTGAGCCAGCAGCAGCTCCGGG
TGGTTTCAGATCGGGAGGAGCCAGAGGCAGCATACCGCCTCATCCAGGGACCCCAGTATGGGCATCTCCTGGTGGGCGGG
CGGCCCACCTCGGCCTTCAGCCAATTCCAGATAGACCAGGGCGAGGTGGTCTTTGCCTTCACCAACTTCTCCTCCTCTCA
TGACCACTTCAGAGTCCTGGCACTGGCTAGGGGTGTCAATGCATCAGCCGTAGTGAACGTCACTGTGAGGGCTCTGCTGC
ATGTGTGGGCAGGTGGGCCATGGCCCCAGGGTGCCACCCTGCGCCTGGACCCCACCGTCCTAGATGCTGGCGAGCTGGCC
AACCGCACAGGCAGTGTGCCGCGCTTCCGCCTCCTGGAGGGACCCCGGCATGGCCGCGTGGTCCGCGTGCCCCGAGCCAG
GACGGAGCCCGGGGGCAGCCAGCTGGTGGAGCAGTTCACTCAGCAGGACCTTGAGGACGGGAGGCTGGGGCTGGAGGTGG
GCAGGCCAGAGGGGAGGGCCCCCGGCCCCGCAGGTGACAGTCTCACTCTGGAGCTGTGGGCACAGGGCGTCCCGCCTGCT
GTGGCCTCCCTGGACTTTGCCACTGAGCCTTACAATGCTGCCCGGCCCTACAGCGTGGCCCTGCTCAGTGTCCCCGAGGC
CGCCCGGACGGAAGCAGGGAAGCCAGAGAGCAGCACCCCCACAGGCGAGCCAGGCCCCATGGCATCCAGCCCTGAGCCCG
CTGTGGCCAAGGGAGGCTTCCTGAGCTTCCTTGAGGCCAACATGTTCAGCGTCATCATCCCCATGTGCCTGGTACTTCTG
CTCCTGGCGCTCATCCTGCCCCTGCTCTTCTACCTCCGAAAACGCAACAAGACGGGCAAGCATGACGTCCAGGTCCTGAC
TGCCAAGCCCCGCAACGGCCTGGCTGGTGACACCGAGACCTTTCGCAAGGTGGAGCCAGGCCAGGCCATCCCGCTCACAG
CTGTGCCTGGCCAGGGGCCCCTCCAGGAGGCCAGCCTGACCCAGAGCTGCTGCAGTTCTGCCGGACACCCAACCCTGCC
CTTAAGAATGGCCAGTACTGGGTGTGATCTAGA
```

Fig. 5B

SEQUENCE LISTING

```
<160> NUMBER OF SEQ ID NOS: 23

<210> SEQ ID NO 1
<211> LENGTH: 33
<212> TYPE: DNA
<213> ORGANISM: artificial
<220> FEATURE:
<223> OTHER INFORMATION: primer

<400> SEQUENCE: 1
ccggaattcg ccatgcagtc cgggccgcgg ccc                                33

<210> SEQ ID NO 2
<211> LENGTH: 28
<212> TYPE: DNA
<213> ORGANISM: artificial
<220> FEATURE:
<223> OTHER INFORMATION: primer

<400> SEQUENCE: 2
ggtctagaga caccatcacc aggtagcc                                      28

<210> SEQ ID NO 3
<211> LENGTH: 33
<212> TYPE: DNA
<213> ORGANISM: artificial
<220> FEATURE:
<223> OTHER INFORMATION: primer

<400> SEQUENCE: 3
ccggaattcg cctgcttgaa gtgcaggcat ccg                                33

<210> SEQ ID NO 4
<211> LENGTH: 29
<212> TYPE: DNA
<213> ORGANISM: artificial
<220> FEATURE:
<223> OTHER INFORMATION: primer

<400> SEQUENCE: 4
ggtctagatc acacccagta ctggccgtt                                     29

<210> SEQ ID NO 5
<211> LENGTH: 6936
```

<212> TYPE: DNA
<213> ORGANISM: artificial
<220> FEATURE:
<223> OTHER INFORMATION: HuDo-CSPG4-1

<400> SEQUENCE: 5

| | | | | | |
|---|---|---|---|---|---|
| gaattcatgc | agtccgggcc | gcggccccca | cttccagccc | ccggcctggc | cttggctttg | 60 |
| accctgacta | tgttggccag | acttgcatcc | gcggcttcct | tcttcggtga | gaaccacctg | 120 |
| gaggtgcctg | tggccacggc | tctgaccgac | atagacctgc | agctgcagtt | ctccacgtcc | 180 |
| cagcccgaag | ccctccttct | cctggcagca | ggcccagctg | accacctcct | gctgcagctc | 240 |
| tactctggac | gcctgcaggt | cagacttgtt | ctgggccagg | aggagctgag | gctgcagact | 300 |
| ccagcagaga | cgctgctgag | tgactccatc | ccccacactg | tggtgctgac | tgtcgtagag | 360 |
| ggctgggcca | cgttgtcagt | cgatgggttt | ctgaacgcct | cctcagcagt | cccaggagcc | 420 |
| cccctagagg | tcccctatgg | gctctttgtt | gggggcactg | ggacccttgg | cctgccctac | 480 |
| ctgagggaa | ccagccgacc | cctgagggt | tgcctccatg | cagccaccct | caatggccgc | 540 |
| agcctcctcc | ggcctctgac | ccccgatgtg | catgagggct | gtgctgaaga | gttttctgcc | 600 |
| agtgatgatg | tggccctggg | cttctctggg | ccccactctc | tggctgcctt | ccctgcctgg | 660 |
| ggcactcagg | acgaaggaac | cctagagttt | acactcacca | cacagagccg | gcaggcaccc | 720 |
| ttggccttcc | aggcaggggg | ccggcgtggg | gacttcatct | atgtggacat | atttgagggc | 780 |
| cacctgcggg | ccgtggtgga | aagggccag | ggtaccgtat | tgctccacaa | cagtgtgcct | 840 |
| gtggccgatg | gcagccccca | tgaggtcagt | gtccacatca | atgctcaccg | gctggaaatc | 900 |
| tccgtggacc | agtaccctac | gcatacttcg | aaccgaggag | tcctcagcta | cctggagcca | 960 |
| cggggcagtc | tccttctcgg | ggggctggat | gcagaggcct | ctcgtcacct | ccaggaacac | 1020 |
| cgcctgggcc | tgacaccaga | ggccaccaat | gcctccctgc | tgggctgcat | ggaagacctc | 1080 |
| agtgtcaatg | ccagaggcg | ggggctgcgg | gaagctttgc | tgacgcgcaa | catggcagcc | 1140 |
| ggctgcaggc | tggaggagga | ggagtatgag | gacgatgcct | atggacatta | tgaagctttc | 1200 |
| tccaccctgg | ccctgaggc | ttggccagcc | atggagctgc | ctgagccatg | cgtgcctgag | 1260 |
| ccagggctgc | ctcctgtctt | tgccaatttc | acccagctgc | tgactatcag | cccactggtg | 1320 |
| gtggccgagg | gggcacagc | ctggcttgag | tggaggcatg | tgcagcccac | gctggacctg | 1380 |
| atggaggctg | agctgcgcaa | atcccaggtg | ctgttcagcg | tgacccgagg | ggcacgccat | 1440 |
| ggcgagctcg | agctggacat | cccgggagcc | caggcacgaa | aaatgttcac | cctcctggac | 1500 |
| gtggtgaacc | gcaaggcccg | cttcatccac | gatggctctg | aggacacctc | cgaccagctg | 1560 |
| gtgctggagg | tgtcggtgac | ggctcgggtg | cccatgccct | catgccttcg | gagggggccaa | 1620 |
| acatacctcc | tgcccatcca | ggtcaaccct | gtcaatgacc | cacccacat | catcttccca | 1680 |
| catggcagcc | tcatggtgat | cctggaacac | acgcagaagc | cgctggggcc | tgaggttttc | 1740 |
| caggcctatg | acccgactc | tgcctgtgag | ggcctcacct | tccaggtcct | tggcacctcc | 1800 |
| tctggcctcc | ccgtggagcg | ccgagaccag | cctggggagc | cggcgaccga | gttctcctgc | 1860 |
| cgggagttgg | aggccggcag | cctagtctat | gtccaccgcg | gtggtcctgc | acaggacttg | 1920 |
| acgttccggg | tcagcgatgg | actgcaggcc | agccccccgg | ccacgctgaa | ggtggtggcc | 1980 |
| atccggccgg | ccatacagat | ccaccgcagc | acagggttgc | gactggccca | aggctctgcc | 2040 |
| atgcccatct | gcccgccaa | cctgtcggtg | gagaccaatg | ccgtgggca | ggatgtgagc | 2100 |
| gtgctgttcc | gcgtcactgg | ggccctgcag | tttggggagc | tgcagaagca | gggggcaggt | 2160 |

```
ggggtggagg gtgctgagtg gtgggccaca caggcgttcc accagcggga tgtggagcag    2220
ggccgcgtga ggtacctgag cactgaccca cagcaccacg cttacgcacac cgtggagaac   2280
ctggccctgg aggtgcaggt gggccaggag atcctgagca atctgtcctt cccagtgacc    2340
atccagagag ccactgtgtg gatgctgcgg ctggagccac tgcacactca gaacacccag    2400
caggagaccc tcaccacagc ccacctggag gccaccctgg aggaggcagg cccaagcccc    2460
ccaaccttcc attatgaggt ggttcaggct cccaggaaag gcaaccttca actacagggc    2520
acaaggctgt cagatggcca gggcttcacc caggatgaca tacaggctgg ccgggtgacc    2580
tatggggcca cagcacgtgc ctcagaggca gtcgaggaca ccttccgttt ccgtgtcaca    2640
gctccaccat atttctcccc actctatacc ttccccatcc acattggtgg tgacccagat    2700
gcgcctgtcc tcaccaatgt cctcctcgtg gtgcctgagg gtggtgaggg tgtcctctct    2760
gctgaccacc tctttgtcaa gagtctcaac agtgccagct acctctatga ggtcatggag    2820
cggcccccgcc atgggaggtt ggcttggcgt gggacacagg acaagaccac tatggtgaca    2880
tccttcacca atgaagacct gttgcgtggc cggctggtct accagcatga tgactccgag    2940
accacagaag atgatatccc atttgttgct acccgccagg gcgagagcag tggtgacatg    3000
gcctgggagg aggtacgggg tgtcttccga gtggccatcc agcccgtgaa tgaccacgcc    3060
cctgtgcaga ccatcagccg gatcttccat gtggcccggg gtgggcggcg gctgctgact    3120
acagacgacg tggccttcag cgatgctgac tcgggctttg ctgacgccca gctggtgctt    3180
acccgcaagg acctcctctt tggcagtatc gtggccgtag atgagccac gcggcccatc    3240
taccgcttca cccaggagga cctcaggaag aggcgagtac tgttcgtgca ctcagggggct  3300
gaccgtggct ggatccagct gcaggtgtcc gacgggcaac accaggccac tgcgctgctg    3360
gaggtgcagg cctcggaacc ctacctccgt gtggccaacg gctccagcct tgtggtccct    3420
caaggaggcc agggcaccat cgacacggcc gtgctccacc tggacaccaa cctcgacatc    3480
cgcagtgggg atgaggtcca ctaccacgtc acagctggcc ctcgctgggg acagctagtc    3540
cgggctggtc agccagccac agccttctcc cagcaggacc tgctggatgg ggccgttctc    3600
tatagccaca atggcagcct cagccccgc gacaccatgg ccttctccgt ggaagcaggg    3660
ccagtgcaca cggatgccac cctacaagtg accattgccc tagagggccc actggcccca    3720
ctgaagctgg tccggcacaa gaagatctac gtcttccagg gggaggcagc tgagatcaga    3780
aaggatcagc tggaggcagc gcaggaggca gtgccgcccg cccaaattgt gttctcggtg    3840
aagacccccgc cgcgggccgg ctacctggtg atgctgtccc gcggcgcctc cgtgccgggg    3900
ccgcccagct gggaccccgt gcagagcttc tcccaggagg cggtggacgc cggcagggtc    3960
ctgtacctcc actcccgccc cgaggcctgg agtgactcct tctccctaga cgtgggctca    4020
ggcctgggtg cgcccctcga gggcgtccgc gtggagctgg aggtgctgcc cgccaccatc    4080
ccactggagg cacagaactt cagcgtcccc gagggcggca gccgcgtgct ggccccccg    4140
ctgctccagg tcgccgggcc ctacttccct gcactgcccg gcctcgaact gcgggtcctc    4200
gagcagcccc tgcacgggggc cctgcggaga gaggaggccc ctcaagcggg gaccctcagc    4260
gctttctcct ggaaagaggt agaacagcag cagatccgct atgtgcacga cgggagtgag    4320
acgctgacag acagcttcac cctagtggct aacgcctccg agctggaccg ccagagccac    4380
cctgtggcct tcaccatcac cgtcctgccc gtcaatgacc aaccgccat cctcaccgca   4440
aacacaggcc taacgatgtg ggaggggcc accgtgccct tccctccgga ggccctgagg    4500
ggtgcggaca gcgactcggg cccggaggac ctggtctaca ccatcgagcg gcccagcaac    4560
```

| | | | | |
|---|---|---|---|---|
| gggcaggtgg | tgctgcgggc | ggcgccaggc | accgaggtgc | acagcttcac gcaggcccag | 4620 |
| ctggacgacg | ggctcgtgct | gttctcacac | agaggagccc | tggacggagg cttccgcttc | 4680 |
| agcctgtccg | acggcgagca | cgcttccccc | ggacacttct | tccgcgtgac ggcccagaag | 4740 |
| cagctgctcc | tctccctgga | gggcagccgg | acgctgaccg | tgtgcccagg gtcggtccag | 4800 |
| ccgctcagca | gccagagcct | gagagccagc | tccagtgccg | gcaccgatcc gcagcacctg | 4860 |
| ctctaccggg | tggtgcaggg | ccccggctg | ggccgcctgc | tccgcgccca gcagggcggc | 4920 |
| accggggagg | tcctggtgaa | cttcacgcaa | gccgaggtat | acgcggggga tgttgtgtat | 4980 |
| gagcacaaga | tgcctgctga | gcccttctgg | gaggtccacg | acgccctgga gctccggctg | 5040 |
| tcctcgcccc | ccgccccga | cgtggccgcc | accctggagg | tggccgtgtc cttcgaggcc | 5100 |
| gcctgcccga | gcgccccag | ccgcctctgg | aggaacgagg | gtctctgggt ggccgagggc | 5160 |
| cagcaggcgg | acatcaccag | cgccgccctg | gacgcctcca | acctgctggc gcgcgtcccc | 5220 |
| gccgcgctgc | gcgcccggca | cgacgtgctg | ttccaggtga | cgcggttccc ggcgcggggc | 5280 |
| cggctgctgc | tggcggggcg | ggcgctgcac | gcgggccggg | cgcacttcct gcagtcggag | 5340 |
| ctggcggcgg | ggctcctggc | ctacgcgcac | ggcggcgggg | gcgcgcagcc cgacggcttc | 5400 |
| ggcttccgcg | cgcagctgca | gggccccgcg | ggcgccgggc | cgggcgcgct ccccgcgctc | 5460 |
| cccgcgctcc | ccgacgaggc | cttcgccgtg | cgcgtggggg | ccgcggcgtc cgagccgctg | 5520 |
| cgcctgcccc | gcggctcccg | cgcgcccgtg | tcccgcgcgc | agctccgcgt gcagctcccg | 5580 |
| ggcgccgcgc | ccgccgacgt | gcagtacgag | gtgcggcgcg | cggccccegg cggcttcctg | 5640 |
| agcctcgcgg | gcgcgggcgc | gggcccggtg | cgccgcttct | cgcaggccga cgtggacgcg | 5700 |
| ggccgcctgg | ccttcgtggc | caacggcagc | agcgtggcgg | gcgtgctgca gctgagcgcg | 5760 |
| tgggccggcg | ccagcccgcg | cgtgcccgtg | gcgctggccg | tggacgtgct gcccgccgcc | 5820 |
| atcgaggtgc | agctgcgcgc | gcccctggag | gtgcccagg | cgctggggcg ctgcgcgctc | 5880 |
| gggccgcggc | agctgcgcgt | cgtgtcggac | cgcgccgagc | ccgaggccgc ctaccgcgtg | 5940 |
| acccgggcgc | cgcgcttcgg | gcagctcctg | gtggcgggca | ggccggccgg cgccttcagc | 6000 |
| cagcggcagg | tggaccgcgg | cgacgtggag | ttcgccttca | ccgacctgtc ctcccgcgcg | 6060 |
| gaccgcttcg | ccgtcctggc | ccacgcgcgg | ggcgccaacg | ccacggccac ggtggacgtc | 6120 |
| acggtcgcgc | cgctgctgcg | ggtcgggccc | cggggggccgt | ggccgcaggg cgccaccctg | 6180 |
| cgcctggacc | cggccgtcct | ggacgccgcc | gagctggcca | accgcacggg cggggagccg | 6240 |
| cgcttccgcc | tgctggccgg | gccccggctg | ggccgcctgg | tgcgcgtggc ccgcgcgggg | 6300 |
| ccggagcccg | tggagcagtt | cacgcagcgg | gacctggagg | gcgggaggct ggggctgcag | 6360 |
| ctgggccgcc | ccccggccc | cacgggcgac | agcctcacgc | tggagctgtg ggcgcccggc | 6420 |
| gtccccccgg | ccgtggcctc | cctggacttc | acaccgagc | cctacgacgc ggcgcgcccc | 6480 |
| tacggcgtgg | ccctgctcag | cctccccgag | gaagccgggg | cacccgacag cggcgccccg | 6540 |
| gccacgggcc | agccgggcgc | gccaggcccc | agccccgggc | ccaccgcggc cagcggcggc | 6600 |
| ttcctgggcc | tcctggaggc | caacatgttc | agcatcatca | tccccgtgtg cctggtcctc | 6660 |
| ctgctcctgg | ccctgctcct | gccgctgctc | ttctacctgc | gcaagcggaa caagacgggc | 6720 |
| aagcacgacg | tccaggtgct | gaccgccaag | ccccgcaacg | gcctggccgg cgacacggag | 6780 |
| accttccgca | aggtggagcc | gggccacgcc | atcccgctca | cggccgtgcc cggcaggggg | 6840 |
| cccccgcccg | gcggccagcc | cgacccagag | ctgctgcagt | actgtcggac acccaaccc | 6900 |

```
gccctcaaaa acggccagta ctgggtgtag tctaga                              6936
```

```
<210> SEQ ID NO 6
<211> LENGTH: 33
<212> TYPE: DNA
<213> ORGANISM: artificial
<220> FEATURE:
<223> OTHER INFORMATION: primer

<400> SEQUENCE: 6
ccggaattcg ccatggccct cggtgctctg cag                                 33
```

```
<210> SEQ ID NO 7
<211> LENGTH: 28
<212> TYPE: DNA
<213> ORGANISM: artificial
<220> FEATURE:
<223> OTHER INFORMATION: primer

<400> SEQUENCE: 7
ggtctagacc cacgtctagg gagaagga                                       28
```

```
<210> SEQ ID NO 8
<211> LENGTH: 32
<212> TYPE: DNA
<213> ORGANISM: artificial
<220> FEATURE:
<223> OTHER INFORMATION: primer

<400> SEQUENCE: 8
ccggaattcg ccgccgttct ctatagccac aa                                  32
```

```
<210> SEQ ID NO 9
<211> LENGTH: 29
<212> TYPE: DNA
<213> ORGANISM: artificial
<220> FEATURE:
<223> OTHER INFORMATION: primer

<400> SEQUENCE: 9
ggtctagatc acacccagta ctggccatt                                      29
```

```
<210> SEQ ID NO 10
<211> LENGTH: 8262
<212> TYPE: DNA
<213> ORGANISM: artificial
<220> FEATURE:
<223> OTHER INFORMATION: DoHu-CSPG4-1

<400> SEQUENCE: 10
gaattcatgg ccctcggtgc tctgcagagc tgctccatcc gccactcaga gtcccaggga    60
cccttcctt caaagtgtcg gggcctgggt gatgggctgg gcctctggag aggtgggcag    120
gggccatctg aggtgaccag agtgggccat ttgggcagcc tgcaggctcc agccgagcga    180
ttccagcacc cgctctcctt gggcttcgac gggaacccac tctccaatat cttctcagca    240
tccacgctgt acgagcattg gcgggacagg agggtcttct ggtgctgccg cctggggccg    300
ggtggccagg tgggccaggc tgctggcgag gttgcgggag gggagcgggt gcgcatggag    360
ctctcagagg aagtgcacag gctgcttctg ggaactgggc gtgctgccca ggagggcag    420
gcaggggagg gggttggaag agcccgccgc acaccctcac tggcgcacac agatgtgggt    480
gtgcgcacaa gtatgaacaa ccgcgagcag gtgcccaagg ggccctcggg cctgggcctg    540
ctcctgctcc cccagctcct ggctccaccc agctcccctc ttgcctccaa catgccccct    600
```

```
gccccaaccc tgggcattcg gggcgagccc gtgtcccacg gcggccgag gagctcggcc    660
atcaggcctt tctgccaaag ccgtgacctc cgtcagcgtg atgcccggga ggtacacgta    720
cgcacatgcg tgcacacgcg cgtgcaagtg ttgctcagca gcctggccca gagcctagca    780
aggagagcgc ccagcccctc agcagccatc ccgggagaaa cccccgactc aggattcacg    840
gcccccagca ccacggccag gggccttggg ggcattggca agagggccca ggaccccgga    900
gagttggtgc tggagacaga gacgtggggg caggtggttc aggggttaga gccagccagc    960
gccttcactt ccggcctggt acgggccctg aggccctatg acgatgtccc tgcatccagc   1020
ttcaacagag gggagtctac agacccaggc tgggaaaagc cagctgtagt cggctatggc   1080
tccccagcca tcgtgggaac aacagggccg gatctgactg ccccccaggg acaatcagca   1140
gccttgcggc aggaagcaat acggcgtgat gcaggaagct ggggcccatt tggggtccag   1200
tacgtggtct ccatctggcc tcagcgcctt cgctctttgg tggactcggg ctggcgactg   1260
caccccttact ccaaagacag ctgggagaga agtgagggg cagtgccagc caggaccgtg   1320
aagctgcgcc agcacaaaac ccgcatcgtc cgcagcacct ctcctcctcc agcctccttc   1380
tttggggaga accacctgca ggtgccggtg accacagctc tgagcaacat agacctccgg   1440
ctacaattct ccacgtccca gcccgaagcc ctgctcctcc tggcagcagg ccaggctgac   1500
cacctcctcc tgcagctcca ctccggatac ctgcaggtca gactcaccct gggcaggag    1560
gagctgaggc tgcagacccc agctgagact ccgctgagcg actccgccgt ccactccgtg   1620
gagctgactg tgtcagacag cgaggcctcg ttgtccgtcg atgggctgct gaacgcctca   1680
gcccccgtcc tgggagctcc cctggaggtc ccctatggga tcttcctggg gggcactggg   1740
agcctgagcc tgtcctacct gatgggagcc agccggcccc tgaggggctg cctgcacgcc   1800
gccaccgtca acggccgcaa cctcctccga ccactgaccc ctgacgtgca cgagggctgc   1860
gctgaagagt tttctgctga tgacagcgtg gctctgggct tctctgggcc ccactcgctg   1920
gctgccttcc ctgcctggaa cactcgggag gagggcaccc tggcgttcat actcaccact   1980
cggagccgac aggcgcccct ggcttttcag gcgggcggcc ggcacgggga tttcatctac   2040
gtggacatat ttgagggcca cctgcgggct gtggtgagga agggcagggg caccgtgttg   2100
ctccacaaca gcgtgcccgt ggctgacggg ctaccccatg aggtcagtgt ccacgtggat   2160
gctcaccagc tggaaatctc cgtggaccag taccccacac ggacttccaa ccgtgggatc   2220
ctcagctacc tggaaccccg cggcagtctc ctcctggggg gctggacac agaggcctcc    2280
cgccacctcc aggaacaccg cctgggcctg gcctcggggg ccgtcaacgt ctccctcctg   2340
ggctgcatgg aggatctcag catcaacggc cagaggcagg ggctccggga agcctcgctg   2400
actcgcagca tggtggccgg ctgcagcctg gaggaagacg agtacgagga ggacacctac   2460
ggcacctatg aagctctctc caccctggca ccggaggcct ggtccgccgt ggagctgccc   2520
gagccctgcg tgcccgaacc ggggctgcct ccgtctttg ccaacttcac ccaactgctg    2580
actgtcagcc cgctggtggt ggccgagggg ggcacagcct ggcttgagtg gcggcacctg   2640
cagcccacgc tggacctgag cgaggccgag ctgcgtaaat cccaggtgct gttcagcgtg   2700
agccgtgggg cccgccacgg ggagctcgag ctggacgtcc cggagcccca ggcacggaaa   2760
atgttcaccc tcctggacgt ggtgaaccgc aaggcccgct tcgtccacga tggctcggag   2820
gagacctccg accagctgat gctggaggtg tccgtgaccg ccaggggccc tgtgccctcc   2880
tgcctccgga ggggccagac ttacatcctg cccatccaga taaacccggt caacgaccca   2940
```

```
ccccaaatca tcttcccca cggcagcctc atggtgatcc tggaacacac acagaagccc    3000
ctggggcccg aggtcttcca ggcctacgac ccagactctg cctgcgaggg cctcaccttc    3060
cagctccttg gcaccgcccc gggcctgccg gtggagcgcc aggagcagcc cggggagcca    3120
gccaccgagt tctcctgccg ggagctggag gcgggcggcc tggtctacgt gcaccggagc    3180
gggcccgccc aggacctgac gttccgcgtc agcgacgggc tgcaggccag cgctccggcc    3240
acgctgcagg tggtggcggt ccggcccagc atccgggtcc gccacaacac ggggctgcgc    3300
ctggcccagg gctccgccgc cccggtgctg cccgccaatc tgtcggtgga gaccaacgcg    3360
gtggggcagg atgtgagcgt gctgttccgg gtcgccgcgg ccctgcggtt cggggagctg    3420
cagaagcagg gcgcgggggg cgccgagggc gcggagtggc gcccggtgca ggccttccag    3480
cagcgggacg tggagcaggg ccgcgtgagg tacctgagca ccgacccgca gcaccgcacg    3540
gaggacgccg tggagcgcgt ggccctggag gttcaggtgg ccaggagac cctgagcaat    3600
ctgtccttcc tggtgacgat ccagagagcc accgtgcggc tgctgcggct cgagcccctg    3660
cgcacccaca ccacgcggca ggaggcgctc accggcgcgc acctggaggc cgctctggag    3720
gaggggggcgg gccccagccc caccaccttc cactacgagc tggttcaggc ccccaggaag    3780
ggtaacctca ggctgcaggg cgcccggctg tccgagggc agggcttcac ccaggatgac    3840
ctgcaggccg gccgggtgac ctacggggcc acggcgcgca cctcggagac cgtggaggac    3900
gccttccgtt tccgcgtcac ggctccgcca catttctccc cgctctacac cttccccatc    3960
cacatcgggg gtgaccccga cgccccgtc ctcaccaacg tcctcctctc cgtgcccgag    4020
ggaggcgagg gcgtcctctc cgcggaacac ctgttcgtca agagcctcaa cagcgccagc    4080
tacctctatg aggtcatgga gcggccccgc cacgggcggc tggtctggag ggggcgcag    4140
gacgaggcca ccgcggtgac gtccttcacc aacgaggacc tgctgcaggg ccggctggtc    4200
taccagcatg acaactccga gaccacggaa gacgacatcc ccttcgtggc aacccgccag    4260
agtgagggca gcggcggcct ggctgggag gaggtccggg gcgtcttccg cgtggccatc    4320
cagcccgtga acgaccacgc tcccgtgcag accgtcagcc gcgtcttcca cgtggcccgg    4380
ggcgggcggc ggctgctgac gaccgacgac gtggccttca gtgacgccga ctccggcttc    4440
gccgacgcgc agctggtgct gacccgcaag gaccttctct tcggcagcat cgtggccgcg    4500
gacgagccca cgcggcccat ctaccgcttc tcccaggagg acctccggaa gaggcgcgtc    4560
ctgttcgtgc actccggggc cgaccgcggc tggatccagc tgcaggtgtc cgacgggcgg    4620
caccaggcca ccgcgctgct gaagtgcag gcatccgagc cctatctccg cgtggccaat    4680
ggctccagcc tcgtggtccc tcagggggc cagggcacca tcgacacagc cgtgctccgc    4740
ctggacacca acctagacat tcgcagcggg gatgaggtcc gctaccgtgt cacagccggc    4800
ccgcactggg ggcagctgct ccgggccggc cagccggcca cagccttctc ccaacaggac    4860
ctgctggacg gggccgtcct ctacagccac aacggcagcc tgagcccgca ggacaccctg    4920
gccttctccg tggaggcagg gcctgtgctc acgatgcca cctgcaggt gaccattgcc    4980
ttggaggggc cattggcccc actgcatctg gtccagaaca agaagatcta cgtcttccag    5040
ggagaggcag ctgagatcag aagggaccag ctggaggcag cccaggaggc agtgccacct    5100
gcagacatcg tattctcagt gaagagccca ccgagtgccg gctacctggt gatggtgtcg    5160
cgtggcgcct tggcagatga gccacccagc ctggaccctg tgcagagctt ctcccaggag    5220
gcagtggaca caggcagggt cctgtacctg cactcccgcc ctgaggcctg gagcgatgcc    5280
ttctcgctgg atgtggcctc aggcctgggt gctcccctcg agggcgtcct tgtggagctg    5340
```

```
gaggtgctgc cgctgccat cccactagag gcgcaaaact tcagcgtccc tgagggtggc   5400
agcctcaccc tggcccctcc actgctccgt gtctccgggc cctacttccc cactctcctg   5460
ggcctcagcc tgcaggtgct ggagccaccc cagcatggag ccctgcagaa ggaggacgga   5520
cctcaagcca ggaccctcag cgccttctcc tggagaatgg tggaagagca gctgatccgc   5580
tacgtgcatg acgggagcga gacactgaca gacagttttg tcctgatggc taatgcctcc   5640
gagatggatc gccagagcca tcctgtggcc ttcactgtca ctgtcctgcc tgtcaatgac   5700
caacccccca tcctcactac aaacacaggc ctgcagatgt gggaggggggc cactgcgccc   5760 atccctgcgg aggctctgag gagcacggac ggcgactctg gtctgaggga tctggtctac   5820
accatcgagc agcccagcaa cgggcgggta gtgctgcggg gggcgccggg cactgaggtg   5880
cgcagcttca cgcaggccca gctggacggg gggctcgtgc tgttctcaca cagaggaacc   5940
ctggatggag gcttccgctt ccgcctctct gacggcgagc acacttcccc cggacacttc   6000
ttccgagtga cggcccagaa gcaagtgctc ctctcgctga agggcagcca gacactgact   6060
gtctgcccag ggtccgtcca gccactcagc agtcagaccc tcagggccag ctccagcgca   6120
ggcactgacc cccagctcct gctctaccgt gtggtgcggg gcccccagct aggccggctg   6180
ttccacgccc agcaggacag cacaggggag gccctggtga acttcactca ggcagaggtc   6240
tacgctggga atattctgta tgagcatgag atgcccccccg agcccttttg ggaggcccat   6300
gataccctag agctccagct gtcctcgccg cctgcccggg acgtggccgc caccctttgct   6360 gtggctgtgt cttttgaggc tgcctgtccc cagcgcccca gccacctctg gaagaacaaa   6420
ggtctctggg tccccgaggg ccagcgggcc aggatcaccg tggctgctct ggatgcctcc   6480
aatctcttgg ccagcgttcc atcaccccag cgctcagagc atgatgtgct cttccaggtc   6540
acacagttcc ccagccgggg ccagctgttg gtgtccgagg agccctcca tgctgggcag   6600 ccccacttcc tgcagtccca gctggctgca gggcagctag tgtatgccca cggcggtggg   6660
ggcacccagc aggatggctt ccactttcgt gcccacctcc aggggccagc aggggcctcc   6720
gtggctggac cccaaacctc agaggcctttt gccatcacgg tgagggatgt aaatgagcgg   6780 cccccctcagc cacaggcctc tgtcccactc cggctcaccc gaggctctcg tgcccccatc   6840
tcccgggccc agctgagtgt ggtggaccca gactcagctc ctggggagat tgagtacgag   6900
gtccagcggg caccccacaa cggcttcctc agcctggtgg gtggtggcct ggggcccgtg   6960
acccgcttca cgcaagccga tgtggattca gggcggctgg ccttcgtggc caacgggagc   7020
agcgtggcag gcatcttcca gctgagcatg tctgatgggg ccagcccacc cctgcccatg   7080
tccctggctg tggacatcct accatccgcc atcgaggtgc agctgcgggc acccctggag   7140 gtgcccaag ctttggggcg ctcctcactg agccagcagc agctccgggt ggtttcagat   7200
cgggaggagc cagaggcagc ataccgcctc atccagggac cccagtatgg gcatctcctg   7260
gtgggcgggg gcccaccctc ggccttcagc caattccaga tagaccaggg cgaggtggtc   7320
tttgccttca ccaacttctc ctcctctcat gaccacttca gagtcctggc actggctagg   7380
ggtgtcaatg catcagccgt agtgaacgtc actgtgaggg ctctgctgca tgtgtgggca   7440
ggtgggccat ggccccaggg tgccaccctg cgcctggacc ccaccgtcct agatgctggc   7500
gagctggcca accgcacagg cagtgtgccg cgcttccgcc tcctggaggg accccggcat   7560
ggccgcgtgg tccgcgtgcc ccgagccagg acggagcccg ggggcagcca gctggtggag   7620
cagttcactc agcaggacct tgaggacggg aggctggggc tggaggtggg caggccagag   7680
```

-continued

| | | |
|---|---|---|
| gggagggccc ccggccccgc aggtgacagt ctcactctgg agctgtgggc acagggcgtc | 7740 | |
| ccgcctgctg tggcctccct ggactttgcc actgagcctt acaatgctgc ccggccctac | 7800 | |
| agcgtggccc tgctcagtgt ccccgaggcc gcccggacgg aagcagggaa gccagagagc | 7860 | |
| agcaccccca caggcgagcc aggccccatg gcatccagcc ctgagcccgc tgtggccaag | 7920 | |
| ggaggcttcc tgagcttcct tgaggccaac atgttcagcg tcatcatccc catgtgcctg | 7980 | |
| gtacttctgc cctggcgct catcctgccc ctgctcttct acctccgaaa acgcaacaag | 8040 |
| acgggcaagc atgacgtcca ggtcctgact gccaagcccc gcaacggcct ggctggtgac | 8100 |
| accgagacct ttcgcaaggt ggagccaggc caggccatcc cgctcacagc tgtgcctggc | 8160 |
| caggggcccc ctccaggagg ccagcctgac ccagagctgc tgcagttctg ccggacaccc | 8220 |
| aaccctgccc ttaagaatgg ccagtactgg gtgtgatcta ga | 8262 |

<210> SEQ ID NO 11
<211> LENGTH: 1920
<212> TYPE: DNA
<213> ORGANISM: artificial
<220> FEATURE:
<223> OTHER INFORMATION: HUMAN D1

<400> SEQUENCE: 11

| | | |
|---|---|---|
| atgcagtccg ggccgcggcc cccacttcca gccccggcc tggccttggc tttgaccctg | 60 |
| actatgttgg ccagacttgc atccgcggct tccttcttcg gtgagaacca cctggaggtg | 120 |
| cctgtggcca cggctctgac cgacatagac ctgcagctgc agttctccac gtcccagccc | 180 |
| gaagccctcc ttctcctggc agcagggcca gctgaccacc tcctgctgca gctctactct | 240 |
| ggacgcctgc aggtcagact tgttctgggc caggaggagc tgaggctgca gactccagca | 300 |
| gagacgctgc tgagtgactc catccccac actgtggtgc tgactgtcgt agagggctgg | 360 |
| gccacgttgt cagtcgatgg gtttctgaac gcctcctcag cagtcccagg agccccccta | 420 |
| gaggtccccc tatgggctctt tgttggggc actgggaccc ttggcctgcc ctacctgagg | 480 |
| ggaaccagcc gaccctgag gggttgcctc catgcagcca ccctcaatgg ccgcagcctc | 540 |
| ctccggcctc tgaccccga tgtgcatgag ggctgtgctg aagagttttc tgccagtgat | 600 |
| gatgtggccc tgggcttctc tgggccccac tctctggctg ccttccctgc ctggggcact | 660 |
| caggacgaag gaaccctaga gtttacactc accacacaga gccggcaggc acccttggcc | 720 |
| ttccaggcag ggggccggcg tggggacttc atctatgtgg acatatttga gggccacctg | 780 |
| cgggccgtgg tggagaaggg ccagggtacc gtattgctcc acaacagtgt gcctgtggcc | 840 |
| gatgggcagc ccatgaggt cagtgtccac atcaatgctc accggctgga aatctccgtg | 900 |
| gaccagtacc ctacgcatac ttcgaaccga ggagtcctca gctacctgga gccacggggc | 960 |
| agtctccttc tcgggggct ggatgcagag gcctctcgtc acctccagga acaccgcctg | 1020 |
| ggcctgacac cagaggccac caatgcctcc ctgctgggct gcatggaaga cctcagtgtc | 1080 |
| aatggccaga ggcgggggct gcgggaagct ttgctgacgc gcaacatggc agccggctgc | 1140 |
| aggctggagg aggaggagta tgaggacgat gcctatggac attatgaagc tttctccacc | 1200 |
| ctggcccctg aggcttggcc agccatggag ctgcctgagc catgcgtgcc tgagccaggg | 1260 |
| ctgcctcctg tctttgccaa tttcacccag ctgctgacta tcagcccact ggtggtggcc | 1320 |
| gagggggca cagcctggct tgagtggagg catgtgcagc ccacgctgga cctgatggag | 1380 |
| gctgagctgc gcaaatccca ggtgctgttc agcgtgaccc gaggggcacg ccatggcgag | 1440 |
| ctcgagctgg acatcccggg agcccaggca cgaaaaatgt tcacccctcct ggacgtggtg | 1500 |

```
aaccgcaagg cccgcttcat ccacgatggc tctgaggaca cctccgacca gctggtgctg   1560
gaggtgtcgg tgacggctcg ggtgcccatg ccctcatgcc ttcggagggg ccaaacatac   1620
ctcctgccca tccaggtcaa ccctgtcaat gacccacccc acatcatctt cccacatggc   1680
agcctcatgg tgatcctgga acacacgcag aagccgctgg ggcctgaggt tttccaggcc   1740
tatgacccgg actctgcctg tgagggcctc accttccagg tccttggcac ctcctctggc   1800
ctccccgtgg agcgccgaga ccagcctggg agccggcga ccgagttctc ctgccgggag   1860
ttggaggccg gcagcctagt ctatgtccac cgcggtggtc ctgcacagga cttgacgttc   1920
```

<210> SEQ ID NO 12
<211> LENGTH: 4767
<212> TYPE: DNA
<213> ORGANISM: artificial
<220> FEATURE:
<223> OTHER INFORMATION: Human D1+D2

<400> SEQUENCE: 12

```
atgcagtccg ggccgcggcc cccacttcca gcccccggcc tggccttggc tttgaccctg     60
actatgttgg ccagacttgc atccgcggct tccttcttcg gtgagaacca cctggaggtg    120
cctgtggcca cggctctgac cgacatagac ctgcagctgc agttctccac gtcccagccc    180
gaagccctcc ttctcctggc agcaggccca gctgaccacc tcctgctgca gctctactct    240
ggacgcctgc aggtcagact tgttctgggc caggaggagc tgaggctgca gactccagca    300
gagacgctgc tgagtgactc catcccccac actgtggtgc tgactgtcgt agagggctgg    360
gccacgttgt cagtcgatgg gtttctgaac gcctcctcag cagtcccagg agccccccta    420 gaggtccccct atgggctctt tgttgggggc actgggaccc ttggcctgcc ctacctgagg    480
ggaaccagcc gaccctgag gggttgcctc catgcagcca cctcaatgg ccgcagcctc    540 ctccggcctc tgaccccga tgtgcatgag ggctgtgctg aagagttttc tgccagtgat    600
gatgtggccc tgggcttctc tgggccccac tctctggctg ccttccctgc ctggggcact    660
caggacgaag gaaccctaga gtttacactc accacacaga gccggcaggc acccttggcc    720
ttccaggcag ggggccggcg tggggacttc atctatgtgg acatatttga gggccacctg    780
cgggccgtgg tggagaaggg ccagggtacc gtattgctcc acaacagtgt gcctgtggcc    840
gatgggcagc cccatgaggt cagtgtccac atcaatgctc accggctgga aatctccgtg    900
gaccagtacc ctacgcatac ttcgaaccga ggagtcctca gctacctgga gccacggggc    960
agtctccttc tcggggggct ggatgcagag gcctctcgtc acctccagga acaccgcctg   1020
ggcctgacac cagaggccac caatgcctcc ctgctgggct gcatggaaga cctcagtgtc   1080
aatggccaga ggcgggggct gcgggaagct ttgctgacgc gcaacatggc agccggctgc   1140
aggctggagg aggaggagta tgaggacgat gcctatggac attatgaagc tttctccacc   1200
ctggcccctg aggcttggcc agccatggag ctgcctgagc catgcgtgcc tgagccaggg   1260
ctgcctcctg tctttgccaa tttcacccag ctgctgacta tcagcccact ggtggtggcc   1320 gagggggca cagcctggct tgagtggagg catgtgcagc ccacgctgga cctgatggag   1380
gctgagctgc gcaaatccca ggtgctgttc agcgtgaccc gaggggcacg ccatggcgag   1440
ctcgagctgg acatcccggg agcccaggca cgaaaaatgt tcacccctcct ggacgtggtg   1500 aaccgcaagg cccgcttcat ccacgatggc tctgaggaca cctccgacca gctggtgctg   1560
gaggtgtcgg tgacggctcg ggtgcccatg ccctcatgcc ttcggagggg ccaaacatac   1620
```

```
ctcctgccca tccaggtcaa ccctgtcaat gacccacccc acatcatctt cccacatggc    1680
agcctcatgg tgatcctgga acacacgcag aagccgctgg ggcctgaggt tttccaggcc    1740
tatgacccgg actctgcctg tgagggcctc accttccagg tccttggcac ctcctctggc    1800
ctccccgtgg agcgccgaga ccagcctggg gagccggcga ccgagttctc ctgccgggag    1860
ttggaggccg gcagcctagt ctatgtccac cgcggtggtc ctgcacagga cttgacgttc    1920
cgggtcagcg atggactgca ggccagcccc ccggccacgc tgaaggtggt ggccatccgg    1980
ccggccatac agatccaccg cagcacaggg ttgcgactgg cccaaggctc tgccatgccc    2040
atcttgcccg ccaacctgtc ggtggagacc aatgccgtgg ggcaggatgt gagcgtgctg    2100
ttccgcgtca ctggggccct gcagtttggg gagctgcaga agcaggggc aggtgggtg     2160
gagggtgctg agtggtgggc cacacaggcg ttccaccagc gggatgtgga gcagggccgc    2220
gtgaggtacc tgagcactga cccacagcac cacgcttacg acaccgtgga gaacctggcc    2280
ctggaggtgc aggtgggcca ggagatcctg agcaatctgt ccttcccagt gaccatccag    2340
agagccactg tgtggatgct gcggctggag ccactgcaca ctcagaacac ccagcaggag    2400
accctcacca cagcccacct ggaggccacc ctggaggagg caggcccaag cccccaacc    2460
ttccattatg aggtggttca ggctcccagg aaaggcaacc ttcaactaca gggcacaagg    2520
ctgtcagatg ccagggcttc acccaggat gacatacagg ctggccgggt gacctatggg    2580
gccacagcac gtgcctcaga ggcagtcgag gacaccttcc gtttccgtgt cacagctcca    2640
ccatatttct ccccactcta taccttcccc atccacattg gtggtgaccc agatgcgcct    2700
gtcctcacca atgtcctcct cgtggtgcct gagggtggtg agggtgtcct ctctgctgac    2760
cacctctttg tcaagagtct caacagtgcc agctacctct atgaggtcat ggagcggccc    2820
cgccatggga ggttggcttg gcgtgggaca caggacaaga ccactatggt gacatccttc    2880
accaatgaag acctgttgcg tggccggctg gtctaccagc atgatgactc cgagaccaca    2940
gaagatgata tcccatttgt tgctacccgc cagggcgaga gcagtggtga catggcctgg    3000
gaggaggtac ggggtgtctt ccgagtggcc atccagcccg tgaatgacca cgccctgtg    3060
cagaccatca gccggatctt ccatgtgccc cggggtgggc ggcggctgct gactacagac    3120
gacgtggcct tcagcgatgc tgactcgggc tttgctgacg cccagctggt gcttacccgc    3180
aaggacctcc tctttggcag tatcgtggcc gtagatgagc ccacgcggcc catctaccgc    3240
ttcacccagg aggacctcag gaagaggcga gtactgttcg tgcactcagg ggctgaccgt    3300
ggctggatcc agctgcaggt gtccgacggg caacaccagg ccactgcgct gctggaggtg    3360
caggcctcgg aaccctacct ccgtgtggcc aacggctcca gccttgtggt ccctcaagga    3420
ggccagggca ccatcgacac ggccgtgctc cacctggaca ccaacctcga catccgcagt    3480
ggggatgagg tccactacca cgtcacagct ggccctcgct ggggacagct agtccgggct    3540
ggtcagccag ccacagcctt ctcccagcag gacctgctgg atggggccgt tctctatagc    3600
cacaatggca gcctcagccc ccgcgacacc atggccttct ccgtggaagc agggccagtg    3660
cacacggatg ccaccctaca agtgaccatt gccctagagg gcccactggc cccactgaag    3720
ctggtccggc acaagaagat ctacgtcttc caggagagg cagctgagat cagaagggac    3780
cagctggagg cagcccagga ggcagtgcca cctgcagaca tcgtattctc agtgaagagc    3840
ccaccgagtg ccggctacct ggtgatggtg tcgcgtggcg ccttggcaga tgagccaccc    3900
agcctggacc ctgtgcagag cttctcccag gaggcagtgg acacaggcag ggtcctgtac    3960
ctgcactccc gccctgaggc ctggagcgat gccttctcgc tggatgtggc ctcaggcctg    4020
```

```
ggtgctcccc tcgagggcgt ccttgtggag ctggaggtgc tgcccgctgc catcccacta    4080
gaggcgcaaa acttcagcgt ccctgagggt ggcagcctca ccctggcccc tccactgctc    4140
cgtgtctccg ggccctactt ccccactctc ctgggcctca gcctgcaggt gctggagcca    4200
ccccagcatg gagccctgca gaaggaggac ggacctcaag ccaggaccct cagcgccttc    4260
tcctggagaa tggtggaaga gcagctgatc cgctacgtgc atgacgggag cgagacactg    4320
acagacagtt ttgtcctgat ggctaatgcc tccgagatgg atcgcagag ccatcctgtg    4380 gccttcactg tcactgtcct gcctgtcaat gaccaacccc ccatcctcac tacaaacaca    4440
ggcctgcaga tgtgggaggg ggccactgcg cccatccctg cggaggctct gaggagcacg    4500
gacggcgact ctgggtctga ggatctggtc tacaccatcg agcagccag caacgggcgg    4560 gtagtgctgc ggggggcgcc gggcactgag gtgcgcagct tcacgcaggc ccagctggac    4620
ggcgggctcg tgctgttctc acacagagga accctggatg gaggcttccg cttccgcctc    4680
tctgacggcg agcacacttc ccccggacac ttcttccgag tgacggccca gaagcaagtg    4740
ctcctctcgc tgaagggcag ccagaca                                        4767
```

<210> SEQ ID NO 13
<211> LENGTH: 1965
<212> TYPE: DNA
<213> ORGANISM: artificial
<220> FEATURE:
<223> OTHER INFORMATION: Dog D1

<400> SEQUENCE: 13

```
atgggctccc cgcgctccgg ctccgcccgg ccccgccgac ctgccgcgat gcggggtcag      60
ccgcccgcgc ccccgggccc cgcgctgccc ctggccttgg ccttggctct gtgggcctgc    120
gccgcctccg cggcctcctt ctttggggag aaccacctgc aggtgccggt gaccacagct    180
ctgagcaaca tagacctccg gctacaattc tccacgtccc agcccgaagc cctgctcctc    240
ctggcagcag gccaggctga ccacctcctc ctgcagctcc actccggata cctgcaggtc    300
agactcaccc tgggccagga ggagctgagg ctgcagaccc cagctgagac tccgctgagc    360
gactccgccg tccactccgt ggagctgact gtgtcagaca gcgaggcctc gttgtccgtc    420
gatgggctgc tgaacgcctc agccccgtc ctgggagctc ccctggaggt cccctatggg    480
atcttcctgg ggggcactgg gagcctgagc ctgtcctacc tgatgggagc cagccggccc    540
ctgagggcgt gcctgcacgc cgccaccgtc aacggccgca acctcctccg accactgacc    600
cctgacgtgc acgagggctg cgctgaagag ttttctgctg atgacagcgt ggctctgggc    660
ttctctgggc cccactcgct ggctgccttc cctgcctgga cactcgggga ggagggcacc    720
ctggcgttca tactcaccac tcggagccga caggcgcccc tggctttcca ggcgggcggc    780
cggcacgggg atttcatcta cgtggacata tttgagggcc acctgcgggc tgtggtggag    840
aagggccagg gcaccgtgtt gctccacaac agcgtgcccg tggctgacgg gctaccccat    900
gaggtcagtg tccacgtgga tgctcaccag ctggaaatct ccgtggacca gtacccacaa    960
cggacttcca accgtgggat cctcagctac ctgaaccccc gcggcagtct cctcctgggg    1020
gggctggaca cagaggcctc ccgccacctc aggaacacc gctgggcct ggcctcgggg    1080 gccgtcaacg tctccctcct gggctgcatg gaggatctca gcatcaacgg ccagaggcag    1140
gggctccggg aagcctcgct gactcgcagc atggtggccg gctgcagcct ggaggaagac    1200
gagtacgagg aggacaccta cggcacctat gaagctctct ccaccctggc accggaggcc    1260
```

-continued

| | |
|---|---|
| tggtccgccg tggagctgcc cgagccctgc gtgcccgaac cggggctgcc tcccgtcttt | 1320 |
| gccaacttca cccaactgct gactgtcagc ccgctggtgg tggccgaggg gggcacagcc | 1380 |
| tggcttgagt ggcggcacct gcagcccacg ctggacctga gcgaggccga gctgcgtaaa | 1440 |
| tcccaggtgc tgttcagcgt gagccgtggg gcccgccacg gggagctcga gctggacgtc | 1500 |
| ccgggagccc aggcacggaa aatgttcacc ctcctggacg tggtgaaccg caaggcccgc | 1560 |
| ttcgtccacg atggctcgga ggagacctcc gaccagctga tgctggaggt gtccgtgacc | 1620 |
| gccaggggcc ctgtgccctc ctgcctccgg aggggccaga cttacatcct gcccatccag | 1680 |
| ataaacccgg tcaacgaccc accccaaatc atcttccccc acggcagcct catggtgatc | 1740 |
| ctggaacaca cacagaagcc cctggggccc gaggtcttcc aggcctacga cccagactct | 1800 |
| gcctgcgagg gcctcacctt ccagctcctt ggcaccgccc cgggcctgcc ggtggagcgc | 1860 |
| caggagcagc ccggggagcc agccaccgag ttctcctgcc gggagctgga ggcgggcggc | 1920 |
| ctggtctacg tgcaccggag cgggcccgcc caggacctga cgttc | 1965 |

<210> SEQ ID NO 14
<211> LENGTH: 4815
<212> TYPE: DNA
<213> ORGANISM: artificial
<220> FEATURE:
<223> OTHER INFORMATION: Dog D1+D2

<400> SEQUENCE: 14

| | |
|---|---|
| atgggctccc cgcgctccgg ctccgcccgg ccccgccgac ctgccgcgat gcggggtcag | 60 |
| ccgcccgcgc ccccgggccc cgcgctgccc tggccttgg ccttggctct gtgggcctgc | 120 |
| gccgcctccg cggcctcctt ctttggggag aaccacctgc aggtgccggt gaccacagct | 180 |
| ctgagcaaca tagacctccg gctacaattc tccacgtccc agcccgaagc cctgctcctc | 240 |
| ctggcagcag gccaggctga ccacctcctc ctgcagctcc actccggata cctgcaggtc | 300 |
| agactcaccc tgggccagga ggagctgagg ctgcagaccc cagctgagac tccgctgagc | 360 |
| gactccgccg tccactccgt ggagctgact gtgtcagaca gcgaggcctc gttgtccgtc | 420 |
| gatgggctgc tgaacgcctc agcccccgtc ctggagctcc ccctggaggt ccccatatggg | 480 |
| atcttcctgg ggggcactgg gagcctgagc ctgtcctacc tgatgggagc cagccggccc | 540 |
| ctgaggggct gcctgcacgc cgccaccgtc aacggccgca acctcctccg accactgacc | 600 |
| cctgacgtgc acgagggctg cgctgaagag ttttctgctg atgacagcgt ggctctgggc | 660 |
| ttctctgggc cccactcgct ggctgccttc cctgcctgga cactcgggga ggagggcacc | 720 |
| ctggcgttca tactcaccac tcggagccga caggcgcccc tggctttcca ggcgggcggc | 780 |
| cggcacgggg atttcatcta cgtggacata tttgagggcc acctgcgggc tgtggtggag | 840 |
| aagggccagg gcaccgtgtt gctccacaac agcgtgcccg tggctgacgg gctacccat | 900 |
| gaggtcagtg tccacgtgga tgctcaccag ctggaaatct ccgtggacca gtaccccaca | 960 |
| cggacttcca accgtgggat cctcagctac ctggaacccc gcggcagtct cctcctgggg | 1020 |
| gggctggaca cagaggcctc ccgccacctc caggaacacc gcctgggcct ggcctcgggg | 1080 |
| gccgtcaacg tctccctcct gggctgcatg gaggatctca gcatcaacgg ccagaggcag | 1140 |
| gggctccggg aagcctcgct gactcgcagc atggtggccg gctgcagcct ggaggaagac | 1200 |
| gagtacgagg aggacaccta cggcaccatat gaagctctct ccaccctggc accggaggcc | 1260 |
| tggtccgccg tggagctgcc cgagccctgc gtgcccgaac cggggctgcc tcccgtcttt | 1320 |
| gccaacttca cccaactgct gactgtcagc ccgctggtgg tggccgaggg gggcacagcc | 1380 |

-continued

```
tggcttgagt ggcggcacct gcagcccacg ctggacctga gcgaggccga gctgcgtaaa      1440
tcccaggtgc tgttcagcgt gagccgtggg gcccgcacg gggagctcga gctggacgtc       1500
ccgggagccc aggcacggaa aatgttcacc ctcctggacg tggtgaaccg caaggcccgc      1560
ttcgtccacg atggctcgga ggagacctcc gaccagctga tgctggaggt gtccgtgacc      1620
gccaggggcc ctgtgccctc ctgcctccgg aggggccaga cttacatcct gcccatccag      1680
ataaacccgg tcaacgaccc accccaaatc atcttccccc acggcagcct catggtgatc      1740
ctggaacaca cacagaagcc cctggggccc gaggtcttcc aggcctacga cccagactct      1800
gcctgcgagg gcctcacctt ccagctcctt ggcaccgccc cgggcctgcc ggtgagcgc       1860 caggagcagc ccggggagcc agccaccgag ttctcctgcc gggagctgga ggcgggcggc      1920
ctggtctacg tgcaccggag cgggcccgcc caggacctga cgttccgcgt cagcgacggg      1980
ctgcaggcca gcgctccggc cacgctgcag gtggtggcgg tccggcccag catccgggtc      2040
cgccacaaca cggggctgcg cctggcccag ggctccgccg ccccggtgct gcccgccaat      2100
ctgtcggtgg agaccaacgc ggtggggcag gatgtgagcg tgctgttccg ggtcgccgcg      2160 gccctgcgt tcggggagct gcagaagcag ggcgcggggg gcgccgaggg cgcggagtgg       2220
cgcccggtgc aggccttcca gcagcgggac gtggagcagg gccgcgtgag gtacctgagc      2280
accgaccccg cagcaccgca cggaggacgcc gtggagcgcg tggccctgga ggttcaggtg     2340
ggccaggaga ccctgagcaa tctgtccttc ctggtgacga tccagagagc caccgtgcgg     2400
ctgctgcggc tcgagcccct gcgcacccac accacgcggc aggaggcgct caccggcgcg    2460
cacctggagg ccgctctgga ggagggggcg ggccccagcc ccaccacctt ccactacgag    2520
ctggttcagg cccccaggaa gggtaacctc aggctgcagg gcgcccggct gtccgagggg    2580
cagggcttca cccaggatga cctgcaggcc ggccgggtga cctacggggc cacggcgcgc   2640
acctcggaga ccgtggagga cgccttccgt ttccgcgtca cggctccgcc acatttctcc    2700
ccgctctaca ccttccccat ccacatcggg ggtgaccccg acgcccccgt cctcaccaac    2760
gtcctcctct ccgtgcccga gggaggcgag ggcgtcctct ccgcggaaca cctgttcgtc    2820
aagagcctca acagcgccag ctacctctat gaggtcatgg agcggcccg ccacgggcgg     2880 ctggtctgga ggggggcgca ggacgaggcc accgcggtga cgtccttcac caacgaggac    2940
ctgctgcagg ccggctggt ctaccagcat gacaactccg agaccacgga agacgacatc     3000
cccttcgtgg caacccgcca gagtgagggc agcggcggcc tggcctggga ggaggtccgg    3060
ggcgtcttcc gcgtggccat ccagcccgtg aacgaccacg ctcccgtgca gaccgtcagc    3120
cgcgtcttcc acgtggcccg gggcgggcgg cggctgctga cgaccgacga cgtggccttc    3180
agtgacgcca actccggctt cgccgacgcg cagctggtgc tgacccgcaa ggaccttctc    3240
ttcggcagca tcgtggccgc ggacgagccc acgcggccca tctaccgctt ctcccaggag    3300
gacctccgga gaggcgcgt cctgttcgtg cactccgggg ccgaccgcgg ctggatccag    3360
ctgcaggtgt ccgacgggcg gcaccaggcc accgcgctgc ttgaagtgca ggcatccgag   3420
ccctatctcc gcgtggccaa tggctccagc ctcgtggtcc ctcaggggg ccagggcacc    3480 atcgacacag ccgtgctccg cctggacacc aacctagaca ttcgcagcgg ggatgaggtc   3540
cgctaccgtg tcacagccgg cccgcactgg gggcagctgc tccgggccgg ccagccggcc   3600
acagccttct cccaacagga cctgctggac ggggccgtcc tctacagcca caacggcagc   3660
ctgagcccgc aggacaccct ggccttctcc gtggaggcag ggcctgtgct cacggatgcc   3720
```

| | |
|---|---|
| accctgcagg tgaccattgc cttggagggg ccattggccc cactgcatct ggtccagaac | 3780 |
| aagaagatct acgtcttcca gggggaggca gctgagatca gaaaggatca gctggaggca | 3840 |
| gcgcaggagg cagtgccgcc cgcccaaatt gtgttctcgg tgaagacccc gccgcgggcc | 3900 |
| ggctacctgg tgatgctgtc ccgcggcgcc tccgtggccg gccgcccag ctggaccccc | 3960 |
| gtgcagagct tctcccagga ggcggtggac gccggcaggg tcctgtacct ccactcccgc | 4020 |
| cccgaggcct ggagtgactc cttctcccta gacgtgggct caggcctggg tgcgcccctc | 4080 |
| gagggcgtcc gcgtggagct ggaggtgctg cccgccacca tcccactgga ggcacagaac | 4140 |
| ttcagcgtcc ccgagggcgg cagccgcgtg ctggcccccc cgctgctcca ggtcgccggg | 4200 |
| ccctacttcc ctgcactgcc cggcctcgaa ctgcgggtcc tcgagcagcc cctgcacggg | 4260 |
| gccctgcgga gagaggaggc ccctcaagcg gggaccctca cgctttctc ctggaaagag | 4320 |
| gtagaacagc agcagatccg ctatgtgcac gacgggagtg agacgctgac agacagcttc | 4380 |
| accctagtgg ctaacgcctc cgagctggac cgccagagcc accctgtggc cttcaccatc | 4440 |
| accgtcctgc ccgtcaatga ccaaccgccc atcctcaccg caaacacagg cctaacgatg | 4500 |
| tgggaggggg ccaccgtgcc cttccctccg gaggccctga ggggtgcgga cagcgactcg | 4560 |
| ggcccggagg acctggtcta caccatcgag cggcccagca cgggcaggt ggtgctgcgg | 4620 |
| gcggcgccag gcaccgaggt gcacagcttc acgcaggccc agctggacga cgggctcgtg | 4680 |
| ctgttctcac acagaggagc cctggacgga ggcttccgct tcagcctgtc cgacggcgag | 4740 |
| cacgcttccc ccggacactt cttccgcgtg acggcccaga agcagctgct cctctccctg | 4800 |
| gagggcagcc ggacg | 4815 |

<210> SEQ ID NO 15
<211> LENGTH: 3737
<212> TYPE: DNA
<213> ORGANISM: artificial
<220> FEATURE:
<223> OTHER INFORMATION: HuDo Hu

<400> SEQUENCE: 15

| | |
|---|---|
| atgcagtccg ggccgcggcc cccacttcca gcccccggcc tggccttggc tttgaccctg | 60 |
| actatgttgg ccagacttgc atccgcggct tccttcttcg gtgagaacca cctggaggtg | 120 |
| cctgtggcca cggctctgac cgacatagac ctgcagctgc agttctccac gtcccagccc | 180 |
| gaagccctcc ttctcctggc agcaggccca gctgaccacc tcctgctgca gctctactct | 240 |
| ggacgcctgc aggtcagact tgttctgggc caggaggagc tgaggctgca gactccagca | 300 |
| gagacgctgc tgagtgactc catccccac actgtggtgc tgactgtcgt agagggctgg | 360 |
| gccacgttgt cagtcgatgg gtttctgaac gcctcctcag cagtcccagg agcccccta | 420 |
| gaggtcccct atgggctctt tgttggggc actgggaccc ttggcctgcc ctacctgagg | 480 |
| ggaaccagcc gaccctgag gggttgcctc catgcagcca cctcaatgg ccgcagcctc | 540 |
| ctccggcctc tgacccccga tgtgcatgag ggctgtgctg aagagttttc tgccagtgat | 600 |
| gatgtggccc tggcttctc tgggccccac tctctggctg ccttccctgc ctggggcact | 660 |
| caggacgaag gaaccctaga gtttacactc accacacaga gccggcaggc acccttggcc | 720 |
| ttccaggcag ggggccggcg tggggacttc atctatgtgg acatatttga gggccacctg | 780 |
| cgggccgtgg tggagaaggg ccagggtacc gtattgctcc acaacagtgt gcctgtggcc | 840 |
| gatgggcagc cccatgaggt cagtgtccac atcaatgctc accggctgga aatctccgtg | 900 |
| gaccagtacc ctacgcatac ttcgaaccga ggagtcctca gctacctgga gccacggggc | 960 |

```
agtctccttc tcgggggggct ggatgcagag gcctctcgtc acctccagga acaccgcctg    1020
ggcctgacac cagaggccac caatgcctcc ctgctgggct gcatggaaga cctcagtgtc    1080
aatggccaga ggcgggggct gcgggaagct ttgctgacgc gcaacatggc agccggctgc    1140
aggctggagg aggaggagta tgaggacgat gcctatggac attatgaagc tttctccacc    1200
ctggcccctg aggcttggcc agccatggag ctgcctgagc catgcgtgcc tgagccaggg    1260
ctgcctcctg tctttgccaa tttcacccag ctgctgacta tcagcccact ggtggtggcc    1320 gagggggca  cagcctggct tgagtggagg catgtgcagc ccacgctgga cctgatggag    1380
gctgagctgc gcaaatccca ggtgctgttc agcgtgaccc gaggggcacg ccatggcgag    1440
ctcgagctgg acatcccggg agcccaggca cgaaaaatgt tcaccctcct ggacgtggtg    1500
aaccgcaagg cccgcttcat ccacgatggc tctgaggaca cctccgacca gctggtgctg    1560
gaggtgtcgg tgacggctcg ggtgcccatg ccctcatgcc ttcggagggg ccaaacatac    1620
ctcctgccca tccaggtcaa ccctgtcaat gacccacccc acatcatctt cccacatggc    1680
agcctcatgg tgatcctgga acacacgcag aagccgctgg ggcctgaggt tttccaggcc    1740 tatgacccg  actctgcctg tgagggcctc accttccagg tccttggcac ctcctctggc    1800
ctccccgtgg agcgccgaga ccagcctggg gagccggcga ccgagttctc ctgccgggag    1860
ttggaggccg gcagcctagt ctatgtccac cgcggtggtc ctgcacagga cttgacgttc    1920
cgggtcagcg atggactgca ggccagcccc ccggccacgc tgaaggtggt ggccatccgg    1980
ccggccatac agatccaccg cagcacaggg ttgcgactgg cccaaggctc tgccatgccc    2040
atcttgcccg ccaacctgtc ggtggagacc aatgccgtgg ggcaggatgt gagcgtgctg    2100
ttccgcgtca ctgggccct  gcagtttggg gagctgcaga agcaggggc  aggtgggtg    2160 gagggtgctg agtggtgggc cacacaggcg ttccaccagc gggatgtgga gcagggccgc    2220
gtgaggtacc tgagcactga cccacagcac cacgcttacg acaccgtgga gaacctggcc    2280
ctggaggtgc aggtgggcca ggagatcctg agcaatctgt ccttcccagt gaccatccag    2340
agagccactg tgtggatgct gcggctggag ccactgcaca ctcagaacac ccagcaggag    2400
accctcacca cagcccacct ggaggccacc ctggaggagg caggcccaag ccccccaacc    2460
ttccattatg aggtggttca ggctcccagg aaaggcaacc ttcaactaca gggcacaagg    2520
ctgtcagatg gccagggctt cacccaggat gacatacagg ctggccgggt gacctatggg    2580
gccacagcac gtgcctcaga ggcagtcgag gacaccttcc gtttccgtgt cacagctcca    2640
ccatatttct ccccactcta taccttcccc atccacattg tggtgaccc  agatgcgcct    2700 gtcctcacca atgtcctcct cgtggtgcct gagggtggtg agggtgtcct ctctgctgac    2760
cacctctttg tcaagagtct caacagtgcc agctacctct atgaggtcat ggagcggccc    2820
cgccatggga ggttggcttg gcgtgggaca caggacaaga ccactatggt gacatccttc    2880
accaatgaag acctgttgcg tggccggctg gtctaccagc atgatgactc cgagaccaca    2940
gaagatgata tcccatttgt tgctacccgc cagggcgaga gcagtggtga catggcctgg    3000
gaggaggtac ggggtgtctt ccgagtggcc atccagcccg tgaatgacca cgcccctgtg    3060
cagaccatca gccggatctt ccatgtgccc cggggtgggc ggcggctgct gactacagac    3120
gacgtggcct tcagcgatgc tgactcgggc tttgctgacg cccagctggt gcttacccgc    3180
aaggacctcc tctttggcag tatcgtggcc gtagatgagc ccacgcggcc catctaccgc    3240
ttcacccagg aggacctcag gaagaggcga gtactgttcg tgcactcagg ggctgaccgt    3300
```

| | |
|---|---|
| ggctggatcc agctgcaggt gtccgacggg caacaccagg ccactgcgct gctggaggtg | 3360 |
| caggcctcgg aaccctacct ccgtgtggcc aacggctcca gccttgtggt ccctcaagga | 3420 |
| ggccagggca ccatcgacac ggccgtgctc cacctggaca ccaacctcga catccgcagt | 3480 |
| ggggatgagg tccactacca cgtcacagct ggccctcgct ggggacagct agtccgggct | 3540 |
| ggtcagccag ccacagcctt ctcccagcag gacctgctgg atggggccgt tctctatagc | 3600 |
| cacaatggca gcctcagccc ccgcgacacc atggccttct ccgtggaagc agggccagtg | 3660 |
| cacacggatg ccaccctaca agtgaccatt gccctagagg gcccactggc cccactgaag | 3720 |
| ctggtccggc acaagaa | 3737 |

<210> SEQ ID NO 16
<211> LENGTH: 5018
<212> TYPE: DNA
<213> ORGANISM: artificial
<220> FEATURE:
<223> OTHER INFORMATION: DoHu Dog

<400> SEQUENCE: 16

| | |
|---|---|
| atggccctcg gtgctctgca gagctgctcc atccgccact cagagtccca gggaccccct | 60 |
| ccttcaaagt gtcggggcct gggtgatggg ctgggcctct ggagaggtgg gcaggggcca | 120 |
| tctgaggtga ccagagtggg ccatttgggc agcctgcagg ctccagccga gcgattccag | 180 |
| cacccgctct ccttgggctt cgacgggaac ccactctcca atatcttctc agcatccacg | 240 |
| ctgtacgagc attggcggga caggagggtc ttctggtgct gccgcctggg gccgggtggc | 300 |
| caggtgggcc aggctgctgg cgaggttgcg ggaggggagc gggtgcgcat ggagctctca | 360 |
| gaggaagtgc acaggctgct tctgggaact gggcgtgctg cccaggaggg gcaggcaggg | 420 |
| gaggggggttg gaagagcccg ccgcacaccc tcactggcgc acacagatgt gggtgtgcgc | 480 |
| acaagtatga caaccgcga gcaggtgccc aaggggccct cgggcctggg cctgctcctg | 540 |
| ctccccccagc tcctggctcc acccagctcc cctcttgcct ccaacatgcc ccctgcccca | 600 |
| accctgggca ttcggggcga gccgtgtcc cacgggcggc cgaggagctc ggccatcagg | 660 |
| cctttctgcc aaagccgtga cctccgtcag cgtgatgccc gggaggtaca cgtacgcaca | 720 |
| tgcgtgcaca cgcgcgtgca agtgttgctc agcagcctgg cccagagcct agcaaggaga | 780 |
| gcgcccagcc cctcagcagc catcccggga gaaaccccg actcaggatt cacgcccccc | 840 |
| agcaccacgg ccaggggcct tgggggcatt ggcaagaggg cccaggaccc cggagagttg | 900 |
| gtgctggaga cagagacgtg ggggcaggtg gttcaggggt tagagccagc cagcgccttc | 960 |
| acttccggcc tggtacgggc cctgaggccc tatgacgatg tccctgcatc cagcttcaac | 1020 |
| agagggagt ctacagaccc aggctgggaa aagccagctg tagtcggcta tggctccccca | 1080 |
| gccatcgtgg gaacaacagg gccggatctg actgcccccc agggacaatc agcagccttg | 1140 |
| cggcaggaag caatacggcg tgatgcagga agctggggcc catttggggt ccagtacgtg | 1200 |
| gtctccatct ggcctcagcg ccttcgctct ttggtggact cgggctggcg actgcaccct | 1260 |
| tactccaaag acagctggga gagaagtgag ggggcagtgc cagccaggac cgtgaagctg | 1320 |
| cgccagcaca aaacccgcat cgtccgcagc acctctcctc ctccagcctc cttctttggg | 1380 |
| gagaaccacc tgcaggtgcc ggtgaccaca gctctgagca acatagacct ccggctacaa | 1440 |
| ttctccacgt cccagcccga agccctgctc ctcctggcag caggccaggc tgaccacctc | 1500 |
| ctcctgcagc tccactccgg atacctgcag gtcagactca ccctgggcca ggaggagctg | 1560 |
| aggctgcaga ccccagctga gactccgctg agcgactccg ccgtccactc cgtggagctg | 1620 |

```
actgtgtcag acagcgaggc ctcgttgtcc gtcgatgggc tgctgaacgc ctcagccccc    1680
gtcctgggag ctcccctgga ggtcccctat gggatcttcc tgggggggcac tgggagcctg    1740
agcctgtcct acctgatggg agccagccgg cccctgaggg gctgcctgca cgccgccacc    1800
gtcaacggcc gcaacctcct ccgaccactg acccctgacg tgcacgaggg ctgcgctgaa    1860
gagttttctg ctgatgacag cgtggctctg gcttctctg ggcccactc gctggctgcc    1920
ttccctgcct ggaacactcg ggaggagggc accctggcgt tcatactcac cactcggagc    1980
cgacaggcgc ccctggcttt ccaggcgggc ggccggcacg gggatttcat ctacgtggac    2040
atatttgagg ccacctgcg ggctgtggtg gagaagggcc agggcaccgt gttgctccac    2100
aacagcgtgc ccgtggctga cgggctaccc catgaggtca gtgtccacgt ggatgctcac    2160
cagctggaaa tctccgtgga ccagtacccc acacggactt ccaaccgtgg gatcctcagc    2220
tacctggaac cccgcggcag tctcctcctg ggggggctgg acacagaggc ctcccgccac    2280
ctccaggaac accgcctggg cctggcctcg ggggccgtca acgtctccct cctgggctgc    2340
atggaggatc tcagcatcaa cggccagagg caggggctcc gggaagcctc gctgactcgc    2400
agcatggtgg ccggctgcag cctggaggaa gacgagtacg aggaggacac ctacggcacc    2460
tatgaagctc tctccaccct ggcaccggag gcctggtccg ccgtggagct gcccgagccc    2520
tgcgtgcccg aaccggggct gcctcccgtc tttgccaact tcaccaact gctgactgtc    2580
agcccgctgg tggtggccga ggggggcaca gcctggcttg agtggcggca cctgcagccc    2640
acgctggacc tgagcgaggc cgagctgcgt aaatcccagg tgctgttcag cgtgagccgt    2700
ggggccccgcc acggggagct cgagctggac gtcccgggag cccaggcacg gaaaatgttc    2760
accctcctgg acgtggtgaa ccgcaaggcc cgcttcgtcc acgatggctc ggaggagacc    2820
tccgaccagc tgatgctgga ggtgtccgtg accgccaggg gccctgtgcc ctcctgcctc    2880
cggaggggcc agacttacat cctgcccatc cagataaacc cggtcaacga cccacccaa    2940
atcatcttcc cccacggcag cctcatggtg atcctggaac acacacagaa gcccctgggg    3000
cccgaggtct tccaggccta cgacccagac tctgcctgcg agggcctcac cttccagctc    3060
cttggcaccg ccccgggcct gccggtgag cgccaggagc agcccgggga ccagccacc    3120
gagttctcct gccgggagct ggaggcgggc ggcctggtct acgtgcaccg gagcgggccc    3180
gcccaggacc tgacgttccg cgtcagcgac gggctgcagg ccagcgctcc ggccacgctg    3240
caggtggtgg cggtccggcc cagcatccgg gtccgccaca acacggggct gcgcctggcc    3300
cagggctccg ccgccccggt gctgcccgcc aatctgtcgg tggagaccaa cgcggtgggg    3360
caggatgtga gcgtgctgtt ccgggtcgcc gcggccctgc ggttcgggga gctgcagaag    3420
cagggcgcgg gggcgccga gggcgcggag tggcgcccgg tgcaggcctt ccagcagcgg    3480
gacgtggagc agggccgcgt gaggtacctg agcaccgacc cgcagcaccg cacggaggac    3540
gccgtggagc gcgtggccct ggaggttcag gtggccagg agaccctgag caatctgtcc    3600
ttcctggtga cgatccagag agccaccgtg cggctgctgc ggctcgagcc cctgcgcacc    3660
cacaccacgc ggcaggaggc gctcaccggc gcgcacctgg aggccgctct ggaggagggg    3720
gcgggcccca gccccaccac cttccactac gagctggttc aggcccccag gaagggtaac    3780
ctcaggctgc agggcgcccg gctgtccgag gggcagggct tcacccagga tgacctgcag    3840
gccgccgggg tgacctacgg ggccacggcg cgcacctcgg agaccgtgga ggacgccttc    3900
cgtttccgcg tcacggctcc gccacatttc tccccgctct acaccttccc catccacatc    3960
```

-continued

| | |
|---|---|
| gggggtgacc ccgacgcccc cgtcctcacc aacgtcctcc tctccgtgcc cgagggaggc | 4020 |
| gagggcgtcc tctccgcgga acacctgttc gtcaagagcc tcaacagcgc cagctacctc | 4080 |
| tatgaggtca tggagcggcc ccgccacggg cggctggtct ggaggggggc gcaggacgag | 4140 |
| gccaccgcgg tgacgtcctt caccaacgag gacctgctgc agggccggct ggtctaccag | 4200 |
| catgacaact ccgagaccac ggaagacgac atccccttcg tggcaacccg ccagagtgag | 4260 |
| ggcagcggcg gcctggcctg ggaggaggtc cggggcgtct tccgcgtggc catccagccc | 4320 |
| gtgaacgacc acgctcccgt gcagaccgtc agccgcgtct tccacgtggc ccggggcggg | 4380 |
| cggcggctgc tgacgaccga cgacgtggcc ttcagtgacg ccgactccgg cttcgccgac | 4440 |
| gcgcagctgg tgctgacccg caaggacctt ctcttcggca gcatcgtggc cgcggacgag | 4500 |
| cccacgcggc ccatctaccg cttctcccag gaggacctcc ggaagaggcg cgtcctgttc | 4560 |
| gtgcactccg gggccgaccg cggctggatc cagctgcagg tgtccgacgg gcggcaccag | 4620 |
| gccaccgcgc tgcttgaagt gcaggcatcc gagccctatc ccgcgtggc caatggctcc | 4680 |
| agcctcgtgg tccctcaggg ggggccaggc accatcgaca cagccgtgct ccgcctggac | 4740 |
| accaacctag acattcgcag cggggatgag gtccgctacc gtgtcacagc cggcccgcac | 4800 |
| tgggggcagc tgctccgggc cggccagccg gccacagcct tctcccaaca ggacctgctg | 4860 |
| gacggggccg tcctctacag ccacaacggc agcctgagcc cgcaggacac cctggccttc | 4920 |
| tccgtggagg cagggcctgt gctcacggat gccaccctgc aggtgaccat tgccttggag | 4980 |
| gggccattgg ccccactgca tctggtccag aacaagaa | 5018 |

<210> SEQ ID NO 17
<211> LENGTH: 3785
<212> TYPE: DNA
<213> ORGANISM: artificial
<220> FEATURE:
<223> OTHER INFORMATION: DoHux - Dog 3790

<400> SEQUENCE: 17

| | |
|---|---|
| atgggctccc cgcgctccgg ctccgcccgg ccccgccgac ctgccgcgat gcggggtcag | 60 |
| ccgcccgcgc ccccgggccc cgcgctgccc ctggccttgg ccttggctct gtgggcctgc | 120 |
| gccgcctccg cggcctcctt ctttggggag aaccacctgc aggtgccggt gaccacagct | 180 |
| ctgagcaaca tagacctccg gctacaattc tccacgtccc agcccgaagc cctgctcctc | 240 |
| ctggcagcag gccaggctga ccacctcctc ctgcagctcc actccggata cctgcaggtc | 300 |
| agactcaccc tgggccagga ggagctgagg ctgcagaccc cagctgagac tccgctgagc | 360 |
| gactccgccg tccactccgt ggagctgact gtgtcagaca gcgaggcctc gttgtccgtc | 420 |
| gatgggctgc tgaacgcctc agcccccgtc ctggagctc ccctggaggt ccccatgggg | 480 |
| atcttcctgg ggggcactgg gagcctgagc ctgtcctacc tgatgggagc cagccggccc | 540 |
| ctgagggget gcctgcacgc cgccaccgtc aacggccgca acctcctccg accactgacc | 600 |
| cctgacgtgc acgagggctg cgctgaagag tttttctgctg atgacagcgt ggctctgggc | 660 |
| ttctctgggc cccactcgct ggctgccttc cctgcctgga acactcggga ggagggcacc | 720 |
| ctggcgttca tactcaccac tcggagccga caggcgcccc tggctttcca ggcgggcggc | 780 |
| cggcacgggg atttcatcta cgtggacata tttgagggcc acctgcgggc tgtggtggag | 840 |
| aagggccagg gcaccgtgtt gctcacaac agcgtgcccg tggctgacgg gctaccccat | 900 |
| gaggtcagtg tccacgtgga tgctcaccag ctggaaatct ccgtgaccca gtaccccaca | 960 |
| cggacttcca accgtgggat cctcagctac ctggaacccc gcggcagtct cctcctgggg | 1020 |

```
gggctggaca cagaggcctc ccgccacctc caggaacacc gcctgggcct ggcctcgggg    1080
gccgtcaacg tctccctcct gggctgcatg gaggatctca gcatcaacgg ccagaggcag    1140
gggctccggg aagcctcgct gactcgcagc atggtggccg gctgcagcct ggaggaagac    1200
gagtacgagg aggacaccta cggcaccttat gaagctctct ccaccctggc accggaggcc    1260
tggtccgccg tggagctgcc cgagccctgc gtgcccgaac cggggctgcc tcccgtctttt    1320
gccaacttca cccaactgct gactgtcagc ccgctggtgg tggccgaggg gggcacagcc    1380
tggcttgagt ggcggcacct gcagcccacg ctggacctga gcgaggccga gctgcgtaaa    1440
tcccaggtgc tgttcagcgt gagccgtggg gcccgccacg gggagctcga gctggacgtc    1500
ccgggagccc aggcacggaa aatgttcacc ctcctggacg tggtgaaccg caaggcccgc    1560
ttcgtccacg atggctcgga ggagacctcc gaccagctga tgctggaggt gtccgtgacc    1620
gccaggggcc ctgtgccctc ctgcctccgg aggggccaga cttacatcct gcccatccag    1680
ataaacccgg tcaacgaccc accccaaatc atcttccccc acggcagcct catggtgatc    1740
ctggaacaca cacagaagcc cctggggccc gaggtcttcc aggcctacga cccagactct    1800
gcctgcgagg gcctcaccttt ccagctcctt ggcaccgccc cgggcctgcc ggtgagcgc     1860
caggagcagc ccggggagcc agccaccgag ttctcctgcc gggagctgga ggcgggcggc    1920
ctggtctacg tgcaccggag cgggcccgcc caggacctga cgttccgcgt cagcgacggg    1980
ctgcaggcca gcgctccggc cacgctgcag gtggtggcgg tccggcccag catccgggtc    2040
cgccacaaca cggggctgcg cctggcccag ggctccgccg ccccggtgct gcccgccaat    2100
ctgtcggtgg agaccaacgc ggtggggcag gatgtgagcg tgctgttccg ggtcgccgcg    2160
gccctgcggt tcggggagct gcagaagcag ggcgcggggg gcgccgaggg cgcggagtgg    2220
cgcccggtgc aggccttcca gcagcgggac gtggagcagg gccgcgtgag gtacctgagc    2280
accgaccccgc agcaccgcac ggaggacgcc gtggagcgcg tggccctgga ggttcaggtg    2340
ggccaggaga ccctgagcaa tctgtccttc ctggtgacga tccagagagc caccgtgcgg    2400
ctgctgcggc tcgagcccct gcgcacccac accacgcggc aggaggcgct caccggcgcg    2460
cacctggagg ccgctctgga ggaggggcg ggccccagcc ccaccacctt ccactacgag    2520
ctggttcagg cccccaggaa gggtaacctc aggctgcagg gcgcccggct gtccgagggg    2580
cagggcttca cccaggatga cctgcaggcc ggccgggtga cctacgggc cacggcgcgc    2640
acctcggaga ccgtggagga cgccttccgt ttccgcgtca cggctccgcc acatttctcc    2700
ccgctctaca ccttccccat ccacatcggg ggtgaccccg acgcccccgt cctcaccaac    2760
gtcctcctct ccgtgcccga gggaggcgag ggcgtcctct ccgcggaaca cctgttcgtc    2820
aagagcctca acagcgccag ctacctctat gaggtcatgg agcggcccg ccacgggcgg    2880
ctggtctgga ggggggcgca ggacgaggcc accgcggtga cgtccttcac caacgaggac    2940
ctgctgcagg gccggctggt ctaccagcat gacaactccg agaccaccgga agacgacatc    3000
cccttcgtgg caacccgcca gagtgagggc agcggcggcc tggcctggga ggaggtccgg    3060
ggcgtcttcc gcgtggccat ccagcccgtg aacgaccacg ctcccgtgca gaccgtcagc    3120
cgcgtcttcc acgtggcccg gggcgggcgg cggctgctga cgaccgacga cgtggccttc    3180
agtgacgccg actccggctt cgccgacgcg cagctggtgc tgacccgcaa ggaccttctc    3240
ttcggcagca tcgtggccgc ggacgagccc acgcggccca tctaccgctt ctcccaggag    3300
gacctccgga agaggcgcgt cctgttcgtg cactccgggg ccgaccgcgg ctggatccag    3360
```

| | |
|---|---|
| ctgcaggtgt ccgacgggcg gcaccaggcc accgcgctgc ttgaagtgca ggcatccgag | 3420 |
| ccctatctcc gcgtggccaa tggctccagc ctcgtggtcc ctcaggggggg ccagggcacc | 3480 |
| atcgacacag ccgtgctccg cctggacacc aacctagaca ttcgcagcgg ggatgaggtc | 3540 |
| cgctaccgtg tcacagccgg cccgcactgg gggcagctgc tccgggccgg ccagccggcc | 3600 |
| acagccttct cccaacagga cctgctggac ggggccgtcc tctacagcca caacggcagc | 3660 |
| ctgagcccgc aggacaccct ggccttctcc gtggaggcag ggcctgtgct cacgcgatgcc | 3720 |
| accctgcagg tgaccattgc cttggagggg ccattggccc cactgcatct ggtccagaac | 3780 |
| aagaa | 3785 |

<210> SEQ ID NO 18
<211> LENGTH: 5007
<212> TYPE: DNA
<213> ORGANISM: artificial
<220> FEATURE:
<223> OTHER INFORMATION: Dog D2+D3

<400> SEQUENCE: 18

| | |
|---|---|
| cgcgtcagcg acgggctgca ggccagcgct ccggccacgc tgcaggtggt ggcggtccgg | 60 |
| cccagcatcc gggtccgcca caacgggg ctgcgcctgg cccagggctc cgccgccccg | 120 |
| gtgctgcccg ccaatctgtc ggtggagacc aacgcggtgg ggcaggatgt gagcgtgctg | 180 |
| ttccgggtcg ccgcggccct gcggttcggg agctgcaga agcagggcgc ggggggcgcc | 240 |
| gagggcgcgg agtggcgccc ggtgcaggcc ttccagcagc gggacgtgga gcagggccgc | 300 |
| gtgaggtacc tgagcaccga cccgcagcac cgcacggagg acgccgtgga gcgcgtggcc | 360 |
| ctggaggttc aggtgggcca ggagaccctg agcaatctgt ccttcctggt gacgatccag | 420 |
| agagccaccg tgcggctgct gcggctcgag cccctgcgca cccacaccac gcggcaggag | 480 |
| gcgctcaccg gcgcgcacct ggaggccgct ctggaggagg gggcggggccc cagccccacc | 540 |
| accttccact acgagctggt tcaggccccc aggaagggta acctcaggct gcagggcgcc | 600 |
| cggctgtccg aggggcaggg cttcacccag gatgacctgc aggccggccg ggtgacctac | 660 |
| ggggccacgg cgcgcacctc ggagaccgtg gaggacgcct tccgtttccg cgtcacgggct | 720 |
| ccgccacatt tctccccgct ctacaccttc cccatccaca tcgggggtga ccccgacgcc | 780 |
| cccgtcctca ccaacgtcct cctctccgtg cccgagggag gcgagggcgt cctctccgcg | 840 |
| gaacacctgt tcgtcaagag cctcaacagc gccagctacc tctatgaggt catggagcgg | 900 |
| ccccgccacg gcggctggt ctggagggggg gcgcaggacg aggccaccgc ggtgacgtcc | 960 |
| ttcaccaacg aggacctgct gcagggccgg ctggtctacc agcatgacaa ctccgagacc | 1020 |
| acggaagacg acatccccct cgtggcaacc cgccagagtg agggcagcgg cggcctggcc | 1080 |
| tgggaggagg tccggggcgt cttccgcgtg gccatccagc ccgtgaacga ccacgctccc | 1140 |
| gtgcagaccg tcagccgcgt cttccacgtg gccggggggcg ggcggcggct gctgacgacc | 1200 |
| gacgacgtgg ccttcagtga cgccgactcc ggcttcgccg acgcgcagct ggtgctgacc | 1260 |
| cgcaaggacc ttctcttcgg cagcatcgtg gccgcggacg agcccacgcg gcccatctac | 1320 |
| cgcttctccc aggaggacct ccggaagagg gcgtcctgt tcgtgcactc cggggccgac | 1380 |
| cgcggctgga tccagctgca ggtgtccgac gggcggcacc aggccaccgc gctgcttgaa | 1440 |
| gtgcaggcat ccgagcccta tctccgcgtg gccaatggct ccagcctcgt ggtccctcag | 1500 |
| ggggccaggg gcaccatcga cacagccgtg ctccgcctgg acaccaacct agacattcgc | 1560 |
| agcggggatg aggtccgcta ccgtgtcaca gccggcccgc actgggggca gctgctccgg | 1620 |

```
gccggccagc cggccacagc cttctcccaa caggacctgc tggacggggc cgtcctctac    1680
agccacaacg gcagcctgag cccgcaggac accctggcct tctccgtgga ggcagggcct    1740
gtgctcacgg atgccaccct gcaggtgacc attgccttgg aggggccatt ggccccactg    1800
catctggtcc agaacaagaa gatctacgtc ttccagggg aggcagctga gatcagaaag    1860
gatcagctgg aggcagcgca ggaggcagtg ccgcccgccc aaattgtgtt ctcggtgaag    1920
accccgccgc gggccggcta cctggtgatg ctgtcccgcg cgcctccgt ggccgggccg    1980 cccagctggg accccgtgca gagcttctcc caggaggcgg tggacgccgg cagggtcctg    2040
tacctccact cccgccccga ggcctggagt gactccttct ccctagacgt gggctcaggc    2100
ctgggtgcgc ccctcgaggg cgtccgcgtg gagctggagg tgctgcccgc caccatccca    2160
ctggaggcac agaacttcag cgtccccgag ggcggcagcc gcgtgctggc cccccgctg    2220 ctccaggtcg ccgggcccta cttccctgca ctgcccggcc tcgaactgcg ggtcctcgag    2280
cagcccctgc acgggccct gcggagagag gaggcccctc aagcggggac cctcagcgct    2340
ttctcctgga aagaggtaga acagcagcag atccgctatg tgcacgacgg gagtgagacg    2400
ctgacagaca gcttcaccct agtggctaac gcctccgagc tggaccgcca gagccaccct    2460
gtggccttca ccatcaccgt cctgcccgtc aatgaccaac cgcccatcct caccgcaaac    2520
acaggcctaa cgatgtggga gggggccacc gtgcccttcc ctccggaggc cctgaggggt    2580
gcggacagcg actcgggccc ggaggacctg gtctacacca tcgagcggcc cagcaacggg    2640
caggtggtgc tgcgggcggc gccaggcacc gaggtgcaca gcttcacgca ggcccagctg    2700
gacgacgggc tcgtgctgtt ctcacacaga ggagccctgg acggaggctt ccgcttcagc    2760
ctgtccgacg gcgagcacgc ttcccccgga cacttcttcc gcgtgacggc cagaagcag    2820 ctgctcctct ccctggaggg cagccggacg ctgaccgtgt gcccagggtc ggtccagccg    2880
ctcagcagcc agagcctgag agccagctcc agtgccggca ccgatccgca gcacctgctc    2940
taccgggtgg tgcagggccc ccggctgggc cgcctgctcc gcgcccagca gggcggcacc    3000
ggggaggtcc tggtgaactt cacgcaagcc gaggtatacg cgggggatgt tgtgtatgag    3060
cacaagatgc ctgctgagcc cttctgggag gtccacgacg ccctggagct ccggctgtcc    3120
tcgccccccg cccccgacgt ggccgccacc ctggaggtgg ccgtgtcctt cgaggccgcc    3180
tgcccgcagc gccccagccg cctctggagg aacgagggtc tctgggtggc cgagggccag    3240
caggcggaca tcaccagcgc cgccctggac gcctccaacc tgctggcgcg cgtccccgcc    3300
gcgctgcgcg cccggcacga cgtgctgttc caggtgacgc ggttcccggc gcggggccgg    3360
ctgctgctgg cggggcgggc gctgcacgcg ggccgggcgc acttcctgca gtcggagctg    3420
gcggcggggc tcctggccta cgcgcacggc ggcggggcg cgcagcccga cggcttcggc    3480
ttccgcgcgc agctgcaggg ccccgcgggc gccgggccgg gcgcgctccc cgcgctcccc    3540
gcgctccccg acgaggcctt cgccgtgcgc gtggggccg cggcgtccga ccgctgcgc    3600 ctgccccgcg gctcccgcgc gcccgtgtcc cgcgcgcagc tccgcgtgca gctcccgggc    3660
gccgcgcccg ccgacgtgca gtacgaggtg cggcgcgcgg ccccggcgg cttcctgagc    3720 ctcgcgggcg cgggcgcggg cccggtgcgc cgcttctcgc aggccgacgt ggacgcgggc    3780
cgcctggcct tcgtggccaa cggcagcagc gtggcgggcg tgctgcagct gagcgcgtgg    3840
gccgcgccca gccgcgcgt gcccgtgcg ctggccgtgg acgtgctgcc cgccgccatc    3900
gaggtgcagc tgcgcgcgcc cctggaggtg cccaggcgc tggggcgctg cgcgctcggg    3960
```

```
ccgcggcagc tgcgcgtcgt gtcggaccgc gccgagcccg aggccgccta ccgcgtgacc    4020
cgggcgccgc gcttcgggca gctcctggtg gcgggcaggc cggccggcgc cttcagccag    4080
cggcaggtgg accgcggcga cgtggagttc gccttcaccg acctgtcctc ccgcgcgac     4140 cgcttcgccg tcctggccca cgcgcggggc gccaacgcca cggccacggt ggacgtcacg    4200
gtcgcggcgc tgctgcgggt cgggccccgg gggccgtggc cgcagggcgc caccctgcgc    4260
ctggacccgg ccgtcctgga cgccgccgag ctggccaacc gcacgggcgg ggagccgcgc    4320
ttccgcctgc tggccgggcc ccggctgggc cgcctggtgc gcgtggcccg cgcggggccg    4380
gagcccgtgg agcagttcac gcagcgggac ctggagggcg ggaggctggg gctgcagctg    4440
ggccgcgccc ccggccccac gggcgacagc ctcacgctgg agctgtgggc gcccggcgtc    4500
cccccggccg tggcctccct ggacttccac accgagccct acgacgcggc gcgcccctac    4560
ggcgtggccc tgctcagcct ccccgaggaa gccggggcac ccgacagcgg cgccccggcc    4620
acgggccagc cggccgcgcc aggccccagc cccgggccca ccgcggccag cggcggcttc    4680
ctgggcctcc tggaggccaa catgttcagc atcatcatcc ccgtgtgcct ggtcctcctg    4740
ctcctggccc tgctcctgcc gctgctcttc tacctgcgca gcggaacaa gacgggcaag     4800 cacgacgtcc aggtgctgac cgccaagccc cgcaacggcc tggccggcga cacggagacc    4860
ttccgcaagg tggagccggg ccacgccatc ccgctcacgg ccgtgcccgg ccaggggccc    4920
ccgcccggcg gccagcccga cccagagctg ctgcagtact gtcggacacc caaccccgcc    4980
ctcaaaaacg gccagtactg ggtgtga                                       5007

<210> SEQ ID NO 19
<211> LENGTH: 2157
<212> TYPE: DNA
<213> ORGANISM: artificial
<220> FEATURE:
<223> OTHER INFORMATION: Dog D3

<400> SEQUENCE: 19
ctgaccgtgt gcccagggtc ggtccagccg ctcagcagcc agagcctgag agccagctcc      60
agtgccggca ccgatccgca gcacctgctc taccgggtgg tgcagggccc ccggctgggc     120
cgcctgctcc gcgcccagca gggcggcacc ggggaggtcc tggtgaactt cacgcaagcc     180
gaggtatacg cggggggatgt tgtgtatgag cacaagatgc ctgctgagcc cttctgggag    240
gtccacgacg ccctggagct ccggctgtcc tcgccccccg ccccgacgt ggccgccacc      300 ctggaggtgg ccgtgtcctt cgaggccgcc tgcccgcagc gccccagccg cctctggagg    360
aacgagggtc tctgggtggc cgagggccag caggcggaca tcaccagcgc cgccctggac   420
gcctccaacc tgctggcgcg cgtccccgcc gcgctgcgcg cccggcacga cgtgctgttc    480
caggtgacgc ggttcccggc gcggggccgg ctgctgctgg cggggcgggc gctgcacgcg   540
ggccgggcgc acttcctgca gtcggagctg gggcggggc tcctggccta cgcgcacggc    600 ggcggggggcg cgcagcccga cggcttcggc ttccgcgcgc agctgcaggg ccccgcgggc    660
gccgggccgg gcgcgctccc cgcgctcccc gcgctccccg acgaggcctt cgccgtgcgc    720
gtgggggccg cggcgtccga ccgctgcgcg ctgccccgcg gctcccgcgc gcccgtgtcc    780
cgcgcgcagc tccgcgtgca gctcccgggc gccgcgcccg ccgacgtgca gtacgaggtg    840
cggccgcgcg ccccggcgg cttcctgagc ctgcgcggcg cgggcgcggg ccggtgcgc     900 cgcttctcgc aggccgacgt ggacgcgggc cgcctggcct tcgtgccaa cggcagcagc     960 gtggcgggcg tgctgcagct gagcgcgtgg gccggcgcca gccgcgcgcgt gccgtggcg   1020
```

-continued

```
ctggccgtgg acgtgctgcc cgccgccatc gaggtgcagc tgcgcgcgcc cctggaggtg    1080
ccccaggcgc tggggcgctg cgcgctcggg ccgcggcagc tgcgcgtcgt gtcggaccgc    1140
gccgagcccg aggccgccta ccgcgtgacc cgggcgccgc gcttcgggca gctcctggtg    1200
gcgggcaggc cggccggcgc cttcagccag cggcaggtgg accgcggcga cgtggagttc    1260
gccttcaccg acctgtcctc cccgcgcgac cgcttcgccg tcctggccca cgcgcggggc    1320
gccaacgcca cggccacggt ggacgtcacg gtcgcgcgc tgctgcgggt cgggccccgg     1380
gggccgtggc cgcagggcgc caccctgcgc ctggacccgg ccgtcctgga cgccgccgag    1440
ctggccaacc gcacgggcgg ggagccgcgc ttccgcctgc tggccgggcc ccggctgggc    1500
cgcctggtgc gcgtggcccg cgcggggccg gagcccgtgg agcagttcac gcagcgggac    1560
ctggagggcg ggaggctggg gctgcagctg gccgcgcccc ccggcccac gggcgacagc     1620 ctcacgctgg agctgtgggc gcccggcgtc ccccggccg tggcctccct ggacttccac      1680
accgagccct acgacgcggc gcgccccctac ggcgtggccc tgctcagcct ccccgaggaa   1740
gccggggcac ccgacagcgg cgccccggcc acgggccagc cgggcgcgcc aggccccagc    1800
cccgggccca ccgcggccag cggcggcttc ctgggcctcc tggaggccaa catgttcagc    1860
atcatcatcc ccgtgtgcct ggtcctcctg ctcctggccc tgctcctgcc gctgctcttc    1920
tacctgcgca gcggaacaa gacgggcaag cacgacgtcc aggtgctgac cgccaagccc    1980
cgcaacggcc tggccggcga cacggagacc ttccgcaagg tggagccggg ccacgccatc    2040
ccgctcacgg ccgtgcccgg ccaggggccc cgcccggcg ccagcccga cccagagctg      2100 ctgcagtact gtcggacacc caaccccgcc ctcaaaaacg gccagtactg ggtgtga       2157
```

<210> SEQ ID NO 20
<211> LENGTH: 5049
<212> TYPE: DNA
<213> ORGANISM: artificial
<220> FEATURE:
<223> OTHER INFORMATION: Human D2+D3

<400> SEQUENCE: 20

```
cgggtcagcg atggactgca ggccagcccc ccggccacgc tgaaggtggt ggccatccgg      60
ccggccatac agatccaccg cagcacaggg ttgcgactgg cccaaggctc tgccatgccc    120
atcttgcccg ccaacctgtc ggtggagacc aatgccgtgg ggcaggatgt gagcgtgctg    180
ttccgcgtca ctggggccct gcagtttggg gagctgcaga gcagggggc aggtggggtg    240 gagggtgctg agtggtgggc cacacaggcg ttccaccagc gggatgtgga gcagggccgc    300
gtgaggtacc tgagcactga cccacagcac cacgcttacg acaccgtgga gaacctggcc    360
ctggaggtgc agtgggcca ggagatcctg agcaatctgt ccttcccagt gaccatccag    420
agagccactg tgtggatgct gcggctggag ccactgcaca ctcagaacac ccagcaggag    480
accctcacca cagcccacct ggaggccacc ctggaggagg caggcccaag ccccccaacc    540
ttccattatg aggtggttca ggctcccagg aaaggcaacc ttcaactaca gggcacaagg    600
ctgtcagatg gccagggctt cacccaggat gacatacagg ctggccgggt gacctatggg    660
gccacagcac gtgcctcaga ggcagtcgag gacaccttcc gtttccgtgt cacagctcca    720
ccatatttct ccccactcta taccttcccc atccacattg gtggtgaccc agatgcgcct    780
gtcctcacca atgtcctcct cgtggtgcct gagggtggtg agggtgtcct ctctgctgac    840
cacctctttg tcaagagtct caacagtgcc agctacctct atgaggtcat ggagcggccc    900
```

```
cgccatggga ggttggcttg gcgtgggaca caggacaaga ccactatggt gacatccttc    960
accaatgaag acctgttgcg tggccggctg gtctaccagc atgatgactc cgagaccaca   1020
gaagatgata tcccatttgt tgctacccgc cagggcgaga gcagtggtga catggcctgg   1080
gaggaggtac ggggtgtctt ccgagtggcc atccagcccg tgaatgacca cgcccctgtg   1140
cagaccatca gccggatctt ccatgtggcc cggggtgggc ggcggctgct gactacagac   1200
gacgtggcct tcagcgatgc tgactcgggc tttgctgacg cccagctggt gcttacccgc   1260
aaggacctcc tctttggcag tatcgtggcc gtagatgagc ccacgcggcc catctaccgc   1320
ttcacccagg aggacctcag gaagaggcga gtactgttcg tgcactcagg gctgaccgt    1380
ggctggatcc agctgcaggt gtccgacggg caacaccagg ccactgcgct gctggaggtg   1440
caggcctcgg aaccctacct ccgtgtggcc aacggctcca gccttgtggt ccctcaagga   1500
ggccagggca ccatcgacac ggccgtgctc cacctggaca ccaacctcga catccgcagt   1560
ggggatgagg tccactacca cgtcacagct ggccctcgct ggggacagct agtccgggct   1620
ggtcagccag ccacagcctt ctcccagcag gacctgctgg atggggccgt tctctatagc   1680
cacaatggca gcctcagccc cgcgacacc atggccttct ccgtggaagc agggccagtg    1740
cacacggatg ccaccctaca agtgaccatt gccctagagg gcccactggc cccactgaag   1800
ctggtccggc acaagaagat ctacgtcttc cagggagagg cagctgagat cagaagggac   1860
cagctggagg cagcccagga ggcagtgcca cctgcagaca tcgtattctc agtgaagagc   1920
ccaccgagtg ccggctacct ggtgatggtg tcgcgtggcg ccttggcaga tgagccaccc   1980
agcctggacc ctgtgcagag cttctcccag gaggcagtgg acacaggcag ggtcctgtac   2040
ctgcactccc gccctgaggc ctggagcgat gccttctcgc tggatgtggc ctcaggcctg   2100
ggtgctcccc tcgagggcgt ccttgtggag ctggaggtgc tgcccgctgc catcccacta   2160
gaggcgcaaa acttcagcgt ccctgagggt ggcagcctca ccctggcccc tccactgctc   2220
cgtgtctccg ggccctactt ccccactctc ctggggcctca gcctgcaggt gctggagcca   2280
ccccagcatg gagccctgca aaggaggac ggaccctcaag ccaggaccct cagcgccttc   2340
tcctggagaa tggtggaaga gcagctgatc cgctacgtgc atgacgggag cgagacactg   2400
acagacagtt ttgtcctgat ggctaatgcc tccgagatgg atcgccagag ccatcctgtg   2460
gccttcactg tcactgtcct gcctgtcaat gaccaacccc ccatcctcac tacaaacaca   2520
ggcctgcaga tgtgggaggg ggccactgcg cccatccctg cggaggctct gaggagcacg   2580
gacggcgact ctgggtctga ggatctggtc tacaccatcg agcagcccag caacgggcgg   2640
gtagtgctgc gggggggcgcc gggcactgag gtgcgcagct tcacgcaggc ccagctggac   2700
ggcgggctcg tgctgttctc acacagagga ccctggatg gaggcttccg cttccgcctc    2760
tctgacggcg agcacacttc ccccggacac ttcttccgag tgacggccca gaagcaagtg   2820
ctcctctcgc tgaagggcag ccagacactg actgtctgcc cagggtccgt ccagccactc   2880
agcagtcaga ccctcagggc cagctccagc gcaggcactg accccagct cctgctctac    2940
cgtgtggtgc ggggccccca gctaggccgg ctgttccacg cccagcagga cagcacaggg   3000
gaggccctgg tgaacttcac tcaggcagag gtctacgctg gaatattct gtatgagcat    3060
gagatgcccc ccgagccctt tgggaggcc catgataccc tagagctcca gctgtcctcg    3120
ccgcctgccc gggacgtggc cgccacccctt gctgtggctg tgtcttttga ggctgcctgt   3180
ccccagcgcc ccagccacct ctggaagaac aaaggtctct gggtccccga gggccagcgg   3240
gccaggatca ccgtggctgc tctggatgcc tccaatctct tggccagcgt tccatcaccc   3300
```

```
cagcgctcag agcatgatgt gctcttccag gtcacacagt tccccagccg gggccagctg    3360
ttggtgtccg aggagcccct ccatgctggg cagccccact tcctgcagtc ccagctggct    3420
gcagggcagc tagtgtatgc ccacggcggt gggggcaccc agcaggatgg cttccacttt    3480
cgtgcccacc tccagggggcc agcaggggcc tccgtggctg acccccaaac ctcagaggcc    3540
tttgccatca cggtgaggga tgtaaatgag cggccccctc agccacaggc ctctgtccca    3600
ctccggctca cccgaggctc tcgtgccccc atctcccggg cccagctgag tgtggtggac    3660
ccagactcag ctcctgggga gattgagtac gaggtccagc gggcacccca caacggcttc    3720
ctcagcctgg tgggtggtgg cctggggccc gtgacccgct tcacgcaagc cgatgtggat    3780
tcagggcggc tggccttcgt ggccaacggg agcagcgtgg caggcatctt ccagctgagc    3840
atgtctgatg gggccagccc acccctgccc atgtccctgg ctgtggacat cctaccatcc    3900
gccatcgagg tgcagctgcg ggcacccctg gaggtgcccc aagctttggg gcgctcctca    3960
ctgagccagc agcagctccg ggtggtttca gatcggagg agccagaggc agcataccgc    4020
ctcatccagg accccagta tgggcatctc ctggtgggcg ggcggcccac ctcggccttc    4080
agccaattcc agatagacca gggcgaggtg gtctttgcct tcaccaactt ctcctcctct    4140
catgaccact tcagagtcct ggcactggct aggggtgtca atgcatcagc cgtagtgaac    4200
gtcactgtga gggctctgct gcatgtgtgg gcaggtgggc catggcccca gggtgccacc    4260
ctgcgcctgg accccaccgt cctagatgct ggcgagctgg ccaaccgcac aggcagtgtg    4320
ccgcgcttcc gcctcctgga gggacccccgg catggccgcg tggtccgcgt gccccgagcc    4380
aggacggagc ccggggggcag ccagctggtg gagcagttca ctcagcagga ccttgaggac    4440
gggaggctgg ggctggaggt gggcaggcca gaggggaggg cccccggccc cgcaggtgac    4500
agtctcactc tggagctgtg ggcacagggc gtcccgcctg ctgtggcctc cctggacttt    4560
gccactgagc cttacaatgc tgcccggccc tacagcgtgg ccctgctcag tgtccccgag    4620 gccgccccgga cggaagcagg gaagccagag agcagcaccc ccacaggcga gccaggcccc    4680
atggcatcca gccctgagcc cgctgtggcc aagggaggct tcctgagctt ccttgaggcc    4740
aacatgttca gcgtcatcat ccccatgtgc ctggtacttc tgctcctggc gctcatcctg    4800
cccctgctct tctacctccg aaaacgcaac aagacgggca agcatgacgt ccaggtcctg    4860
actgccaagc cccgcaacgg cctggctggt gacaccgaga cctttcgcaa ggtggagcca    4920
ggccaggcca tcccgctcac agctgtgcct ggccaggggc cccctccagg aggccagcct    4980
gacccagagc tgctgcagtt ctgccggaca cccaaccctg cccttaagaa tggccagtac    5040
tgggtgtga                                                           5049
```

<210> SEQ ID NO 21
<211> LENGTH: 2202
<212> TYPE: DNA
<213> ORGANISM: artificial
<220> FEATURE:
<223> OTHER INFORMATION: Human D3

<400> SEQUENCE: 21

```
ctgactgtct gcccagggtc cgtccagcca ctcagcagtc agaccctcag ggccagctcc      60
agcgcaggca ctgaccccca gctcctgctc taccgtgtgg tgcggggccc ccagctaggc     120
cggctgttcc acgcccagca ggacagcaca ggggaggccc tggtgaactt cactcaggca     180
gaggtctacg ctgggaatat tctgtatgag catgagatgc cccccgagcc cttttgggag     240
```

```
gcccatgata ccctagagct ccagctgtcc tcgccgcctg cccgggacgt ggccgccacc      300
cttgctgtgg ctgtgtcttt tgaggctgcc tgtccccagc gccccagcca cctctggaag      360
aacaaaggtc tctgggtccc cgagggccag cgggccagga tcaccgtggc tgctctggat      420
gcctccaatc tcttggccag cgttccatca ccccagcgct cagagcatga tgtgctcttc      480
caggtcacac agttccccag ccggggccag ctgttggtgt ccgaggagcc cctccatgct      540
gggcagcccc acttcctgca gtcccagctg gctgcagggc agctagtgta tgcccacggc      600
ggtgggggca cccagcagga tggcttccac tttcgtgccc acctccaggg gccagcaggg      660
gcctccgtgg ctggacccca aacctcgaga gcctttgcca tcacggtgag ggatgtaaat      720
gagcggcccc ctcagccaca ggcctctgtc ccactccggc tcacccgagg ctctcgtgcc      780
cccatctccc gggcccagct gagtgtggtg gacccagact cagctcctgg ggagattgag      840
tacgaggtcc agcgggcacc ccacaacggc ttcctcagcc tggtgggtgg tggcctgggg      900
cccgtgaccc gcttcacgca gccgatgtg attcagggc ggctggcctt cgtggccaac      960
gggagcagcg tggcaggcat cttccagctg agcatgtctg atggggccag cccaccctg     1020 cccatgtccc tggctgtgga catcctacca tccgccatcg aggtgcagct gcgggcaccc     1080
ctggaggtgc cccaagcttt ggggcgctcc tcactgagcc agcagcagct ccgggtggtt     1140
tcagatcggg aggagccaga ggcagcatac cgcctcatcc agggacccca gtatgggcat     1200
ctcctggtgg gcgggcggcc cacctcggcc ttcagccaat tccagataga ccagggcgag     1260
gtggtctttg ccttcaccaa cttctcctcc tctcatgacc acttcagagt cctggcactg     1320 gctagggtg tcaatgcatc agccgtagtg aacgtcactg tgagggctct gctgcatgtg     1380
tgggcaggtg ggccatggcc ccagggtgcc accctgcgcc tggaccccac cgtcctagat     1440
gctggcgagc tggccaaccg cacaggcagt gtgccgcgct tccgcctcct ggagggaccc     1500
cggcatggcc gcgtggtccg cgtgccccga gccaggacgg agcccgggg cagccagctg     1560 gtggagcagt tcactcagca ggaccttgag gacgggaggc tggggctgga ggtgggcagg     1620
ccagagggga gggccccgg ccccgcaggt gacagtctca ctctggagct gtgggcacag     1680
ggcgtcccgc ctgctgtggc ctccctggac tttgccactg agccttacaa tgctgcccgg     1740
ccctacagcg tggccctgct cagtgtcccc gaggccgccc ggacggaagc agggaagcca     1800
gagagcagca ccccccacagg cgagccaggc cccatggcat ccagccctga cccgctgtg     1860 gccaagggag gcttcctgag cttccttgag gccaacatgt tcagcgtcat catccccatg     1920
tgcctggtac ttctgctcct ggcgctcatc ctgcccctgc tcttctacct ccgaaaacgc     1980
aacaagacgg gcaagcatga cgtccaggtc ctgactgcca agccccgcaa cggcctggct     2040
ggtgacaccg agaccttctg caaggtggag ccaggccagg ccatcccgct cacagctgtg     2100
cctggccagg ggccccctcc aggaggccag cctgacccag agctgctgca gttctgccgg     2160
acacccaacc ctgcccttaa gaatggccag tactgggtgt ga                        2202
```

<210> SEQ ID NO 22
<211> LENGTH: 3187
<212> TYPE: DNA
<213> ORGANISM: artificial
<220> FEATURE:
<223> OTHER INFORMATION: HuDo Dog

<400> SEQUENCE: 22

```
gatctacgtc ttccaggggg aggcagctga gatcagaaag gatcagctgg aggcagcgca       60
ggaggcagtg ccgcccgccc aaattgtgtt ctcggtgaag accccgccgc gggccggcta      120
```

```
cctggtgatg ctgtcccgcg gcgcctccgt ggccgggccg cccagctggg accccgtgca    180
gagcttctcc caggaggcgg tggacgccgg cagggtcctg tacctccact cccgccccga    240
ggcctggagt gactccttct ccctagacgt gggctcaggc ctgggtgcgc ccctcgaggg    300
cgtccgcgtg gagctggagg tgctgcccgc caccatccca ctggaggcac agaacttcag    360
cgtccccgag ggcggcagcc gcgtgctggc ccccccgctg ctccaggtcg ccgggcccta    420
cttccctgca ctgcccggcc tcgaactgcg ggtcctcgag cagcccctgc acggggccct    480
gcggagagag gaggcccctc aagcggggac cctcagcgct ttctcctgga aagaggtaga    540
acagcagcag atccgctatg tgcacgacgg gagtgagacg ctgacagaca gcttcaccct    600
agtggctaac gcctccgagc tggaccgcca gagccaccct gtggccttca ccatcaccgt    660
cctgcccgtc aatgaccaac cgcccatcct caccgcaaac acaggcctaa cgatgtggga    720
gggggccacc gtgcccttcc ctccggaggc cctgaggggt gcggacagcg actcgggccc    780
ggaggacctg gtctacacca tcgagcggcc cagcaacggg caggtggtgc tgcgggcggc    840
gccaggcacc gaggtgcaca gcttcacgca ggcccagctg gacgacgggc tcgtgctgtt    900
ctcacacaga ggagccctgg acggaggctt ccgcttcagc ctgtccgacg gcgagcacgc    960
ttcccccgga cacttcttcc gcgtgacggc ccagaagcag ctgctcctct ccctggaggg   1020
cagccggacg ctgaccgtgt gcccagggtc ggtccagccg ctcagcagcc agagcctgag   1080
agccagctcc agtgccggca ccgatccgca gcacctgctc taccgggtgg tgcagggccc   1140
ccggctgggc cgcctgctcc gcgcccagca gggcggcacc ggggaggtcc tggtgaactt   1200
cacgcaagcc gaggtatacg cgggggatgt tgtgtatgag cacaagatgc ctgctgagcc   1260
cttctgggag gtccacgacg ccctggagct ccggctgtcc tcgcccccg  cccccgacgt   1320
ggccgccacc ctggaggtgg ccgtgtcctt cgaggccgcc tgcccgcagc gccccagccg   1380
cctctggagg aacgagggtc tctgggtggc cgagggccag caggcggaca tcaccagcgc   1440
cgccctggac gcctccaacc tgctggcgcg cgtccccgcc gcgctgcgcg cccggcacga   1500
cgtgctgttc caggtgacgc ggttcccggc gcggggccgg ctgctgctgg cggggcgggc   1560
gctgcacgcg ggccgggcgc acttcctgca gtcggagctg gcggcggggc tcctggccta   1620
cgcgcacggc ggcgggggcg cgcagcccga cggcttcggc ttccgcgcgc agctgcaggg   1680
ccccgcgggc gccgggccgg gcgcgctccc cgcgctcccc gcgctccccg acgaggcctt   1740
cgccgtgcgc gtgggggccg cggcgtccga gccgctgcgc ctgccccgcg gctcccgcgc   1800
gcccgtgtcc cgcgcgcagc tccgcgtgca gctcccgggc gccgcgcccg ccgacgtgca   1860
gtacgaggtg cggcgcgcgg cccccggcgg cttcctgagc ctcgcgggcg cgggcgcggg   1920
cccggtgcgc cgcttctcgc aggccgacgt ggacgcgggc cgcctggcct tcgtggccaa   1980
cggcagcagc gtggcgggcg tgctgcagct gagcgcgtgg gccggcgcca gcccgcgcgt   2040
gcccgtggcg ctggccgtgg acgtgctgcc cgccgccatc gaggtgcagc tgcgcgcgcc   2100
cctggaggtg ccccaggcgc tggggcgctg cgcgctcggg ccgcggcagc tgcgcgtcgt   2160
gtcggaccgc gccgagcccg aggccgccta ccgcgtgacc cgggcgccgc gcttcgggca   2220
gctcctggtg gcgggcaggc cggccggcgc cttcagccag cggcaggtgg accgcggcga   2280
cgtggagttc gccttcaccg acctgtcctc cccgcgcgac cgcttcgccg tcctggccca   2340
cgcgcggggc gccaacgcca cggccacggt ggacgtcacg gtcgcggcgc tgctgcgggt   2400
cgggccccgg gggccgtggc cgcagggcgc caccctgcgc ctggacccgg ccgtcctgga   2460
```

| | |
|---|---:|
| cgccgccgag ctggccaacc gcacgggcgg ggagccgcgc ttccgcctgc tggccgggcc | 2520 |
| ccggctgggc cgcctggtgc gcgtggcccg cgcggggccg gagcccgtgg agcagttcac | 2580 |
| gcagcgggac ctggagggcg ggaggctggg gctgcagctg ggccgcgccc ccggcccac | 2640 |
| gggcgacagc ctcacgctgg agctgtgggc gcccggcgtc ccccggccg tggcctccct | 2700 |
| ggacttccac accgagccct acgacgcggc gcgcccctac ggcgtggccc tgctcagcct | 2760 |
| ccccgaggaa gccggggcac ccgacagcgg cgccccggcc acgggccagc cgggcgcgcc | 2820 |
| aggccccagc cccgggccca ccgcggccag cggcggcttc ctgggcctcc tggaggccaa | 2880 |
| catgttcagc atcatcatcc ccgtgtgcct ggtcctcctg ctcctggccc tgctcctgcc | 2940 |
| gctgctcttc tacctgcgca agcggaacaa gacgggcaag cacgacgtcc aggtgctgac | 3000 |
| cgccaagccc cgcaacggcc tggcggcga cacggagacc ttccgcaagg tggagccggg | 3060 |
| ccacgccatc ccgctcacgg ccgtgcccgg ccaggggccc ccgcccggcg ccagcccga | 3120 |
| cccagagctg ctgcagtact gtcggacacc caaccccgcc ctcaaaaacg gccagtactg | 3180 |
| ggtgtag | 3187 |

<210> SEQ ID NO 23
<211> LENGTH: 3232
<212> TYPE: DNA
<213> ORGANISM: artificial
<220> FEATURE:
<223> OTHER INFORMATION: DoHu Hu

<400> SEQUENCE: 23

| | |
|---|---:|
| gatctacgtc ttccagggag aggcagctga gatcagaagg gaccagctgg aggcagccca | 60 |
| ggaggcagtg ccacctgcag acatcgtatt ctcagtgaag agcccaccga gtgccggcta | 120 |
| cctggtgatg gtgtcgcgtg gcgccttggc agatgagcca cccagcctgg accctgtgca | 180 |
| gagcttctcc caggaggcag tggacacagg cagggtcctg tacctgcact cccgccctga | 240 |
| ggcctggagc gatgccttct cgctggatgt ggcctcaggc ctgggtgctc ccctcgaggg | 300 |
| cgtccttgtg gagctggagg tgctgcccgc tgccatccca ctagaggcgc aaaacttcag | 360 |
| cgtccctgag ggtggcagcc tcaccctggc ccctccactg ctccgtgtct ccgggcccta | 420 |
| cttccccact ctcctgggcc tcagcctgca ggtgctggag ccaccccagc atggagccct | 480 |
| gcagaaggag gacggacctc aagccaggac cctcagcgcc ttctcctgga gaatggtgga | 540 |
| agagcagctg atccgctacg tgcatgacgg gagcgagaca ctgacagaca gttttgtcct | 600 |
| gatggctaat gcctccgaga tggatcgcca gagccatcct gtggccttca ctgtcactgt | 660 |
| cctgcctgtc aatgaccaac cccccatcct cactacaaac acaggcctgc agatgtggga | 720 |
| gggggccact cgcgcccatc ctgcggaggc tctgaggagc acggacggcg actctgggtc | 780 |
| tgaggatctg gtctacacca tcgagcagcc cagcaacggg cgggtagtgc tgcgggggc | 840 |
| gccgggcact gaggtgcgca gcttcacgca ggcccagctg acggcgggc tcgtgctgtt | 900 |
| ctcacacaga ggaaccctgg atggaggctt ccgcttccgc ctctctgacg gcgagcacac | 960 |
| ttcccccgga cacttcttcc gagtgacggc ccagaagcaa gtgctcctct cgctgaaggg | 1020 |
| cagccagaca ctgactgtct gcccagggtc cgtccagcca ctcagcagtc agaccctcag | 1080 |
| ggccagctcc agcgcaggca ctgacccca gctcctgctc taccgtgtgg tgcggggccc | 1140 |
| ccagctaggc cggctgttcc acgcccagca ggacagcaca ggggaggccc tggtgaactt | 1200 |

```
                                    -continued
cactcaggca gaggtctacg ctgggaatat tctgtatgag catgagatgc cccccgagcc    1260
cttttgggag gcccatgata ccctagagct ccagctgtcc tcgccgcctg cccgggacgt    1320
ggccgccacc cttgctgtgg ctgtgtcttt tgaggctgcc tgtccccagc gccccagcca    1380
cctctggaag aacaaaggtc tctgggtccc cgagggccag cgggccagga tcaccgtggc    1440
tgctctggat gcctccaatc tcttggccag cgttccatca ccccagcgct cagagcatga    1500
tgtgctcttc caggtcacac agttccccag ccggggccag ctgttggtgt ccgaggagcc    1560
cctccatgct gggcagcccc acttcctgca gtcccagctg gctgcagggc agctagtgta    1620
tgcccacggc ggtgggggca cccagcagga tggcttccac tttcgtgccc acctccaggg    1680
gccagcaggg gcctccgtgg ctggacccca aacctcagag gcctttgcca tcacggtgag    1740
ggatgtaaat gagcggcccc ctcagccaca ggcctctgtc ccactccggc tcacccgagg    1800
ctctcgtgcc cccatctccc gggcccagct gagtgtggtg gacccagact cagctcctgg    1860
ggagattgag tacgaggtcc agcgggcacc ccacaacggc ttcctcagcc tggtgggtgg    1920
tggcctgggg cccgtgaccc gcttcacgca agccgatgtg gattcagggc ggctggcctt    1980
cgtggccaac gggagcagcg tggcaggcat cttccagctg agcatgtctg atggggccag    2040
cccacccctg cccatgtccc tggctgtgga catcctacca tccgccatcg aggtgcagct    2100
gcgggcaccc ctggaggtgc cccaagcttt ggggcgctcc tcactgagcc agcagcagct    2160
ccgggtggtt tcagatcggg aggagccaga ggcagcatac cgcctcatcc agggacccca    2220
gtatgggcat ctcctggtgg gcgggcggcc cacctcggcc ttcagccaat tccagataga    2280
ccagggcgag gtggtctttg ccttcaccaa cttctcctcc tctcatgacc acttcagagt    2340
cctggcactg gctaggggtg tcaatgcatc agccgtagtg aacgtcactg tgagggctct    2400
gctgcatgtg tgggcaggtg ggccatggcc ccagggtgcc accctgcgcc tggaccccac    2460
cgtcctagat gctggcgagc tggccaaccg cacaggcagt gtgccgcgct tccgcctcct    2520
ggagggaccc cggcatggcc gcgtggtccg cgtgccccga gccaggacgg agcccggggg    2580
cagccagctg gtggagcagt tcactcagca ggaccttgag gacgggaggc tggggctgga    2640
ggtgggcagg ccagagggga gggcccccgg ccccgcaggt gacagtctca ctctggagct    2700
gtgggcacag ggcgtcccgc ctgctgtggc ctccctggac tttgccactg agccttacaa    2760
tgctgcccgc ccctacagcg tggccctgct cagtgtcccc gaggccgccc ggacggaagc    2820
agggaagcca gagagcagca ccccacagg cgagccaggc cccatggcat ccagccctga    2880
gcccgctgtg gccaagggag gcttcctgag cttccttgag gccaacatgt tcagcgtcat    2940
catccccatg tgcctggtac ttctgctcct ggcgctcatc ctgccctgc tcttctacct    3000 ccgaaaacgc aacaagacgg gcaagcatga cgtccaggtc ctgactgcca agccccgcaa    3060
cggcctggct ggtgacaccg agacctttcg caaggtggag ccaggccagg ccatcccgct    3120
cacagctgtg cctggccagg ggcccctcc aggaggccag cctgacccag agctgctgca    3180
gttctgccgg acacccaacc ctgcccttaa gaatggccag tactgggtgt ga           3232
```

NUCLEIC ACID MOLECULES ENCODING FOR CHIMERIC CSPG4 PROTEINS AND THERAPEUTIC USES THEREOF

This application is the U.S. national phase of International Application No. PCT/IB2016/058042 filed 28 Dec. 2016, which designated the U.S. and claims priority to IT Patent Application No. 102015000088978 filed 30 Dec. 2015, the entire contents of each of which are hereby incorporated by reference.

FIELD OF INVENTION

The hereof description regards nucleic acid molecules encoding CSPG4 chimeric proteins and relative therapeutic uses, in particular for the treatment and/or prevention of CSPG4-positive neoplasms.

BACKGROUND OF THE INVENTION

Neoplastic cells are often distinguished from normal cells as they express tumor associated antigens (TAA) that can provide the cells with a proliferative and invasive advantage, contributing to tumor progression. These TAA can be recognized by the immune system that, thanks to its specificity and immunological memory, can attack and eliminate tumor cells in a selective manner without damaging cells of normal tissues, preventing recurrences and metastasis, which are the principal causes of tumor-associated death. This basis gives rise to the idea of generating anti-tumor DNA vaccines encoding for a specific TAA, in order to stimulate the oncological patient's immune system and to induce a specific and long-lasting immune response against tumor cells expressing the TAA.

A TAA highly involved in tumor processes is chondroitin sulfate proteoglycan 4 (CSPG4), a transmembrane proteoglycan initially identified 35 years ago on the membrane of human melanoma cells (Wilson et al. 1981, Campoli et al. 2010), and recently recognized as overexpressed on neuroectodermic-derived tumors such as glioblastomas (Stallcup and Huang 2008), in certain types of lymphoblastic and acute myeloid leukemia (Petrovici et al. 2010), in triple negative breast cancers (Wang et al. 2010a) and in head and neck carcinomas (Wang et al. 2010b). Moreover, its overexpression has been recently observed in cancer stem cells (Wang et al. 2010b), extremely resistant to conventional therapies and responsible for recurrences and metastasis, making CSPG4 an even more interesting target.

Thanks to its characteristics, CSPG4 has been considered by the National Cancer Institute as a prioritized antigen for translational research into clinical practice (Cheever et al. 2009). However, as for many other TAA, CSPG4 is an immunologically tolerated self-antigen, and the success of an anti-CSPG4 DNA vaccine therefore relies on its ability to break immune tolerance.

An attempt to develop a DNA vaccine for the treatment of canine malignant melanoma has been carried out by the hereof inventors and is described in (Riccardo et al. 2014). In this cited study, dogs affected by a stage II-III CSPG4-positive oral malignant melanoma, previously subjected to surgical resection of the tumor, were vaccinated with a plasmid encoding the human CSPG4. The vaccine was effective in prolonging the survival of canine patients thanks to the induction of a direct humoral response against CSPG4. However, the vaccine-induced antibodies recognized the canine CSPG4 protein with a low affinity. Moreover, the vaccine did not induce an evident specific cell-mediated response and some vaccinated dogs developed metastases that resulted in their death.

SUMMARY OF THE INVENTION

The object of the present description is to develop means for treating and/or preventing CSPG4-positive neoplasms in mammals, wherein these means are able to break the immune tolerance of the organism to be treated, stimulating a humoral response against CSPG4 and a specific cell-mediated immune response.

In agreement with the invention, the aforesaid object is obtained thanks to the solution specifically recalled in the attached claims, which represent an integral part of the present description.

One embodiment of the present invention regards a nucleic acid molecule encoding a full-length chimeric protein, chondroitin sulfate proteoglycan 4 (CSPG4), where the CSPG4 chimeric protein includes from the N-terminal to the C-terminal:
  i) a first portion derived from the human CSPG4 sequence and a second portion derived from the canine CSPG4 sequence, or
  ii) a first portion derived from the canine CSPG4 sequence and a second portion derived from the human CSPG4 sequence.

BRIEF DESCRIPTION OF THE FIGURES

The invention will be now described in detail, purely as an illustrative and non-limiting example, with reference to the attached figures, wherein:

FIG. 4. Nucleotide sequence of the chimeric antigen HuDo-CSPG4-1 (SEQ ID No.:5). The illustrated sequence includes: (A) the site recognized by the restriction enzyme EcoRI (double-underlined sequence) and the first 3737 bp of the human CSPG4 sequence (from the ATG start codon to the cutting site of the restriction enzyme BglII-single-underlined sequence), and (B) the 3187 bp of the canine CSPG4 sequence (from the cutting site of the restriction enzyme BglII to the STOP codon) as well as the sequence recognized by the restriction enzyme XbaI (sequence highlighted with a dotted line).

FIG. 5. Sequence of the chimeric antigen DoHu-CSPG4-1 (SEQ ID No.:10). The illustrated sequence includes: (A) the site recognized by the restriction enzyme EcoRI (double-underlined sequence) and the first 5018 bp of the canine CSPG4 sequence (XM_544783.2, from the ATG start codon to the cutting site of the restriction enzyme BglII-single-underlined sequence) and (B) the 3232 bp of the human CSPG4 sequence (from the cutting site of the restriction enzyme BglII to the STOP codon) as well as the sequence recognized by the restriction enzyme XbaI (sequence highlighted with a dotted line).

DETAILED DESCRIPTION OF THE INVENTION

Figure 1:
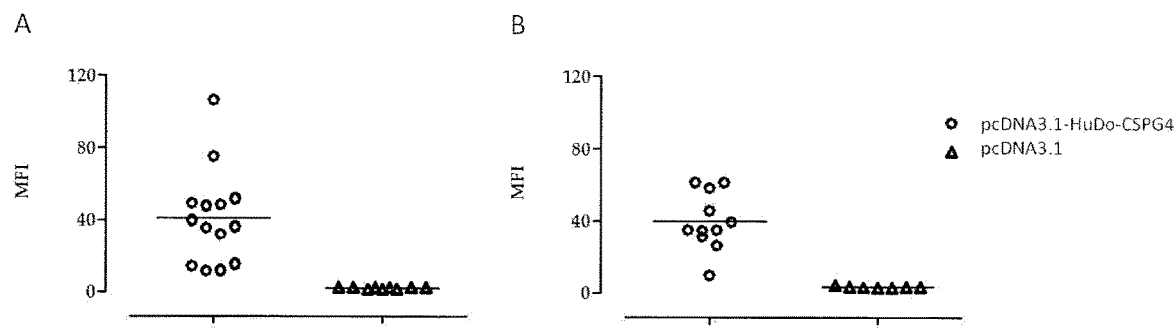
FIG. 1. Specific humoral response against CSPG4-positive human melanoma cells (SK-MEL28, ATCC® HTB-72™) (A) and against a primary cell line obtained, as described in (Riccardo et al. 2014), from a bioptic sample of a canine patient affected by CSPG4-positive oral melanoma (B) evaluated 2 weeks after the last vaccination of BALB/c mice with the plasmid pcDNA3.1-HuDo-CSPG4-1 or with the empty control plasmid pcDNA3.1. The antibody titer is expressed as mean fluorescence intensity (MFI).

The invention will be now described in detail, purely as an illustrative and non-limiting example.

In the following description, many specific details are presented to provide a complete understanding of the embodiments. The embodiments can be implemented in practice without one or more specific details, or with other methods, compounds, materials, etc. In other cases, structures, materials, or well-known operations are not shown or described in detail to avoid obscuring certain aspects of the embodiments.

Throughout the present specification, the reference to "one embodiment" or "an embodiment" signifies that a particular feature, structure, or characteristic described in connection with the embodiment is included in at least one embodiment. Thus, the presence of expressions such as "in a certain embodiment" or "in an embodiment" in various sites throughout the present specification does not necessarily always refer to the same embodiment.

Furthermore, the particular features, structures, or characteristics may be combined in any suitable manner in one or more embodiments.

The titles used herein are simply for convenience and do not interpret the object or the meaning of the embodiments.

The present description concerns means for treating and/or preventing CSPG4-positive neoplasms in mammals, where these means are able to break the immune tolerance of the organism to be treated, stimulating a humoral response against CSPG4, and a specific cellular-mediated immune response.

In one embodiment, the present description concerns nucleic acid molecules encoding chimeric CSPG4 proteins, where the chimeric CSPG4 proteins include a portion derived from the nucleotide sequence of the human oncogene CSPG4 (in which the "NCBI Reference Sequence" is Gene ID 1464) and a portion derived from the nucleotide sequence of the canine oncogene CSPG4 (in which the "NCBI Reference Sequence" is XM_544783.2 or Gene ID 487658). The human and canine amino acid sequences of CSPG4 have an 82% identity and an 88% similarity; the aforesaid characteristics of the canine and human CSPG4 sequences allow their assembly and production of chimeric proteins with a conformation and membrane expression similar to the native human and canine CSPG4 proteins so that they can induce a humoral and cellular-mediated response in the organism in which they are expressed.

One embodiment of the present description concerns a nucleic acid molecule encoding a full-length chimeric protein chondroitin sulfate proteoglycan 4 (CSPG4), where the chimeric CSPG4 protein includes from the N-terminal to the C-terminal:

i) a first portion derived from the human CSPG4 sequence and a second portion derived from the canine CSPG4 sequence, or ii) a first portion derived from the canine CSPG4 sequence and a second portion derived from the human CSPG4 sequence, where this chimeric protein is able to induce a humoral and cellular response.

In one embodiment, the nucleic acid molecule encoding a chimeric protein chondroitin sulfate proteoglycan 4 (CSPG4) comprises a first portion having an amino acid sequence encoded by a nucleotide sequence selected from SEQ ID No.: 11 to 17 or a sequence having a sequence identity of at least 90% with one of the sequences from SEQ ID No.: 11 to 17, and a second portion having an amino acid sequence encoded by a nucleotide sequence selected from SEQ ID No.: 18 to 23 or a sequence having a sequence identity of at least 90% with one of the sequences from SEQ ID No.: 18 to 23, and in which the first portion and the second portion are adjacent to each other and linked as indicated in the following Table 1:

TABLE 1

| First portion | Second portion |
| --- | --- |
| SEQ ID No.: 11 | SEQ ID No.: 18 |
| SEQ ID No.: 12 | SEQ ID No.: 19 |
| SEQ ID No.: 13 | SEQ ID No.: 20 |
| SEQ ID No.: 14 | SEQ ID No.: 21 |
| SEQ ID No.: 15 | SEQ ID No.: 22 |
| SEQ ID No.: 16 | SEQ ID No.: 23 |
| SEQ ID No.: 17 | SEQ ID No.: 23 |

The SEQ ID No.: 11 corresponds to the first 1920 bp (from the ATG start codon) of the human CSPG4 sequence; the SEQ ID No.: 12 corresponds to the first 4767 bp (from the ATG start codon) of the human CSPG4 sequence; the SEQ ID No.: 13 corresponds to the first 1965 bp (from the ATG start codon) of the canine CSPG4 sequence (Gene ID 487658); the SEQ ID No.: 14 corresponds to the first 4815 bp (from the ATG start codon) of the canine CSPG4 sequence (Gene ID 487658); the SEQ ID No.: 15 corresponds to the first 3737 bp (from the ATG start codon) of the human CSPG4 sequence; the SEQ ID No.: 16 corresponds to the first 5018 bp (from the ATG start codon) of the canine CSPG4 sequence (XM_544783.2); the SEQ ID No.: 17 corresponds to the first 3785 bp (from the ATG start codon) of the canine CSPG4 sequence (Gene ID 487658).

The SEQ ID No.: 18 corresponds to the 5007 bp starting from the base 1966 until the STOP codon of the canine sequence (Gene ID 487658); the SEQ ID No.: 19 corresponds to the 2157 bp starting from the base 4816 until the STOP codon of the canine sequence (Gene ID 487658); the SEQ ID No.: 20 corresponds to the 5049 bp starting from the base 1921 until the STOP codon of the human sequence; the SEQ ID No.: 21 corresponds to the 2202 bp starting from the base 4768 until the STOP codon of the human sequence; the SEQ ID No.: 22 corresponds to the 3187 bp starting from the base 3786 until the STOP codon of the canine sequence (Gene ID 487658); the SEQ ID No.: 23 corresponds to the 3232 bp starting from the base 3738 until the STOP codon of the human sequence.

In a preferential embodiment, the nucleic acid molecule encoding the chimeric protein chondroitin sulfate proteoglycan 4 (CSPG4) comprises a first portion having an amino acid sequence encoded by a nucleotide sequence selected from SEQ ID No.: 11, 15 and 17, and a second portion having an amino acid sequence encoded by a nucleotide sequence selected from SEQ ID No.: 18, 22 and 23, and in which the first portion and the second portion are adjacent to each other and linked as indicated in Table 1.

In one embodiment, nucleic acid molecules encoding chimeric CSPG4 proteins are part of a plasmid suitable for the in vivo administration in mammals, preferably a dog or a human, more preferably a dog. In addition to the aforesaid nucleic acid molecules encoding chimeric human/dog CSPG4 proteins, the plasmids can include other functional sequences necessary for the transcription of the chimeric protein, known to the expert of the field, among which can be cited: transcriptional promoters, sequences that start or stop transcription, genes encoding for antibiotic resistance, etc.

In an another embodiment of the hereof description, nucleic acid molecules encoding chimeric CSPG4 proteins or the relative plasmids are formulated as pharmaceutical compositions for the in vivo administration in a mammal, these pharmaceutical compositions can obviously contain pharmaceutically acceptable excipients and/or vehicles. Being vaccine pharmaceutical compositions, these compositions can contain adjuvants to stimulate the immune response of the organism to be treated. These adjuvants are well known in the state-of-the-art and it is not necessary in this description to provide specific details that are trackable in the scientific literature available to an expert in the field. Equally known to an expert in the field are the methods for administering a DNA vaccine in an animal or human patient.

Pharmaceutical compositions containing nucleic acid molecules encoding the herein-described chimeric CSPG4 proteins are used for the treatment and/or the prevention of CSPG4-positive neoplasms in a mammal. The term "treatment" means the administration of the aforesaid pharmaceutical compositions to patients (veterinary or human) who have already developed a CSPG4-positive neoplasm; the term "prevention" means the administration of the aforesaid pharmaceutical compositions to patients (veterinary or human) who are at risk of developing a CSPG4-postive neoplasm.

The hereof description demonstrates that plasmids encoding full-length chimeric human/dog CSPG4 proteins are able to stimulate an immune response in mice, dogs and humans, making these molecules suitable for producing a DNA vaccine intended for the treatment and/or prevention of a CSPG4-positive tumor in a mammal.

Hybrid plasmids encoding full-length chimeric human/dog CSPG4 proteins subject of the present description, being able to induce a combined humoral and cellular response, are more efficient in treating dogs affected by CSPG4-positive malignant melanomas (MM) compared to plasmids encoding the human CSPG4 antigen described in (Riccardo et al, 2014).

Moreover, the possibility of studying new anti-tumor therapies in large animals such as dogs, which spontaneously develop tumors characterized by histological, molecular and clinical-biological features similar to the human neoplasm counterparts, is acquiring a huge value for the translation of the preclinical phase into human clinics. In particular, canine MM (cMM) is one of the most interesting tumors for comparative oncology studies, since it shows many similarities to the human tumor counterpart, both from the anatomic, histopathologic and the genetic point of view (Bergman 2007, Simpson et al. 2014). In a manner analogous to that of humans, MM is also a frequent tumor in dogs, for which the standard treatments are: surgical resection of the tumor, and radio- and chemo-therapy, which only result in the local control of the tumor in 75% of animals, however the 1-year survival rate does not exceed 30% because of recurrences and metastases (Boston et al. 2014).

Considering that CSPG4 expression is also very frequent in several human neoplasms, such as MM, neuroectodermic-derived tumors (such as glioblastomas), lymphoblastic and acute myeloid leukemia, osteosarcomas, head and neck tumors and triple negative breast cancers, the present inventors investigated the possibility of using nucleic acid molecules encoding chimeric CSPG4 proteins described herein for the treatment of these human neoplasms.

Unexpectedly, the present inventors discovered that nucleic acid molecules encoding chimeric CSPG4 proteins, subject of the hereof description, can be used for preventing and/or treating CSPG4-positive neoplasms in humans. Indeed, the results reported here in human dendritic cells show that these nucleic acid molecules are able to break the tolerance and the unresponsiveness of the human T cells against the CSPG4 self-antigen and, therefore, can be used in the human oncology field for CSPG4-positive neoplasms.

Materials and Methods

Construction of Hybrid Human/Dog Sequences Encoding Chimeric CSPG4 Proteins

Two hybrid sequences encoding chimeric CSPG4 proteins were generated: the HuDo-CSPG4-1 encoding the chimeric CSPG4 protein in which the N-terminal region is derived from the human sequence and the remaining part from the canine sequence, and the DoHu-CSPG4-1 sequence encoding the CSPG4 chimeric protein in which the N-terminal region is derived from the canine sequence and the remaining part from the human sequence.

The human and the canine CSPG4 sequences, of which the "NCBI Reference Sequences" are Gene ID 1464 and XM_544783.2, respectively, were inserted into the plasmid backbone pcDNA3.1 (Clontech), generating the plasmids pcDNA3.1-Human-CSPG4 and pcDNA3.1-Dog-CSPG4, respectively. These plasmids were used as templates to amplify—by means of PCR—the cDNA fragments encoding the human and canine CSPG4 portions to be used to generate the hybrid sequences HuDo-CSPG4-1 and DoHu-CSPG4-1.

In particular, to amplify the portion encoding the N-terminal part of the human CSPG4 to be inserted into the HuDo-CSPG4-1 sequence, the plasmid pcDNA3.1-Human-CSPG4 and the following primers were used:

forward oligonucleotide (SEQ ID No.:1) that anneals on the ATG start codon and including—upstream—the sequence of the EcoRI recognition site and the EcoRI activity optimization followed by the Kozak sequence, SEQ ID No.: 1:
5'-CCGGAATTCGCCATGCAGTCCGGGCCGCGGCCC-3';

reverse oligonucleotide (SEQ ID No.:2) that anneals on the human CSPG4 sequence starting from 117 bp downstream of the BglII cutting site and including the sequence of the XbaI recognition site and XbaI activity optimization, SEQ ID No.: 2:
5'-GGTCTAGAGACACCATCACCAGGTAGCC-3'.

PCR was performed using reagents and the "proofreading" Taq polymerase from QIAGEN. Reagent quantities and specific reaction conditions (temperatures and times) are reported in the following Tables 2 and 3.

TABLE 2

| PCR solutions (20 μl final volume) | |
|---|---|
| Reagents | Volume |
| DNA (template) | 1 μl (100 ng) |
| Buffer 10X | 2 μl |
| dNTPs 10 mM | 0.5 μl |
| Forward oligonucleotide (SEQ ID No.: 1) | 1, .2 μl |
| Reverse oligonucleotide (SEQ ID No.: 2) | 1.2 μl |
| Taq Polymerase (1 U/μl) | 0.5 μl |
| H₂O | 13.6 μl |

TABLE 3

| Amplification protocol | | |
|---|---|---|
| Temperature | Time | Event |
| 94° C. | 2 min | Initial denaturation |
| 94° C. | 15 sec | Denaturation |
| 58° C. | 30 sec | Oligonucleotide annealing |
| 72° C. | 4 min 30 sec | Extension |
| For a total of 35 cycles | | |
| 72° C. | 8 min | Final extension |
| 4° C. | ∞ | |

The PCR product was purified with the "QIAquick PCR Purification Kit" (QIAGEN), digested with EcoRI and BglII restriction enzymes, purified again by gel electrophoresis and gel extraction using the "QIAquick Gel Extraction" (QIAGEN). The obtained product was named Hu-Fragment A.

Analogously, to amplify the portion encoding the C-terminal part of the canine CSPG4 to be inserted into the sequence HuDo-CSPG4-1, the plasmid pcDNA3.1-Dog-CSPG4 and the following oligonucleotides were used:

forward oligonucleotide (SEQ ID No.:3) that anneals on the dog CSPG4 sequence starting from 388 bp upstream of the BglII cutting site and including the sequence of the EcoRI recognition site and EcoRI activity optimization followed by the Kozak sequence, SEQ ID No.: 3:
5'-CCGGAATTCGCCTGCTTGAAGTGCAGGCATCCG-3';

reverse oligonucleotide (SEQ ID No.:4) that anneals on the STOP codon of the canine CSPG4 sequence and including the sequence of the XbaI recognition site and XbaI activity optimization, SEQ ID No.: 4:
5'-GGTCTAGATCACACCCAGTACTGGCCGTT-3'.

PCR was performed using reagents and the "proofreading" Taq polymerase from QIAGEN. Reagent quantities and specific reaction conditions (temperatures and times) are reported in the following Tables 4 and 5.

TABLE 4

| PCR solutions (20 μl final volume) | |
|---|---|
| Reagents | Volume |
| DNA (template) | 1 μl (100 ng) |
| Buffer 10X | 2 μl |
| dNTPs 10 mM | 0.5 μl |
| Forward oligonucleotide (SEQ ID No.: 3) | 1.2 μl |
| Reverse oligonucleotide (SEQ ID No.: 4) | 1.2 μl |
| Taq Polymerase (1 U/μl) | 0.5 μl |
| H₂O | 13.6 μl |

TABLE 5

| Amplification protocol | | |
|---|---|---|
| Temperature | Time | Event |
| 94° C. | 2 min | Initial denaturation |
| 94° C. | 15 sec | Denaturation |
| Gradient from 44 to 56° C. | 30 sec | Oligonucleotide annealing |
| 72° C. | 4 min 30 sec | Extension |
| For a total of 35 cycles | | |
| 72° C. | 8 min | Final extension |
| 4° C. | ∞ | |

The PCR product was purified with the "QIAquick PCR Purification Kit" (QIAGEN), digested with BglII and XbaI restriction enzymes, purified again by gel electrophoresis and gel extraction using the "QIAquick Gel Extraction" (QIAGEN). The obtained product was named Do-Fragment A.

To generate the hybrid sequence HuDo-CSPG4-1, Hu-Fragment A and Do-Fragment A were linked by means of a ligation reaction using reagents and the relative quantities are listed in table 6.

TABLE 6

| Ligation reaction (10 μl final volume) | |
|---|---|
| Reagents | Volume |
| Hu-Fragment A (30 ng) | 3 μl |
| Do-Fragment A (30 ng) | 3 μl |
| Reaction buffer 10X for T4 DNA ligase | 1 μl |
| T4 DNA ligase (2 U/μl) | 1 μl |
| H₂O | 2 μl |

The ligation reaction was incubated at 16° C. for 4 hours.
The ligation product is the hybrid sequence HuDo-CSPG4-1 containing the EcoRI and XbaI restriction sites at its ends. HuDo-CSPG4-1 (SEQ ID No.:5) includes the first 3737 bp (from the ATG start codon to the cutting site of the BglII restriction enzyme—SEQ ID No.: 15) of the human CSPG4 sequence and the remaining 3187 bp (from the cutting site of the BglII restriction enzyme to the STOP codon—SEQ ID No.: 22) of the canine CSPG4 sequence. The plasmid including the HuDo-CSPG4-1 sequence was used to perform the DNA vaccination and the immunological assays listed below.

To amplify the portion encoding the N-terminal part of the canine CSPG4 to be inserted in the DoHu-CSPG4-1, pcDNA3.1-Dog-CSPG4 and the following oligonucleotides were used:

forward oligonucleotide (SEQ ID No.:6) that anneals on the ATG start codon and including—upstream—the sequence of the EcoRI recognition site and EcoRI activity optimization followed by the Kozak sequence, SEQ ID No.: 6:
5'-CCGGAATTCGCCATGGCCCTCGGTGCTCTGCAG-3';

reverse oligonucleotide (SEQ ID No.:7) that anneals on the canine CSPG4 sequence starting from 255 bp downstream of the BglII cutting site and containing the XbaI recognition site and XbaI activity optimization, SEQ ID No.: 7:
5'-GGTCTAGACCCACGTCTAGGGAGAAGGA-3'.

PCR was performed using reagents and the "proofreading" Taq polymerase from QIAGEN. Reagent quantities and specific reaction conditions (temperatures and times) are reported in the following Tables 7 and 8.

TABLE 7

| PCR solutions (20 µl final volume) | |
|---|---|
| Reagents | Volume |
| DNA (template) | 1 µl (100 ng) |
| Buffer 10X | 2 µl |
| dNTPs 10 mM | 0.5 µl |
| Forward oligonucleotide (SEQ ID No.: 6) | 1.2 µl |
| Reverse oligonucleotide (SEQ ID No.: 7) | 1.2 µl |
| Taq Polymerase (1 U/µl) | 0.5 µl |
| $H_2O$ | 13.6 µl |

TABLE 8

| Amplification protocol | | |
|---|---|---|
| Temperature | Time | Event |
| 94° C. | 2 min | Initial denaturation |
| 94° C. | 15 sec | Denaturation |
| Gradient from 56 to 62° C. | 30 sec | Oligonucleotide annealing |
| 72° C. | 5 min | Extension |
| For a total of 35 cycles | | |
| 72° C. | 8 min | Final extension |
| 4° C. | ∞ | |

The PCR product was purified with the "QIAquick PCR Purification Kit" (QIAGEN), digested with EcoRI and BglII restriction enzymes, purified again by gel electrophoresis and gel extraction using the "QIAquick Gel Extraction" (QIAGEN). The obtained product was named Do-Fragment B.

Analogously, to amplify the portion encoding the C-terminal part of the human CSPG4 to be inserted into the sequence DoHu-CSPG4-1, the plasmid pcDNA3.1-Human-CSPG4 and the following oligonucleotides were used:

forward oligonucleotide (SEQ ID No.:8) that anneals starting from 152 bp upstream of the BglII cutting site and containing the sequence of the EcoRI recognition site and EcoRI activity optimization followed by the Kozak sequence, SEQ ID No.: 8:
5'-CCGGAATTCGCCGCCGTTCTCTATAGCCACAA-3';

reverse oligonucleotide (SEQ ID No.:9) that anneals on the STOP codon of the human CSPG4 sequence and including the sequence of the XbaI recognition site and XbaI activity optimization, SEQ ID No.: 9:
5'-GGTCTAGATCACACCCAGTACTGGCCATT-3'.

PCR was performed using reagents and the "proofreading" Taq polymerase from QIAGEN. Reagent quantities and specific reaction conditions (temperatures and times) are reported in the following Tables 9 and 10.

TABLE 9

| PCR solutions (20 µl final volume) | |
|---|---|
| Reagents | Volume |
| DNA (template) | 1 µl (100 ng) |
| Buffer 10X | 2 µl |
| dNTPs 10 mM | 0.5 µl |
| Forward oligonucleotide (SEQ ID No.: 8) | 1.2 µl |
| Reverse oligonucleotide (SEQ ID No.: 9) | 1.2 µl |
| Taq Polymerase (1 U/µl) | 0.5 µl |
| $H_2O$ | 13.6 µl |

TABLE 10

| Amplification protocol | | |
|---|---|---|
| Temperature | Time | Event |
| 94° C. | 2 min | Initial Denaturation |
| 94° C. | 15 sec | Denaturation |
| 60° C. | 30 sec | Oligonucleotide Annealing |
| 72° C. | 4 min 30 sec | Extension |
| For a total of 35 cycles | | |
| 72° C. | 8 min | Final extension |
| 4° C. | ∞ | |

The PCR product was purified with the "QIAquick PCR Purification Kit" (QIAGEN), digested with BglII and XbaI restriction enzymes, purified again by gel electrophoresis and gel extraction using the "QIAquick Gel Extraction" (QIAGEN). The obtained product was named Hu-Fragment B.

To generate the hybrid sequence DoHu-CSPG4-1, Do-Fragment B and Hu-Fragment B were linked by means of a ligation reaction using reagents and the relative quantities listed in table 11.

TABLE 11

| Ligation reaction (10 μl final volume) | |
|---|---|
| Reagents | Volume |
| Do-Fragment A (30 ng) | 3 μl |
| Hu-Fragment A (30 ng) | 3 μl |
| Reaction buffer 10X for T4 DNA ligase | 1 μl |
| T4 DNA ligase (2 U/μl) | 1 μl |
| H$_2$O | 2 μl |

The ligation reaction was incubated at 16° C. for 4 hours.

The ligation product is the hybrid sequence DoHu-CSPG4-1 containing the EcoRI and XbaI restriction sites at its ends. DoHu-CSPG4-1 (SEQ ID No.:10) includes the first 5018 bp (from the ATG start codon to the cutting site of the BglII restriction enzyme—SEQ ID No.: 16) of the canine CSPG4 sequence and the remaining 3232 bp (from the cutting site of the BglII restriction enzyme to the STOP codon—SEQ ID No.: 23) of the human CSPG4 sequence.

Construction of the pcDNA3.1-HuDo-CSPG4-1 and pcDNA3.1-DoHu-CSPG4-1 Plasmids

Ligation products HuDo-CSPG4-1 and DoHu-CSPG4-1 were purified by means of phenol/chloroform extraction (SIGMA), digested with EcoRI and XbaI restriction enzymes, purified again as described above, so that they are then able to be inserted into any suitable cloning vector. Each of the products thus obtained was inserted through a ligation reaction into the pcDNA3.1 plasmid previously digested with the same restriction enzymes, dephosphorylated using the Alkaline Phosphatase Enzyme, Calf Intestinal (BioLabs) and purified by means of gel electrophoresis and gel extraction using the "QIAquick Gel Extraction" (QIAGEN); reagents and volumes are listed in Table 12.

TABLE 12

| Ligation reaction (10 μl final volume) | |
|---|---|
| Reagents | Volume |
| DNA insert (60 ng) | 3 μl |
| Linearized DNA plasmid (pcDNA3.1) (20 ng) | 1 μl |
| Reaction buffer 10X for T4 DNA ligase | 1 μl |
| T4 DNA ligase (2 U/μl) | 1 μl |
| H$_2$O | 4 μl |

The ligation reaction was incubated at 16° C. for 4 hours.

The ligation product was then used to transform strain DH5α *E. coli* bacteria.

Transformation of strain DH5α *E. coli*

| | |
|---|---|
| Competent bacteria cells | 100 μl |
| Ligation product | 10 μl |

To transform the strain DH5α*E. coli*, competent bacteria were incubated on ice for 30 minutes with the ligation product followed by a thermic shock for 45 seconds at 42° C., and immediately transferred to ice for 2 minutes. A 1 ml-volume of *Luria Bertani* (LB) growth medium was added and transformed bacteria cells were incubated for 1 hour at 37° C. Cellular suspensions were then centrifuged at 13000 rpm for 1 minute and pellets were suspended in 150 μl of LB. Bacteria cells were then plated on petri dishes containing a solid selective medium (LB with agar+ampicillin 100 μg/ml) and left to grow overnight at 37° C. Plasmid DNA was extracted from the clones by means of the "Miniprep" kit (QIAGEN) and was subsequently analyzed by enzymatic digestion. The plasmid DNA extracted from one of the positive clones was sequenced, obtaining the SEQ ID No.:5 corresponding to the chimeric human/dog antigen of the pcDNA3.1-HuDo-CSPG4-1 plasmid, and the SEQ ID No.:10, corresponding to the chimeric dog/human antigen of the pcDNA3.1-DoHu-CSPG4-1 plasmid.

Results

Evaluation of the Immunogenicity of the Hybrid Plasmid pcDNA3.1-HuDo-CSPG4-1

In Vivo: Laboratory Mice

Firstly, the immunogenicity of the hybrid plasmid pcDNA3.1-HuDo-CSPG4-1 was evaluated in 7-week-old BALB/c female mice (Charles River). Briefly, 50 μg of pcDNA3.1-HuDo-CSPG4-1 in 20 μl of a 0.03% NaCl solution was administered intramuscularly to mice anesthetized with a solution of Zoletil (Virbac) and Rompum (Bayer). The injection was followed by electroporation by means of CLINIPORATOR (Igea). Mice vaccinated with the empty plasmid pcDNA3.1 were used as controls. The immunization was performed twice for each animal, with an interval of 14 days from each other. At 2 weeks after the last vaccination, a blood sample was taken and the presence of specific antibodies directed against the human and canine CSPG4 proteins was evaluated in the sera. In particular, sera of vaccinated animals were incubated for 45 minutes at 4° C. with human melanoma cells overexpressing the human CSPG4 protein (SK-MEL28 cells, ATCC® HTB-72™, FIG. 1A) or with canine melanoma cells expressing the canine CSPG4 protein (a primary cell line derived from a bioptic sample of a canine patient affected by CSPG4-positive oral melanoma, FIG. 1B). After washing with a solution denominated washing buffer, composed of phosphate-buffered saline (PBS) containing 0.2% of bovine serum albumin (BSA) and 0.1% of sodium azide (NaN$_3$), samples were incubated for 30 minutes at 4° C. with an FITC-conjugated anti-mouse immunoglobulin antibody (F0232, Dako), washed with washing buffer and analyzed using a FACScan cytofluorimeter instrument (Becton Dickinson Immunocytometry System).

Results demonstrated that all the animals vaccinated with the hybrid plasmid pcDNA3.1-HuDo-CSPG4-1 showed a specific antibody response against the human (FIG. 1A) and the canine (FIG. 1B) CSPG4 proteins.

These results highlight that the plasmid pcDNA3.1-HuDo-CSPG4-1: i) encodes for a chimeric human/dog CSPG4 protein, correctly translated; ii) is immunogenic in mice, inducing an antibody response against both the human and the canine CSPG4 proteins.

In Vivo: Dogs

To evaluate the immunogenicity and the consequent antitumor potential of the plasmid pcDNA3.1-HuDo-CSPG4-1 against CSPG4-positive tumors in the veterinary field, dogs affected by stage II and III, CSPG4-positive oral melanoma were vaccinated with the hybrid plasmid in question, 1 month after surgical resection of the tumor. The DNA vaccination protocol consisted of one injection—in the caudal muscle of the leg—of 500 μg of pcDNA3.1-HuDo-CSPG4-1 plasmid in 200 μl of 0.03% NaCl solution, followed by electroporation by means of CLINIPORATOR (Igea). The vaccination was then repeated after 2 weeks and then monthly.

Figure 2:
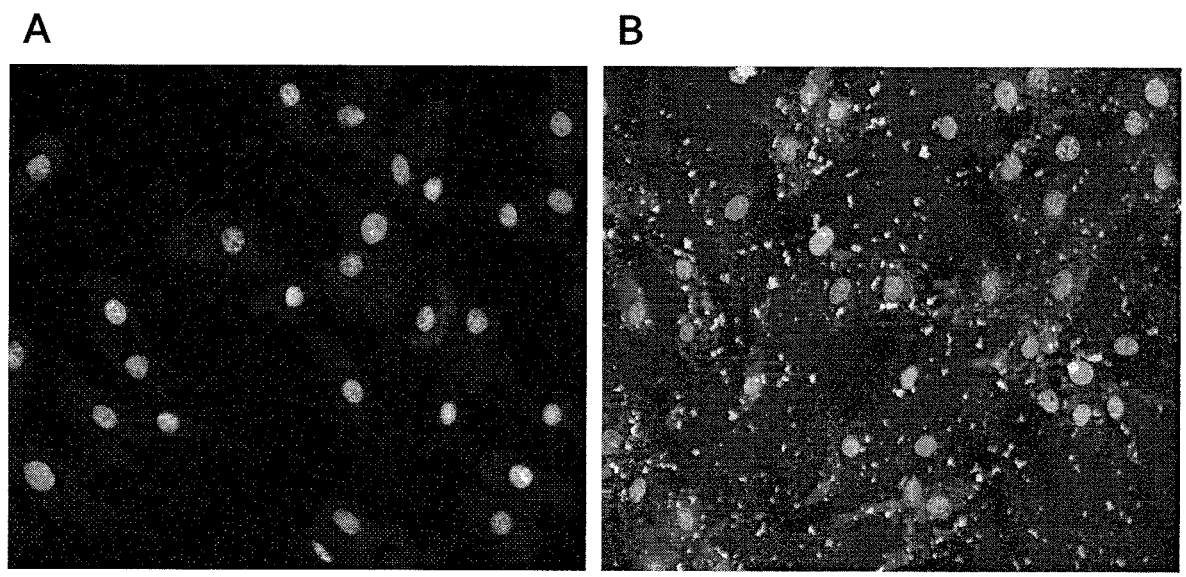
FIG. 2. Immunofluorescence assay to evaluate the specific antibody response against a primary cell line obtained from a bioptic sample of a dog affected by CSPG4-positive oral melanoma, induced in a canine patient vaccinated with plasmid pcDNA3.1-HuDo-CSPG4-1. Representative images of primary melanoma cells incubated with the serum of a canine patient before the start of the vaccination cycle (A) and after the IV immunization (B). A secondary FITC-conjugated antibody (F7884, Sigma) was used to reveal canine immunoglobulins that recognized canine CSPG4 protein in its native conformation on the membrane of the primary melanoma cells. Cell nuclei were stained with DAPI. Magnification 20×.

Serum of the canine patients was collected before the start of the vaccination cycle and after the IV immunization, and the presence of specific antibodies against the canine CSPG4 protein was evaluated by means of an immunofluorescence assay. In particular, CSPG4-positive canine melanoma cells were plated on immunofluorescence slides, fixed in 4% formalin and incubated for 1 hour at room temperature with animal sera (diluted 1:10) collected before the vaccination and after the IV immunization. Cells were then washed twice with PBS and were incubated with a FITC-conjugated anti-dog immunoglobulin antibody (F7884, Sigma). After three washes with PBS, slides were air-dried and mounted using Fluoromount Aqueous Mounting Medium (Sigma) and then analyzed using a Zeiss axiovert 200M fluorescence-inverted microscope equipped with the Apotome Zeiss system, which uses a CCD camera as image detector. FIG. 2 reports representative results obtained by one of the vaccinated dogs.

The data demonstrate that the plasmid pCDNA3.1-HuDo-CSPG4-1 is effective in breaking the tolerance in canine patients affected by CSPG4-positive oral melanoma. Indeed, immunization with the plasmid pcDNA3.1-HuDo-CSPG4-1 induces—in the vaccinated dogs—a specific antibody response against the canine CSPG4 protein, demonstrating an anti-tumoral effect for the treatment of CSPG4-positive canine tumors.

In Vitro: Human

Finally, we performed "human surrogate" assays to evaluate, in a human clinical context, the efficacy of the hybrid plasmid pcDNA3.1-HuDo-CSPG4-1 in breaking the immunological tolerance and reverting the unresponsiveness of the T cells against the tolerated CSPG4 antigen.

In particular, we generated in vitro mature dendritic cells (mDC) from CD14+ monocytes derived from the blood of HLA-A2-positive healthy donors obtained from the Blood Bank of Torino, according to the protocol described in (Occhipinti et al. 2014). The mDC were then transfected using the "DC transfection kit" (Amaxa, Lonza) with pcDNA3.1-Human-CSPG4, pcDNA3.1-HuDo-CSPG4-1 plasmids or with the empty control pcDNA3.1 plasmid. Transfected mDC were used to stimulate autologous T cells from the healthy donor.

Figure 3:
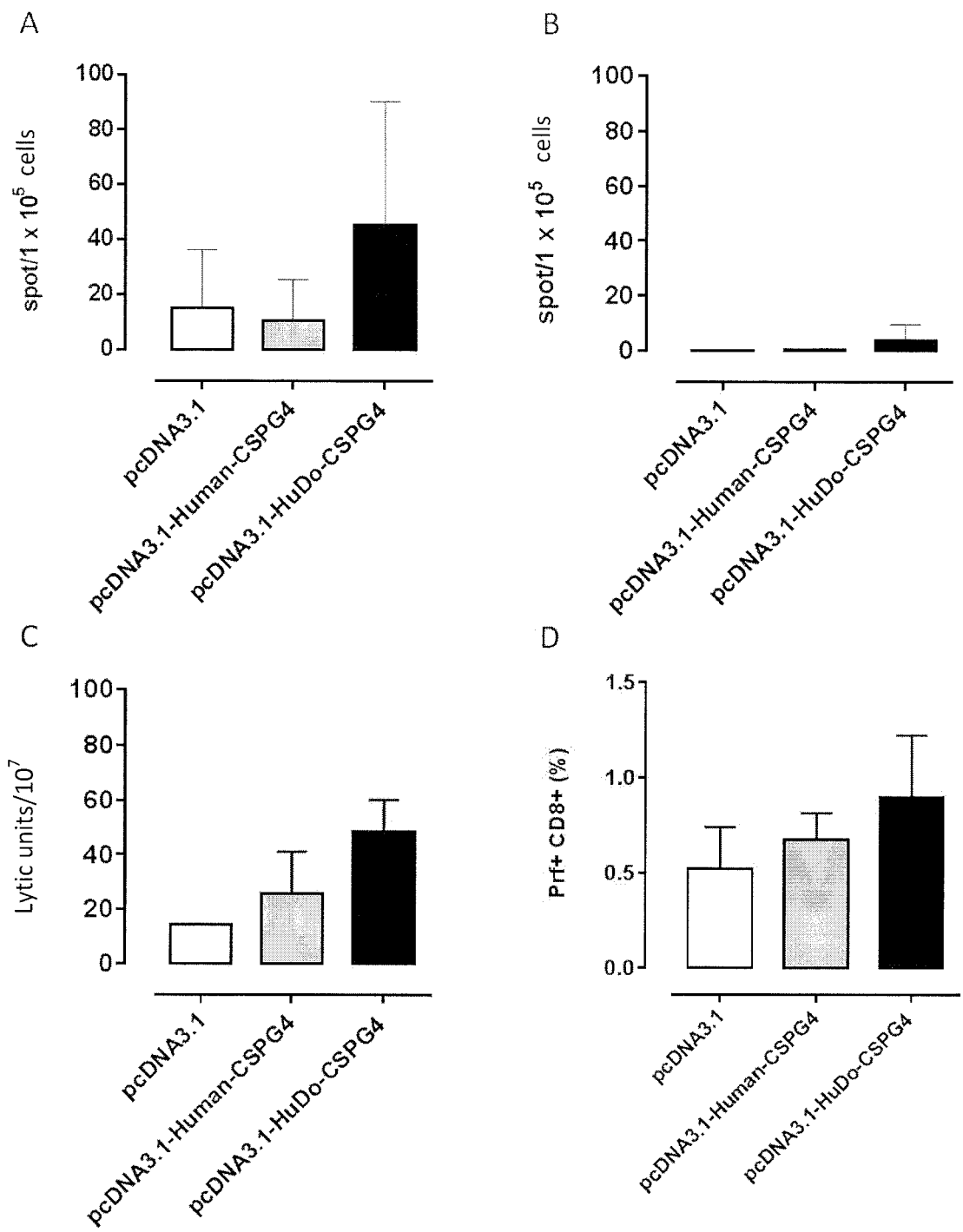
FIG. 3. Evaluation of the activation of T lymphocytes from healthy human donors following 7 days of co-culture with mature dendritic cells (mDC) transfected with empty pCDNA3.1, pCDNA3.1-Human-CSPG4 (Yang et al. 2004) and pCDNA3.1-HuDo-CSPG4-1. The specific IFNγ release from pre-stimulated T lymphocytes against CSPG4-positive human melanoma cells Mel1300 [kind gift from P. Circosta and maintained in culture as described in (Circosta et al. 2009)] was evaluated in the absence (A) or presence (B) of an antibody against HLA class I molecules (W6/32, Sigma). The number of spots were counted with a Transtec 1300 ELISPOT Reader (AMI Bioline) and results were expressed as number of spots/1×$10^5$ cells. (C) The release of $^{51}$Cr from labeled CSPG4-positive Mel1300 cells, following incubation with lymphocytes pre-stimulated in the different conditions was detected, and results were expressed as number of lytic unit/$10^7$ effector cells. (D) The intracellular expression of perforin (Pfp) within CD8+ cells was evaluated using an APC-conjugated antibody directed against Pfp (clone dG9, Biolegend) and the results were expressed as percentage of Pfp+ and CD8+ cells.

After 7 days of co-culture, the activation of T cells against the human CSPG4 protein was evaluated by means of an interferon-γ (IFNγ)-enzyme-linked immunospot assay (ELISPOT). In particular, lymphocytes pre-stimulated with mDC transfected with the different plasmids were incubated with the human HLA-A2 CSPG4-positive Mel1300 melanoma cell line (publicly available from P. Circosta at the Immune Oncology Lab, Istituto per la Ricerca e la Cura del Cancro di Candiolo, 10060, Torino, Italy) and maintained in culture as described in (Circosta et al. 2009), and the specific IFNγ release was evaluated. Results show that after 7 days of co-culture, T lymphocytes pre-stimulated with mDC transfected with the hybrid pcDNA3.1-HuDo-CSPG4-1 plasmid were able to release IFNγ against the CSPG4-positive Mel1300 cells in higher quantities compared to the IFNγ release detected when T lymphocytes were pre-stimulated with mDC transfected with the pcDNA3.1-Human-CSPG4 or empty pcDNA3.1 plasmids (FIG. 3A). This response of T lymphocytes pre-stimulated with pcDNA3.1-HuDo-CSPG4-1 transfected mDC is specific since it was completely abolished when an antibody (W6/32, Sigma) blocking the HLA class I molecules on the surface of Mel1300 cells was used in the assay (FIG. 3B).

Moreover, an in vitro cytotoxicity assay was performed; briefly, Mel1300 cells were labeled with $^{51}$Cr (PerkinElmer) in 5% $CO_2$ for 1 hour at 37° C. and after washing with PBS, 5×10$^3$ cells were co-incubated in a final volume of 200 µl with effector T cells recovered after 7 days of co-culture with transfected mDC. After 4 hours of incubation, 50 µl of supernatant was collected and the radioactivity was measured using a "TopCount Scintillation Counter" (Packard Biosciences). In this in vitro cytoxicity assay, only T lymphocytes pre-activated with pcDNA3.1-HuDo-CSPG4-1 tranfected mDC, but not those transfected with pcDNA3.1-Human-CSPG4 (Yang et al. 2004) or the empty pcDNA3.1, were able to specifically kill CSPG4-positive melanoma cells (FIG. 3C). When T cells pre-stimulated in the different conditions were stimulated again with monoclonal antibodies anti-CD3/anti-CD28 (1 mg/ml anti-human CD3 mAb: OKt 3, eBioscience; 1 mg/ml anti-human CD28 mAb: CD28.2, Biolegend) in the presence of Brefeldin A (10 mg/ml, Sigma) for 6 hours at 37° C., intracellular perforin production was analyzed. In particular, cells were treated with a fixing and permeabilization solution (eBioscience) for 45 minutes at 4° C., and after washing, cells were incubated for 30 minutes at 4° C. with an APC-conjugated antibody directed against the perforin (clone dG9, Biolegend). An increasing percentage of CD8+ lymphocytes producing perforin was evident when lymphocytes were pre-stimulated with pcDNA3.1-HuDo-CSPG4-1 transfected mDC compared to those pre-stimulated with mDC transfected with pcDNA3.1-Human-CSPG4 or empty pcDNA3.1 (FIG. 3D).

These results show the ability of pcDNA3.1-HuDo-CSPG4-1 plasmid to break the tolerance and the unresponsiveness of T cells against the CSPG4 self-antigen, highlighting its application in human clinical oncology.

REFERENCES

Bergman, P. J. (2007). "Canine oral melanoma." Clin Tech Small Anim Pract 22(2): 55-60. doi: 10.1053/j.ctsap.2007.03.004.

Boston, S. E., X. Lu, W. T. Culp, V. Montinaro, G. Romanelli, R. M. Dudley, J. M. Liptak, L. A. Mestrinho and P. Buracco (2014). "Efficacy of systemic adjuvant therapies administered to dogs after excision of oral malignant melanomas: 151 cases (2001-2012)." J Am Vet Med Assoc 245(4): 401-407. doi: 10.2460/javma.245.4.401.

Campoli, M., S. Ferrone and X. Wang (2010). "Functional and clinical relevance of chondroitin sulfate proteoglycan 4." Adv Cancer Res 109: 73-121. doi: 10.1016/B978-0-12-380890-5.00003-X.

Cheever, M. A., J. P. Allison, A. S. Ferris, O. J. Finn, B. M. Hastings, T. T. Hecht, I. Mellman, S. A. Prindiville, J. L. Viner, L. M. Weiner and L. M. Matrisian (2009). "The prioritization of cancer antigens: a national cancer institute pilot project for the acceleration of translational research." Clin Cancer Res 15(17): 5323-5337. doi: 10.1158/1078-0432.CCR-09-0737.

Circosta, P., L. Granziero, A. Follenzi, E. Vigna, S. Stella, A. Vallario, A. R. Elia, L. Gammaitoni, K. Vitaggio, F. Orso, M. Geuna, D. Sangiolo, M. Todorovic, C. Giachino and A. Cignetti (2009). "T cell receptor (TCR) gene transfer with lentiviral vectors allows efficient redirection of tumor specificity in naive and memory T cells without prior stimulation of endogenous TCR." Hum Gene Ther 20(12): 1576-1588. doi: 10.1089/hum.2009.117.

Petrovici, K., M. Graf, K. Hecht, S. Reif, K. Pfister and H. Schmetzer (2010). "Use of NG2 (7.1) in AML as a tumor marker and its association with a poor prognosis." Cancer Genomics Proteomics 7(4): 173-180. doi.

Riccardo, F., S. Iussich, L. Maniscalco, S. Lorda Mayayo, G. La Rosa, M. Arigoni, R. De Maria, F. Gattino, S. Lanzardo, E. Lardone, M. Martano, E. Morello, S. Prestigio, A. Fiore, E. Quaglino, S. Zabarino, S. Ferrone, P. Buracco and F. Cavallo (2014). "CSPG4-specific immunity and survival prolongation in dogs with oral malignant melanoma immunized with human CSPG4 DNA." *Clin Cancer Res* 20(14): 3753-3762. doi: 10.1158/1078-0432.CCR-13-3042.

Simpson, R. M., B. C. Bastian, H. T. Michael, J. D. Webster, M. L. Prasad, C. M. Conway, V. M. Prieto, J. M. Gary, M. H. Goldschmidt, D. G. Esplin, R. C. Smedley, A. Piris, D. J. Meuten, M. Kiupel, C. C. Lee, J. M. Ward, J. E. Dwyer, B. J. Davis, M. R. Anver, A. A. Molinolo, S. B. Hoover, J. Rodriguez-Canales and S. M. Hewitt (2014). "Sporadic naturally occurring melanoma in dogs as a preclinical model for human melanoma." *Pigment Cell Melanoma Res* 27(1): 37-47. doi: 10.1111/pcmr.12185.

Stallcup, W. B. and F. J. Huang (2008). "A role for the NG2 proteoglycan in glioma progression." *Cell Adh Migr* 2(3): 192-201. doi: PMC2634088.

Wang, X., T. Osada, Y. Wang, L. Yu, K. Sakakura, A. Katayama, J. B. McCarthy, A. Brufsky, M. Chivukula, T. Khoury, D. S. Hsu, W. T. Barry, H. K. Lyerly, T. M. Clay and S. Ferrone (2010a). "CSPG4 protein as a new target for the antibody-based immunotherapy of triple-negative breast cancer." *J Natl Cancer Inst* 102(19): 1496-1512. doi: 10.1093/jnci/djq343. PMC2950168.

Wang, X., Y. Wang, L. Yu, K. Sakakura, C. Visus, J. H. Schwab, C. R. Ferrone, E. Favoino, Y. Koya, M. R. Campoli, J. B. McCarthy, A. B. DeLeo and S. Ferrone (2010b). "CSPG4 in cancer: multiple roles." *Curr Mol Med* 10(4): 419-429. doi: CMM #48 [pii].

Wilson, B. S., K. Imai, P. G. Natali and S. Ferrone (1981). "Distribution and molecular characterization of a cell-surface and a cytoplasmic antigen detectable in human melanoma cells with monoclonal antibodies." *Int J Cancer* 28(3): 293-300. doi.

Yang, J., M. A. Price, C. L. Neudauer, C. Wilson, S. Ferrone, H. Xia, J. Iida, M. A. Simpson and J. B. McCarthy (2004). "Melanoma chondroitin sulfate proteoglycan enhances FAK and ERK activation by distinct mechanisms." *J Cell Biol* 165(6): 881-891. doi: 10.1083/jcb.200403174. PMC2172406.

The invention claimed is:

1. A nucleic acid molecule encoding a chimeric chondroitin sulfate proteoglycan-4 (CSPG4) protein, wherein the chimeric CSPG4 protein comprises, from the N-terminus to the C-terminus:
   i) a first portion derived from the human sequence of CSPG4 and a second portion derived from the canine sequence of CSPG4, or
   ii) a first portion derived from the canine sequence of CSPG4 and a second portion derived from the human sequence of CSPG4, wherein the first portion has an amino acid sequence encoded by a nucleotide sequence selected from SEQ ID No.: 11 to 17, and the second portion has an amino acid sequence encoded by a nucleotide sequence selected from SEQ ID No.: 18 to 23, and wherein the first and second portions are adjacent to each other and are linked as indicated in the following table:

| First portion | Second portion |
|---|---|
| SEQ ID No.: 11 | SEQ ID No.: 18 |
| SEQ ID No.: 12 | SEQ ID No.: 19 |
| SEQ ID No.: 13 | SEQ ID No.: 20 |
| SEQ ID No.: 14 | SEQ ID No.: 21 |
| SEQ ID No.: 15 | SEQ ID No.: 22 |
| SEQ ID No.: 16 | SEQ ID No.: 23 |
| SEQ ID No.: 17 | SEQ ID No.: 23. |

2. The nucleic acid molecule encoding a chimeric CSPG4 protein according to claim 1, wherein the first portion has an amino acid sequence encoded by a nucleotide sequence selected from SEQ ID No.: 11, 15 and 17 and the second portion has an amino acid sequence encoded by a nucleotide sequence selected from SEQ ID No.: 18, 22 and 23 and wherein the first and second portions are adjacent to each other and are linked as indicated in the following table:

| First portion | Second portion |
|---|---|
| SEQ ID No.: 11 | SEQ ID No.: 18 |
| SEQ ID No.: 15 | SEQ ID No.: 22 |
| SEQ ID No.: 17 | SEQ ID No.: 23. |

3. A pharmaceutical composition comprising at least one nucleic acid molecule encoding a chimeric CSPG4 protein according to claim 1 and a pharmaceutically acceptable excipient and/or vehicle.

4. An immunogenic composition comprising the pharmaceutical composition according to claim 3.

5. The immunogenic composition according to claim 4, comprising an adjuvant.

6. An immunogenic composition comprising the nucleic acid molecule encoding a chimeric CSPG4 protein according to claim 1.

7. A method of treating CSPG-4 positive neoplasia in a mammal, comprising administering to a subject in need thereof a therapeutically effective amount of the nucleic acid molecule encoding a chimeric CSPG4 protein according to claim 1.

8. The method of claim 7, wherein the nucleic acid molecule encoding a chimeric CSPG4 protein is part of a plasmid.

9. The method of claim 7, wherein the mammal is a human.

10. The method of claim 7, wherein the mammal is a dog.

* * * * *